US006890534B1

(12) United States Patent
Georgopoulos et al.

(10) Patent No.: US 6,890,534 B1
(45) Date of Patent: May 10, 2005

(54) AIOLOS GENE

(75) Inventors: Katia Georgopoulos, Lexington, MA (US); Bruce A. Morgan, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/019,348

(22) Filed: Feb. 5, 1998

Related U.S. Application Data

(62) Division of application No. 08/733,622, filed on Oct. 17, 1996, now Pat. No. 6,528,634.
(60) Provisional application No. 60/017,646, filed on May 14, 1996, and provisional application No. 60/005,529, filed on Oct. 18, 1995.

(51) Int. Cl.[7] .............................................. A61K 39/00

(52) U.S. Cl. .................................................. 424/184.1

(58) Field of Search ............................... 435/70.2, 376; 530/387.1; 424/184.1

(56) References Cited

FOREIGN PATENT DOCUMENTS

| WO | WO 94/06814 | 3/1994 |
|----|----|----|
| WO | WO 96/04372a1 | 2/1996 |
| WO | WO 97/14714 | 4/1997 |

OTHER PUBLICATIONS

Frosch et al. Proc. Natl. Acad Sci USA 2:1194, 1985.*
Georgopoulos et al., "Tissue–specific nuclear factors mediate expresion of the CD3–delta gene during T cell development" EMBO Journal 9:109–115 (1992).
Georgopoulos et al., "Ikaros, an early lymphoid–specific transcription factor and a putative mediator T cell commitment" SCIENCE 258:808–812 (1992).
Georgopoulos et al., Ikaros an early lymphoid restricted regulatory protein, a putative modulator for T cell specification J. Cellular Biochem. vol. Suppl. 17A:B631 (1993).
Singh et al, Molecular cloning of an enchancer binding protein: isolation by screening of an expression library with a recognition site DNA Cell 52:415–423 (1988).
van de Wetering, M. et al. "Identification and cloning of TCF–1, a T lymphocyte–specific transcription factor containing a sequence–specific HMG box" The EMBO Journal 10 (1): 123–132 (1991).
von Boehmer, H. "The Developmental Biology of T Lymphocytes" Ann. Rev. Immunol. 6: 309–326 (1988).
Waterman, M.L. et al. "A thymus–specific member of the HMG protein family regulates the human T cell receptor Cα enhancer" Genes & Development 5: 656–669 (1991).
Weintraub, H. "The MyoD Family and Myogenesis: Redundancy, Networks, and Thresholds" Cell 75: 1241–1244 (Dec. 31, 1993).
Xu, Y. et al. "LH–2: A LIM/homeodomain gene expressed in developing lymphocytes and neural cells" Proc. Natl. Acad Sci. USA 90: 227–231 (1993).
Yokoyama, W.M. "Flow Cytometry Analysis Using the Becton Dickinson FACScan" in Current Protocols in Immunology, J.E. Coligan et al. (Eds.), Brooklyn, NY: Greene Publishing Associates, 5.4.1–5.4.14 (1992).
Zervos, A.S. et al. "Mxi1, a Protein that Specifically Interacts with Max to Bind Myc–Max Recognition Sites" Cell 72: 223–232 (1993).
Oltvai, Z.N. et al. "Bcl–2 Heterodimerizes In Vivo with a Conserved Homolog, Bax, That Accelerates Programed Cell Death"Cell 74: 609–619 (1993).
Oosterwegel, M. et al. "Cloning of Murine TCF–1, a T Cell–specific Transcription Factor Interacting with Functional Motifs in the CD3–ε and T Cell Receptor α Enhancers" J. Exp. Med. 173:1133–1142 (May 1991).
Oosterwegel, M. et al. "Differential expression of the HMG box factors TCF–1 and LEF–1 during murine embryogenesis" Development 118: 439–448 (1993).
Philpott, K.L. et al. "Lymphoid Development in Mice Congenitally Lacking T Cell Receptor αβ–Expressing Cells" Science 256: 1448–1452 (Jun. 5, 1992).
Raulet, D.H. et al. "Control of γδ T–Cell Development" Immunological Reviews 120:185–204 (1991).
Read, D. and J.L. Manley "Alternatively spliced transcripts of the Drosophila tramtrack gene encode zinc finger proteins with distinct DNA binding specificities" The EMBO Journal 11(3): 1035–1044 (1992).
Rodewald, H.–R. et al. "A Population of Early Fetal Thymocytes Expressing FcγRII/III Contains Precursors of T Lymphocytes and Natural Killer Cells" Cell 69: 139–150 (1992).
Rolink, A. and F. Melchers "Molecular and Cellular Origins of B Lymphocyte Diversity" Cell 66: 1061–1094 (1991).
Rudnicki, M.A. et al. "Inactivation of MyoD in Mice Leads to Up–Regulation of the Myogenic HLH Gene Myf–5 and Results in Apparently Normal Muscle Development" Cell 71: 383–390 (1992).
Sawyers, C.L. et al. "Leukemia and the Disruption of Normal Hematopoiesis" Cell 64: 337–350 (1991).
Sentman, C.L. et al. "bcl–2 Inhibits Multiple Forms of Apoptosis but Not Negative Selection in Thymocytes" Cell 67:879–888 (1991).
Shinkai, Y. et al. "RAG–2 Deficient Mice Lack Mature Lymphocytes Owing to Inability to Initiate V(D)J Rearrangement" Cell 68: 855–867 (1992).

(Continued)

Primary Examiner—Patrick J. Nolan
(74) Attorney, Agent, or Firm—Fish & Richardson P.C.

(57) ABSTRACT

The invention features an Aiolos protein, and nucleic acid sequence encoding such protein. The invention also features methods of making and using an Aiolos protein, and methods of obtaining an antibody from an animal having an Aiolos deregulated cell.

26 Claims, 10 Drawing Sheets

OTHER PUBLICATIONS

Skeath, J.B. et al. "Gene regulation in two dimensions" the proneural *achaete* and *scute* genes are controlled by combinations of axis–patterning genes through a common intergenic control region *Genes & Development* 6: 2606–2619 (1992).

Spangrude, G.J. "Enrichment of murine haemopoietic stem cells: diverging roads" *Immunology Today* 10(10): 344–350 (1989).

Spangrude, G.J. et al. "Purification and Characterization of Mouse Hematopoeitic Stem Cells" *Science* 241:58–62 (Jul. 1, 1988).

Spanopoulou, E. et al. "Functional immunoglobulin transgenes guide ordered B–cell differentiation in Rag–1–deficient mice" *Genes & Development* 8: 1030–1042 (1994).

Travis, A. et al. "LEF–1, a gene encoding a lymphoid–specific with protein, an HMG domain, regulates T–cell receptor β enhancer function" *Genes & Development* 5:880–894 (1991).

Turner, Jr., C.A. et al. "Blimp–1, a Novel Zinc Finger–Containing Protein that Can Drive the Maturation of B Lymphocytes into Immunoglobulin–Secreting Cells" *Cell* 77: 297–306 (Apr. 22, 1994).

Hsu, T. et al. "Multiple Zinc Finger Forms Resulting from Developmentally Regulated Alternative Splicing of a Transcription Factor Gene" *Science* 257: 1946–1950 (1992).

Ikuta, K. et al. "A Developmental Switch in Thymic Lymphocyte Maturation Potential Occurs at the Level of Hematopoietic Stem Cells" *Cell* 62: 863–874 (1990).

Ikuta, K. et al. "Lymphocyte Development From Stem Cells" *Annu. Rev. Immunol.* 10: 759–783 (1992).

Jiang, J. and M. Levine "Binding Affinities and Cooperative Interactions with bHLH Activators Delimit Threshold Responses to the Dorsal Gradient Morphogen" *Cell* 72: 741–752 (1993).

Juhlin, L. and W.B. Shelley "New Staining Techniques for the Langerhans Cell" *Acta Dermatovener* 57:289–296 (1977).

Kang, S.–M. et al. "NF–κB Subunit Regulation in Nontransformed CD4$^+$ T Lymphocytes" *Science* 256: 1452–1456 (1992).

Karasuyama, H. et al. "The Expression of $V_{pre-B}\lambda 5$ Surrogate Light Chain In Early Bone Marrow Precursor B Cells of Normal and B Cell–Deficient Mutant Mice" *Cell* 77: 133–143 (Apr. 8, 1994).

Lagasse, E. and I.L. Weissman "BCL–2 Transgene Inhibits Neutrophils Cell Death But Not Their Engulfment By Microphages" *J. Biochem.* 0 (Suppl. 17D): 168 (Mar. 13–31, 1993).

Leiden, J.M. "Transcriptional regulation during T–cell development: The β TCR gene as a molecular model" *Immunology Today* 13(1): 22–30 (Jan. 1992).

Lenardo, M.J. and D. Baltimore "NF–κB: A Pleiotropic Mediator of Inducible and Tissue–Specific Gene Control" *Cell* 58: 227–229 (1989).

Li, E. et al. "Targeted Mutation of the DNA Methyltransferase Gene Results in Embryonic Lethality" *Cell* 69: 915–926 (1992).

Li, Y.–S. et al. "The Regulated Expression of B Lineage Associated Genes during B Cell Differentiation in Bone Marrow and Fetal Liver" *J. Exp. Med.* 178: 951–960 (1993).

Liang, P. et al. "Distribution and cloning of eukaryotic mRNAs by means of differential display: refinements and optimization" *Nucleic Acids Research* 21 (14): 3269–3275 (1993).

Mann, R. et al. "Construction of a Retrovirus Packaging Mutant and Its Use to Produce Helper–Free Defective Retrovirus" *Cell* 33: 153–159 (1993).

Martin, D.I.K. et al. "Expression of an erythroid transcription factor in megakaryocytic and mast cell lineages" *Nature* 344: 444–447 (1990).

McDonnell, T.J. and S.J. Korsmeyer "Progression from lymphoid hyperplasia to high–grade malignant lymphoma in mice transgenic for the t(14; 18)" *Nature* 349: 254–256 (1991).

McDonnell, T.J. et al. "bcl–2–Immunoglobulin Transgenic Mice Demonstrate Extended B Cell Survival and Follicular Lymphoproliferation" *Cell* 57: 79–88 (1989).

Metcalf, D. "The molecular control of cell division, differentiation commitment and maturation in haemopoietic cells" *Nature* 339:27–30 (1989).

Mombaerts, P. et al. "RAG–1 Deficient Mice Have No Mature B and T Lymphocytes" *Cell* 68:869–877 (1992).

Mucenski, M.L. et al. "A Functional c–myb Gene is Required for Normal Murine Fetal Hepatic Hematopoiesis" *Cell* 65: 677–689 (1991).

Fife, A. et al., "Gram negative septicaemia diagnosed on peripheral blood smear appearances" *Journal of Clinical Pathology* 47: 82–84 (1994).

Fleming, W.H. et al. "Functional Heterogeneity Is Associated with the Cell Cycle Status of Murine Hematopoietic Stem Cells" *J. Cell Biol.* 122: 897–902 (1993).

Franzoso, G. et al. "The oncoprotein Bcl–3 can facilitate NF–κB–mediated transactivation by removing inhibiting p50 homodimers from selectκB sites" *The EMBO Journal*, vol. 12, No. 10 3893–3901 (1993).

Furley, A.J. et al. "Developmentally Regulated Rearrangement and Expression of Genes Encoding the T Cell Receptor–T3 Complex" *Cell*, vol. 46: 75–87 (Jul. 1986).

Garni–Wagner, B.A. et al. "Natural Killer Cells in the Thymus" *The Journal of Immunology* 144 (3): 796–803 (1990).

Georgopoulos, K. et al. "Functionally Distinct Isoforms of the CRE–BP DNA–Binding Protein Mediate Activity of a T–Cell–Specific Enhancer" *Molecular and Cellular Biology* 12(2): 747–757 (Feb. 1992).

Georgopoulos, K. et al. "A T cell–specific enhancer is located in a DNase I–hypersensitive area at the 3' end of the CD3–δ gene" *The EMBO Journal* 7(8): 2401–2407 (Aug. 1988).

Godfrey, D.I. and A. Zlotnik "Control points in early T–cell development" *Immunology Today* 14(11): 547–553 (1993).

Gogos, J.A. et al. "Sequence Discrimination by Alternatively Spliced Isoforms of a DNA Binding Zinc Finger Domain" *Science* 257: 1951–1955 (1992).

Hackett, Jr., J. et al. "Origin and Differentiation of Natural Killer Cells" *The Journal of Immunology* 136(8): 3124–3131 (1986).

Hackett, Jr., J. et al. "Transplantable progenitors of natural killer cells are distinct from those of T and B lymphocytes" *Proc. Natl. Acad. Sci USA* 83: 3427–3431 (1986).

Hardy, R.R. et al. "Resolution and Characterization of Pro–B and Pre–Pro–B Cell Stages in Normal Mouse Bone Marrow" *J. Exp. Med.* 173: 1213–1225 (May 1991).

Havran, W.L. and J.P. Allison. "Developmentally ordered appearance of thymocytes expressing different T–cells antigen receptors" *Nature* 335: 443–445 (1988).

Havran, W.L. and J.P. Allision "Origin of Thy–1+ dendritic epidermal cells of adult mice from fetal thymic precursors" *Nature* 344: 68–70 (1990).

Havran, W.L. et al. "Limited diversity of T–cell receptor γ–chain expression of murine Thy–1+ dendritic epidermal cells revealed by Vγ3–specific monoclonal antibody" *Proc. Natl. Acad. Sci. USA* 86: 4185–4189 (1989).

Haynes, B. et al. "Ontogeny of T–cell precursors: a model for the initial stages of human T–cell development" *Immunology Today* 10(3): 87–90 (1989).

Hestdal, K. et al. "Characterization and Regulation of RB6–8C5 Antigen Expression on Murine Bone Marrow Cells" *J. Immunol.* 147(1): 22–28 (Jul. 1, 1991).

Ho, I.–C. et al. "Human GATA–3: a lineage–restricted transcription factor that regulates the expression of the T cell receptor α gene" *The EMBO Journal* 10(5):1187–1192 (1991).

Ho, I.–C. et al. "Sequence–Specific Binding of Human Ets–1 to the T Cell Receptor α Gene Enhancer" *Science* 250: 814–818 (1990).

Adams, B. et al. "Pax–5– encodes the transcription factor BSAP and is expressed in B lymphocytes, the developing CNS, and adult testis" *Genes & Development* 6:1589–1607 (1992).

Akbar, A.N. et al. "A possible role for bcl–2 in regulating T–cell memory—a 'balancing act' between cell death and survival" *Immunology Today* 14(11): 526–531 (1993).

Ardavin, C. et al. "Thymic dendritic cells and T cells develop simultaneously in the thymus from a common precursor population" *Nature* 362; 761–763 (1993).

Asarnow, D.M. et al. "Limited Diversity of γδ Antigen Receptor Genes of Thy–1+ Dendritic Epidermal Cells" *Cell* 55: 837–847 (Dec. 2, 1988).

Beg, A.A. et al. "The IκB proteins: multifunctional regulators of Rel/NF–κB transcription factors" *Genes & Development* 7: 2064–2070 (1993).

Bigby, M. et al. "Ratio of Langerhan Cells to Thy–1+ Dendritic Epidermal Cells in Murine Epidermis Influences the Intensity of Contact Hypersensitivity" *The Journal of Investigative Dermatology* 89(5): 495–499 (Nov. 1987).

Boise, L.H. et al. "bcl–x, bcl–2–Related Gene that Functions as a Dominant Regulator of Apoptotic Cell Death" *Cell* 74: 597–608 (1993).

Bours, V. et al. "The Oncoprotein Bcl–3 Directly Transactivates throughκB Motifs via Association with DNA–Binding p50B Homodimers" *Cell* 72: 729–739 (1993).

Cepko, C.L. et al "Construction and Applications of a Highly Transmissible Murine Retrovirus Shuttle Vector" *Cell* 37: 1053–1062 (1984).

Clevers, H.C. et al. "Transcription factors in early T–cell development" *Immunology Today* 14(2): 591–596 (1993).

Connelly, C.S. et al. "The Role of Transgenic Animals in the Analysis of Various Biological Aspects of Normal and Pathologic States" *Experimental Cell Research* 183: 257–276 (1989).

Dewel, R. et al. Four of the Seven Zinc Fingers of the Evi–1 Myeloid–Transforming Gene Are Required for Sequence–Specific Binding to GA(C/T)AAGA(T/C)AAGATAA, *Molecular and Cellular Biology* 13(7): 4291–4300 (1993).

Ehlich, A. et al. "Immunoglobulin Heavy and Light Chain Genes Rearrange Independently at Early Stages of B Cell Development" *Cell* 72: 695–704 (1993).

Georgopoulos et al., "The Ikaros gene is required for the development of all lymphoid lineages" *Cell* 79:143–156 (1994).

Hahm et al., "The lymphoid transcription factor LyF–1 is encoded by specific, alternatively spliced mRNAs derived from the Ikaros gene", MOL. And Cell. Biology 14:7111–7123 (1994).

Molnar et al., "The Ikaros gene encodes a family of functionally diverse zinc finger DNA–binding proteins";Mol. and Cell. Biology 14:8292–8303 (1994).

Winandy et al; "A dominant mutation in the Ikaros gene leads to rapid development of leukemia and lymphoma", *Cell* 83:289–299 (1995).

Morgan et al. "Ailos, A Lymphoid Restricted Transcription Factor That Interacts With Ikaros To Regulate Lymphocyte Differentiation" *The EMBO Journal* 8(16):2004–2013 (1997).

Wang, Jin–Hong et al., "*Ailos* Regulates B Cell Activation and Maturation to Effector State" *Immunity*, vol. 9: pp. 543–553 (1998).

* cited by examiner

1A. MOUSE AIOLOS cDNA SEQUENCE

CACGAGCGCACACCGCTCGGCTCTCCTTGCGACACGCCCTCATCCCCGGTGTT
TCTCAAGTAGACGTCCCGAGACGGTCGCTGAGGCACTGTTTCCACGCGATCA
GGGTTCCTCAGGCTTGACATTCAAAAGTGGGTGCGGAACCCGCGGCACTCGG
AGCGTGCTTTAAAGCGGCCGCCAGCCAGCGCCGCTCTAACCTCGCGCCCCGG
CTGCCGGCGGCTCCCGCCCTGCATCTGCGCCGACGCGACCGAGCGATCCCGG
GGCCTCCTGCGCCCGGAATCTCCCGCCAGCCGCGCGGGTCCCCACGGCAGC
AGCACGTGGAGCGGCCGCGGAGCCTGAGCGACAGCTGCAGCCCGCGCGGCC
CGCGGCGACATGGAAGATATACAACCGACTGTGGAGCTGAAAAGCACGGAG
GAGCAGCCTCTGCCCACAGAGAGCCCAGACGCTCTGAATGACTACAGCTTGC
CCAAACCTCATGAGATAGAAACGTGGACAGTAGAGAAGCCCCAGCCAATG
AAGACGAAGATGCAGGAGAAGATTCGATGAAAGTGAAAGATGAATACAGCG
ACAGAGATGAGAACATTATGAAGCCGGAGCCCATGGGAGATGCAGAAGAGA
GTGAAATGCCTTACAGCTATGCAAGAGAATACAGCGACTATGAAAGCATTAA
GCTGGAGAGACACGTGCCCTATGACAACAGCAGACCAACCAGTGGGAAGAT
GAACTGCGACGTGTGCGGGTTATCCTGCATTAGCTTCAACGTCTTGATGGTTC
ATAAGCGAAGCCATACCGGCGAACGCCCGTTCCAGTGTAATCAGTGCGGGGC
ATCTTTTACTCAGAAAGGTAACCTCCTCCGTCATATTAAACTGCACACGGGGG
AAAAACCTTTTAAGTGTCACCTCTGCAACTACGCATGCCAAAGGAGAGATGC
GCTCACGGGACACCTTAGGACACATTCTGTGGAGAAGCCGTACAAGTGTGAG
TTCTGCGGAAGAAGCTACAAGCAGAGAAGCTCCTGGAGGAGCACAAGGAA
CGCTGCCGAGCTTTTCTTCAGAACCCTGACCTGGGGGACGCTGCAAGTGTGG
AGGCAAGACACATCAAAGCCGAGATGGGAAGTGAGAGAGCTCTCGTCCTGG
ACAGATTAGCAAGCAATGTGGCTAAGCGAAAAAGCTCGATGCCTCAGAAATT
CATCGGTGAGAAGCGGCACTGCTTCGATGCCAACTACAATCCCGGCTACATG
TACGAGAAGGAGAACGAGATGATGCAGACCCGGATGATGGACCAAGCCATC
AATAACGCCATCAGCTATCTAGGGGCTGAAGCCTTCCGCCCCTTAGTCCAGA
CTCCGCCTGCTCCCACCTCTGAGATGGTCCCAGTCATCAGCAGTGTGTACCCC
ATAGCACTTACTCGGGCCGATATGCCAATGGGGGCCCCGCAgGAGATGGAAA
AGAAACGGATCCTCCTGCCAGAGAAGATCTTGCCTTCTGAACGAGGTCTGTC
CCCCAATAACAGTGCCCAGGACTCCACAGACACCGACAGCAACCACGAGGAT
CGCCAACATCTCTACCAGCAAAGCCACGTGGTCCTCCCCCAGGCCCGCAATG
GGATGCCTCTTCTGAAGGAGGTCCCTCGCTCTTTTGAACTCCTCAAGCCCCCT
CCCATCTGCCTGAGGGACTCCATCAAAGTGATCAACAAGAAGGGGAGGTGA
TGGATGTGTTTCGATGTGACCACTGCCACGTCCTCTTCCTAGATTATGTGATG
TTCACCATCCACATGGGGTGCCATGGTTTCCGTGATCCCTTTGAGTGTAACAT
GTGTGGCTATCGAAGCCACGATCGCTATGAGTTCTCCTCTCACATCGCCAGAG
GAGAGCACAGAGCCATGTTGAAGTGAGCATCTGTCCTCAATGCGAGGGTCAA
CATTGTTTTTTAAAGCTGATGGTAGCCTTATCCAGTAGACTGAACTCAAACCC
ACCTCGAG

FIG. 1A

1B. MOUSE AIOLOS PEPTIDE SEQUENCE

MEDIQPTVELKSTEEQPLPTESPDALNDYSLPKPHEIENVDSREAPANEDEDAGED
SMKVKDEYSDRDENIMKPEPMGDAEESEMPYSYAREYSDYESIKLERHVPYDNS
RPTSGKMNCDVCGLSCISFNVLMVHKRSHTGERPFQCNQCGASFTQKGNLLRHI
KLHTGEKPFKCHLCNYACQRRDALTGHLRTHSVEKPYKCEFCGRSYKQRSSLEE
HKERCRAFLQNPDLGDAASVEARHIKAEMGSERALVLDRLASNVAKRKSSMPQ
KFIGEKRHCFDANYNPGYMYEKENEMMQTRMMDQAINNAISYLGAEAFRPLVQ
TPPAPTSEMVPVISSVYPIALTRADMPMGAPQEMEKKRILLPEKILPSERGLSPNN
SAQDSTDTDSNHEDRQHLYQQSHVVLPQARNGMPLLKEVPRSFELLKPPPICLRD
SIKVINKEGEVMDVFRCDHCHVLFLDYVMFTIHMGCHGFRDPFECNMCGYRSH
DRYEFSSHIARGEHRAMLK

FIG. 1B

```
           1                                                          50
    aio    ..........  ..........  ..........  ..........  ..........
    Ik1    MDVDEGQDMS  QVSGKESPPV  SDTPDEGDEP  MPVPEDLSTT  SGAQQNSKSD 51                                                         100
    aio    ..........  ..........  ..........  ..........  ..........
    Ik1    RGMASNVKVE  TQSDEENGRA  CEMNGEECAE  DLRMLDASGE  KMNGSHRDQG
                                                       Ex4
           101                                          ▼             150
    Ik     ..........  NSARGKMNCD  VCGLSCISFN  VLMVHKRTHT  GERPFQCNQC
    Ik1    SSALSGVGGI  RLPNGKLKCD  ICGIVCIGPN  VLMVHKRSHT  GERPFQCNQC
                                                       Ex5
           151                                            ▼200
    aio    GASFTQKGNL  LRHIKLHTGE  KPFKCHLCNY  ACQRRDALTG  HLRTHSVEKP
    Ik1    GASFTQKGNL  LRHIKLHSGE  KPFKCHLCNY  ACRRRDALTG  HLRTHSVGKP
                                              Ex6
           201                                ▼                       250
    Aio    YKCEFCGRSY  KQRSSLEEHK  ERCRAFLQNP  DLGDAASV..  ......EARH
    Ik1    HKCGYCGRSY  KQRSSLEEHK  ERCHNYLESM  GLPGMYPVIK  EETNHNEMAE
                                              Ex7
           251                                ▼                       300
    Aio    IKAEMGSERA  LVLDRLASNV  AKRKSSMPQK  FIGEKRHCFD  ANYNPGYMYE
    Ik1    DLCKIGAERS  LVLDRLASNV  AKRKSSMPQK  FLGDK..CLS  DMPYDSANYE 301                                                        350
    Aio    KENEMMQTRM  MDQ.......  ..........  ..........  ..........
    Ik1    KE.DMMTSHV  MDQ
```

FIG. 3

```
                    Ex7
                     ↓ ────▷ ACTIVATION DOMAIN
             1       ▽                                              50
cAio    PPLLLVPGEK  RHCFDANYNP  GYMYEKENEM  MQTRMMDQAI  NNAISYLGAE
mAio    .......GEK  RHCFDANYNP  GYMYEKENEM  MQTRMMDQAI  NNAISYLGAE
mIka    ........GD  KCLSDMPYDS  .ANYEKE.DM  MTSHVMDQAI  NNAINYLGAE
cIka    ..........  .DRLDLPYDA  TTNYEKENEI  MQTHVIDQAI  NNAISYLGAE

◁─── YAS 5
             51                                                    100
cAio    AVRPLVQTPP  APTSEMVPVI  SSVYPIALTR  AD...MPNGA  PQEMEKKRIL
mAio    AC..LVQTPP  APTSEMVPVI  SSVYPIALTR  AD...MPMGA  PQEMEKKRIL
Chu1    SLRPLVQTPP  G.SSEVVPVI  SSMYQLHKPP  SDGPPRSNHS  AQD.AVDNLL
cIka    SLRPLVQTPP  V.GSEVVPVI  SPMYQLHKPH  GDNQTRSNHT  AQDSAVENLL

YAS 3 ◁──▷
             101                                                   150
cAio    L..PEKILPS  ERGLSPNNSA  QDSTDTDSNH  ED.RQHLYQQ  SHVVLPQARN
mAio    L..PEKILPS  ERGLSPNNSA  QDSTDTDSNH  ED.RQHLYQQ  SHVVLPQARN
mIka    LLSKAKSVSS  EREASPSNSC  QDSTDTESNA  EEQRSGLIYL  TNHINPHARN
cIka    LLSKAKSVSS  ERDASPSNSC  QDSTDTESNN  EE.RSGLIYL  TNHIGPHARN

◁──▷ YIZ
             151                                                   200
cAio    GMPLLKEVPR  SFELLKPPPI  CLRDSIKVIN  KEGEVMDVFR  CDHCHVLFLD
mAio    GMPLLKEVPR  SFELLKPPPI  CLRDSIKVIN  KEGEVMDVFR  CDHCHVLFLD
mIka    GLA.LKEEQR  AYEVLRAASE  NSQDAFRVVS  TSGEQLKVYK  CEHCRVLFLD
cIka    GIS.VKEESR  QFDVLRAGTD  NSQDAFKVIS  SNGEQVRVYK  CEHCRVLFLD

201                                            ◁─┐ 249
cAio    YVMFTIHM.GCHGFRDPF  ECNMCGYRSH  DRYEFSSHIA  RGEHRAMLK
mAio    YVMFTIHM..GCHGFRDPF ECNMCGYRSH  DRYEFSSHIA  RGEHRAMLK
mIka    HVMYTIHM  GCHGFRDPF  ECNMCGYHSQ  DRYEFSSHIT  RGEHRYHLS
cIka    HVMYTIHM.GCHGFRDPF  ECNMCGYHSQ  DRYEFSSHIT  RGEHRFHMS
```

YAS 5 = interaction domain
YAS 3 = interaction domain
YIZ   = Ikaros dimerization domain

FIG. 2

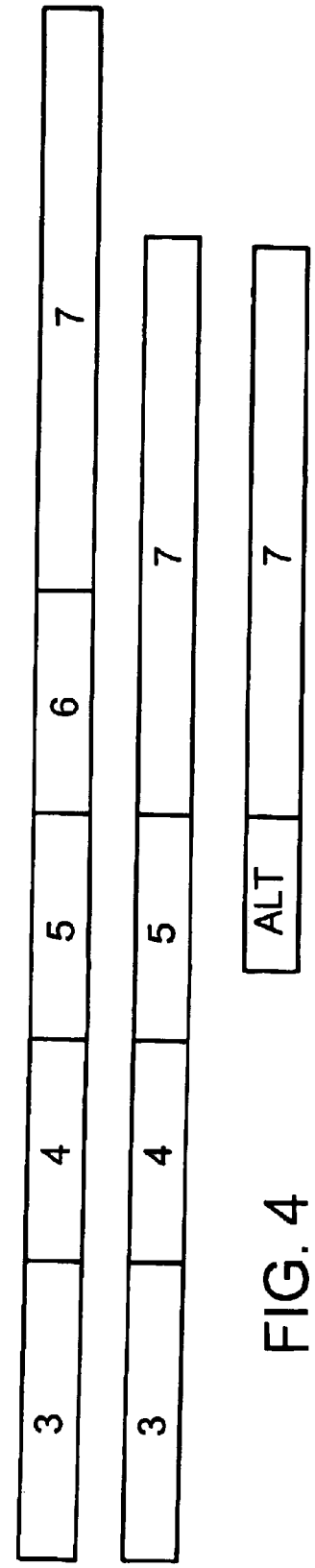

Exon 3
IRHEEAPANEDEDAGEDSMKVKDEYSDRDENIMKPEPMGDAEESEMPYSYA
REYSDYESIKLERHVPYDNSRPTSGKMNCDVCGLSCISFNVLMVHKRSHT Exon 4
GERPFQCNQCGASFTQKGNLLRHIKLHTGEKPFKCHLCNYACQRRDALTGH
LRTHS Exon 5
VEKPYKCEFCGRSYKQRSSLEEHKERCRAFLQNPDLGDA Exon 6
ASVEARHIKAEMGSERALVLDRLASNVAKRKSSMPQKFI Exon 7
GEKRHCFDANYNPGYMYEKENEMMQTRMMDQAINNAISYLGAEAFRPLVQ
TPPAPTSEMVPVISSVYPIALTRADMPMGAPQEMEKKRILLPEKILPSERG
LSPNNSAQDSTDTDSNHEDRQHLYQQSHVVLPQARNGMPLLKEVPRSFEL
LKPPPICLRDSIKVINKEGEVMDVFRCDHCHVLFLDYVMFTIHMGCHGFRD
PFECNMCGYRSHDRYEFSSHIARGEHRAMLK

FIG. 4

```
         10        20        30        40        50        60        70        80        90
         |         |         |         |         |         |         |         |         |
GAAAGAGTTGAGAAAGTTTTAAAGTCAGAAGCCATGGAAACCATTCAGAAGACCATTGCAGAAGCCTTGAATTGCAGAGAGCCTTACAGCTATTCAAGAGAGTATAATGAA  90
TTATGAAAACATTAAGTTGGAGAGACATTGTCTCATTGGATTAGTAGCAGGCCAAGAGTAGCAGGCCAATGCAGTAGAACTGCGATGATGGAAAGATGGCGATGTGTGGATTA  180
TCCTGAATCAGCTTCAAATGCTTAAGATTCTTAAAGGAACAACCATTACTgGtgaacgcccattccagtgtaatcagtgtgggcatcctttt  270
actcagaaggtaacctcctccgccacattaaActgcacacaggggaaaaaccttttaagtgtcacctctgaactatgcatgccaaaga  360
agagatgcgctcagggggcatctcttgtggagaaacctctacaaatgtgagttttttgtggaaggagttacaagcagagaagt  450
         |         |         |         |         |         |         |         |         |
         460       470       480       490       500       510       520       530       540
bccctttgaggagcacaaggagagctgctgccgtacattttcttcagcgactgaccccaggggacacttGCAAGTGCGGAAGACACATCAAA  540
GCAGAGATGGGCGAAGTGCAAGCGCCTCTCCTACTGGACAGATTACCAAGCAATGTGCCAAACGAAAAAGCTCAATGCCTACAGAAATTCA  628

FIG. 5A
```

Lipman-Pearson Protein Alignment
kTuple: 2; Gap Penalty: 4; Gap Length Penalty: 12
Seq1(1>209)
human Aiolos protein AioC/hAio2
Seq2(1>508)
mouseaiolos.protein

| | Similarity Index | Gap Length | Gap Number | Concensus Length |
|---|---|---|---|---|
| (1>209) (66>273) | 89.5 | 1 | 1 | 209 |

```
human Aiolos protein AioC/hAio2    ERDENVLKSEPMGNAEEPEIPYSYSREYNEYENIKLERHVVSFDSSRPTSGKMNCDVCGL  60
                                   :RDEN::K:EPMG:AEE:E:PYSY:REY::YE:IKLERHV::D:SRPTSGKMNCDVCGL
mouseaiolos.protein                DRDENIMKPEPMGDAEESEMPYSYAREYSDYESIKLERHV-PYDNSRPTSGKMNCDVCGL 124 human Aiolos protein AioC/hAio2    SCISFNVLMVHKRSHTGERPFQCNQCGASFTQKGNLLRHIKLHTGEKPFKCHLCNYACQR 120
                                   SCISFNVLMVHKRSHTGERPFQCNQCGASFTQKGNLLRHIKLHTGEKPFKCHLCNYACQR
mouseaiolos.protein                SCISFNVLMVHKRSHTGERPFQCNQCGASFTQKGNLLRHIKLHTGEKPFKCHLCNYACQR 184 human Aiolos protein AioC/hAio2    RDALTGHLRTHSVEKPYKCEFCGRSYKQRSSLEEHKERCRTFLQSTDPGDTASAEARHIK 180
                                   RDALTGHLRTHSVEKPYKCEFCGRSYKQRSSLEEHKERCR:FLQ:.D GD:AS.EARHIK
mouseaiolos.protein                RDALTGHLRTHSVEKPYKCEFCGRSYKQRSSLEEHKERCRAFLQNPDLGDAASVEARHIK 244 human Aiolos protein AioC/hAio2    AEMGSERALVLDRLASNVAKRKSSMPQKF 209
                                   AEMGSERALVLDRLASNVAKRKSSMPQKF
mouseaiolos.protein                AEMGSERALVLDRLASNVAKRKSSMPQKF 273
```

FIG. 5B

```
  1 MEDIQPTVELKSTEEQPLPTESPDRLNDYSLPKPHEIENVDSRERPANED 50
    ::: |.  ::.:.|..|:......:: | .:| |.::....: |..|..
    MDVDEGQDMSQVSGKESPPVSDTPDEG..DEPMPVPEDLSTTSG...RQQNSK 48

51 EDRGEDS KVKDEYSDRDENI KPEP GDREESEMPYSVREYSDYESIK 100
    .| |  .|  .|| |  . :||  ..|  |:.  ..::.  |.:  .  :|  :
 49 SDRGMRS.NVKVETQSDEENGRRCEMNGEECREDLRMLDRSGEKMNGSHR 97

101 LERHVPY...DNSRPTSGKMN DV GLSCISFNVLMV KRS TGERPFQ  147
    :  :.  :.  | ..||:. | :| | : ||: ||||||||||||||||||
 98 DQGSSALSGVGGIRLPNGKLK DI GIVCIGPNVLMV KRS TGERPFQ  147

148 HQ GRSFTQKGNLLR IKL TGEKPFK HL NYACQRRDRLTG LRT SV 197
    || |||||||||||| ||| |.||||| || |||| |||||||. |||||| ||
148 HQ GRSFTQKGNLLR IKL SGEKPFK HL NYACRRRDRLTG LRT SV 197

198 EKPYK EF GRSYKQRSSLEE KER RAFLQNPDLGDRRSV........E 239
    :||.| |::| ||||||||||||| |:.:|:. :|.:...|         |
198 GKPHK GY GRSYKQRSSLEE KER HNYLESMGLPGVCPVIKEETHHNE 247

240 ARHIKREMGSERALVLDRLASNVAKRKSSMPQKFIGEKRHCFDANYNPGY 289
    .  ..:|.||.||||||||||||||||||||||:|:| |:..  .:
248 MREDLCKIGRERSLVLDRLASNVAKRKSSMPQKFLGDK...CLSDMPYDSR 295

290 MYEKENEMMQTRMMDQRINNAISYLGRERFRPLVQTPPRPTSEMVPVISS 339
    |||| :|| .::|||||||||.||||.:||||||:.  |:|||||
296 MYEKE.DMMTSHVMDQRINNAIHYLGRESLRPLVQTPPGS.SEVVPVISS 343

340 VYPIRLTRRDMPM....GRPQEMEKKRILLPEKILPSERGLSPNNSRQDS 385
    :|.:  ...| |         :|.:.::.   :|  ..| :.|||:  ||.||.|||
344 MYQLHKPPSDGPPRSNHSRQDRVDNLLLLSKRKSVSSERERSPSNSCQDS 393

386 TDTDSN.HEDRQHLYQQSHVVLPQRRNGMPLLKEVPRSFELLKPPPICLR 434
    |||:|| .|:| |.  .: : |:|||||:: ||| .|..:|:|:::.
394 TDTESNREEQRSGLIYLTNHINPHARNGLA.LKEEQRAYEVLRRRSENSQ 442

435 DSIKVINKEGEVMDVFR DH HVLFLDYVMFTI HMGC GFRDPFE NM G 481
    |.::|:...||  :.|::||:|||||||.||.:| |||||||||||||| ||||
443 DRFRVVSTSGEQLKVYK EH RVLFLDHVMYTI HMGC GFRDPFE NM G 492

482 YRSHDRYEFSS I ARGE RAMLK 507
    |:|:|||||||||.|||||  |.
493 YHSQDRYEFSS I TRGE RYHLS 518
```

FIG. 6

SEQUENCE LISTING

<160> NUMBER OF SEQ ID NOS: 38

<210> SEQ ID NO 1
<211> LENGTH: 1984
<212> TYPE: DNA
<213> ORGANISM: Mus musculus
<220> FEATURE:
<221> NAME/KEY: CDS
<222> LOCATION: (374)...(1894)

<400> SEQUENCE: 1

```
cacgagcgca caccgctcgg ctctccttgc gacacgccct catcccggt gtttctcaag      60 tagacgtccc gagacggtcg ctgaggcact gtttccacgc gatcagggtt cctcaggctt     120
gacattcaaa agtgggtgcg gaacccgcgg cactcggagc gtgctttaaa gcggccgcca     180
gccagcgccc ctctaacctc gcgccccggc tgccggcggc tcccgccctg catctgcgcc     240
gacgcgaccg agcgatcccg gggcctccct gcgcccggaa tctcccgcca gccgcgcggg     300
tccccacggc agcagcacgt ggagcggccg cggagcctga gcgacagctg cagcccgcgc     360
ggcccgcggc gac atg gaa gat ata caa ccg act gtg gag ctg aaa agc      409
            Met Glu Asp Ile Gln Pro Thr Val Glu Leu Lys Ser
              1               5                  10 acg gag gag cag cct ctg ccc aca gag agc cca gac gct ctg aat gac      457
Thr Glu Glu Gln Pro Leu Pro Thr Glu Ser Pro Asp Ala Leu Asn Asp
            15                  20                  25 tac agc ttg ccc aaa cct cat gag ata gaa aac gtg gac agt aga gaa      505
Tyr Ser Leu Pro Lys Pro His Glu Ile Glu Asn Val Asp Ser Arg Glu
        30                  35                  40 gcc cca gcc aat gaa gac gaa gat gca gga gaa gat tcg atg aaa gtg      553
Ala Pro Ala Asn Glu Asp Glu Asp Ala Gly Glu Asp Ser Met Lys Val
    45                  50                  55                  60 aaa gat gaa tac agc gac aga gat gag aac att atg aag ccg gag ccc      601
Lys Asp Glu Tyr Ser Asp Arg Asp Glu Asn Ile Met Lys Pro Glu Pro
                65                  70                  75 atg gga gat gca gaa gag agt gaa atg cct tac agc tat gca aga gaa      649
Met Gly Asp Ala Glu Glu Ser Glu Met Pro Tyr Ser Tyr Ala Arg Glu
            80                  85                  90 tac agc gac tat gaa agc att aag ctg gag aga cac gtg ccc tat gac      697
Tyr Ser Asp Tyr Glu Ser Ile Lys Leu Glu Arg His Val Pro Tyr Asp
        95                  100                 105 aac agc aga cca acc agt ggg aag atg aac tgc gac gtg tgc ggg tta      745
Asn Ser Arg Pro Thr Ser Gly Lys Met Asn Cys Asp Val Cys Gly Leu
    110                 115                 120 tcc tgc att agc ttc aac gtc ttg atg gtt cat aag cga agc cat acc      793
Ser Cys Ile Ser Phe Asn Val Leu Met Val His Lys Arg Ser His Thr
125                 130                 135                 140 ggc gaa cgc ccg ttc cag tgt aat cag tgc ggg gca tct ttt act cag      841
Gly Glu Arg Pro Phe Gln Cys Asn Gln Cys Gly Ala Ser Phe Thr Gln
                145                 150                 155 aaa ggt aac ctc ctc cgt cat att aaa ctg cac acg ggg gaa aaa cct      889
```

-continued

```
            Lys Gly Asn Leu Leu Arg His Ile Lys Leu His Thr Gly Glu Lys Pro
                            160                 165                 170 ttt aag tgt cac ctc tgc aac tac gca tgc caa agg aga gat gcg ctc        937
Phe Lys Cys His Leu Cys Asn Tyr Ala Cys Gln Arg Arg Asp Ala Leu
        175                 180                 185 acg gga cac ctt agg aca cat tct gtg gag aag ccg tac aag tgt gag        985
Thr Gly His Leu Arg Thr His Ser Val Glu Lys Pro Tyr Lys Cys Glu
    190                 195                 200 ttc tgc gga aga agc tac aag cag aga agc tcc ctg gag gag cac aag       1033
Phe Cys Gly Arg Ser Tyr Lys Gln Arg Ser Ser Leu Glu Glu His Lys
205                 210                 215                 220 gaa cgc tgc cga gct ttt ctt cag aac cct gac ctg ggg gac gct gca       1081
Glu Arg Cys Arg Ala Phe Leu Gln Asn Pro Asp Leu Gly Asp Ala Ala
                225                 230                 235 agt gtg gag gca aga cac atc aaa gcc gag atg gga agt gag aga gct       1129
Ser Val Glu Ala Arg His Ile Lys Ala Glu Met Gly Ser Glu Arg Ala
            240                 245                 250 ctc gtc ctg gac aga tta gca agc aat gtg gct aag cga aaa agc tcg       1177
Leu Val Leu Asp Arg Leu Ala Ser Asn Val Ala Lys Arg Lys Ser Ser
        255                 260                 265 atg cct cag aaa ttc atc ggt gag aag cgg cac tgc ttc gat gcc aac       1225
Met Pro Gln Lys Phe Ile Gly Glu Lys Arg His Cys Phe Asp Ala Asn
    270                 275                 280 tac aat ccc ggc tac atg tac gag aag gag aac gag atg atg cag acc       1273
Tyr Asn Pro Gly Tyr Met Tyr Glu Lys Glu Asn Glu Met Met Gln Thr
285                 290                 295                 300 cgg atg atg gac caa gcc atc aat aac gcc atc agc tat cta ggg gct       1321
Arg Met Met Asp Gln Ala Ile Asn Asn Ala Ile Ser Tyr Leu Gly Ala
                305                 310                 315 gaa gcc ttc cgc ccc tta gtc cag act ccg cct gct ccc acc tct gag       1369
Glu Ala Phe Arg Pro Leu Val Gln Thr Pro Pro Ala Pro Thr Ser Glu
            320                 325                 330 atg gtc cca gtc atc agc agt gtg tac ccc ata gca ctt act cgg gcc       1417
Met Val Pro Val Ile Ser Ser Val Tyr Pro Ile Ala Leu Thr Arg Ala
        335                 340                 345 gat atg cca atg ggg gcc ccg cag gag atg gaa aag aaa cgg atc ctc       1465
Asp Met Pro Met Gly Ala Pro Gln Glu Met Glu Lys Lys Arg Ile Leu
    350                 355                 360 ctg cca gag aag atc ttg cct tct gaa cga ggt ctg tcc ccc aat aac       1513
Leu Pro Glu Lys Ile Leu Pro Ser Glu Arg Gly Leu Ser Pro Asn Asn
365                 370                 375                 380 agt gcc cag gac tcc aca gac acc gac agc aac cac gag gat cgc caa       1561
Ser Ala Gln Asp Ser Thr Asp Thr Asp Ser Asn His Glu Asp Arg Gln
                385                 390                 395 cat ctc tac cag caa agc cac gtg gtc ctc ccc cag gcc cgc aat ggg       1609
His Leu Tyr Gln Gln Ser His Val Val Leu Pro Gln Ala Arg Asn Gly
            400                 405                 410 atg cct ctt ctg aag gag gtc cct cgc tct ttt gaa ctc ctc aag ccc       1657
Met Pro Leu Leu Lys Glu Val Pro Arg Ser Phe Glu Leu Leu Lys Pro
        415                 420                 425 cct ccc atc tgc ctg agg gac tcc atc aaa gtg atc aac aaa gaa ggg       1705
Pro Pro Ile Cys Leu Arg Asp Ser Ile Lys Val Ile Asn Lys Glu Gly
    430                 435                 440 gag gtg atg gat gtg ttt cga tgt gac cac tgc cac gtc ctc ttc cta       1753
Glu Val Met Asp Val Phe Arg Cys Asp His Cys His Val Leu Phe Leu
445                 450                 455                 460 gat tat gtg atg ttc acc atc cac atg ggg tgc cat ggt ttc cgt gat       1801
Asp Tyr Val Met Phe Thr Ile His Met Gly Cys His Gly Phe Arg Asp
                465                 470                 475
```

-continued

```
ccc ttt gag tgt aac atg tgt ggc tat cga agc cac gat cgc tat gag      1849
Pro Phe Glu Cys Asn Met Cys Gly Tyr Arg Ser His Asp Arg Tyr Glu
            480                 485                 490 ttc tcc tct cac atc gcc aga gga gag cac aga gcc atg ttg aag          1894
Phe Ser Ser His Ile Ala Arg Gly Glu His Arg Ala Met Leu Lys
        495                 500                 505 tgagcatctg tcctcaatgc gagggtcaac attgttttt  aaagctgatg gtagccttat    1954
ccagtagact gaactcaaac ccacctcgag                                     1984

<210> SEQ ID NO 2
<211> LENGTH: 507
<212> TYPE: PRT
<213> ORGANISM: Mus musculus

<400> SEQUENCE: 2

Met Glu Asp Ile Gln Pro Thr Val Glu Leu Lys Ser Thr Glu Glu Gln
  1               5                  10                  15

Pro Leu Pro Thr Glu Ser Pro Asp Ala Leu Asn Asp Tyr Ser Leu Pro
             20                  25                  30

Lys Pro His Glu Ile Glu Asn Val Asp Ser Arg Glu Ala Pro Ala Asn
         35                  40                  45

Glu Asp Glu Asp Ala Gly Glu Asp Ser Met Lys Val Lys Asp Glu Tyr
     50                  55                  60

Ser Asp Arg Asp Glu Asn Ile Met Lys Pro Glu Pro Met Gly Asp Ala
 65                  70                  75                  80

Glu Glu Ser Glu Met Pro Tyr Ser Tyr Ala Arg Glu Tyr Ser Asp Tyr
                 85                  90                  95

Glu Ser Ile Lys Leu Glu Arg His Val Pro Tyr Asp Asn Ser Arg Pro
            100                 105                 110

Thr Ser Gly Lys Met Asn Cys Asp Val Cys Gly Leu Ser Cys Ile Ser
        115                 120                 125

Phe Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Thr Gly Glu Lys Pro Phe Lys Cys His
                165                 170                 175

Leu Cys Asn Tyr Ala Cys Gln Arg Arg Asp Ala Leu Thr Gly His Leu
            180                 185                 190

Arg Thr His Ser Val Glu Lys Pro Tyr Lys Cys Glu Phe Cys Gly Arg
        195                 200                 205

Ser Tyr Lys Gln Arg Ser Ser Leu Glu Glu His Lys Glu Arg Cys Arg
    210                 215                 220

Ala Phe Leu Gln Asn Pro Asp Leu Gly Asp Ala Ala Ser Val Glu Ala
225                 230                 235                 240

Arg His Ile Lys Ala Glu Met Gly Ser Glu Arg Ala Leu Val Leu Asp
                245                 250                 255

Arg Leu Ala Ser Asn Val Ala Lys Arg Lys Ser Ser Met Pro Gln Lys
            260                 265                 270

Phe Ile Gly Glu Lys Arg His Cys Phe Asp Ala Asn Tyr Asn Pro Gly
        275                 280                 285

Tyr Met Tyr Glu Lys Glu Asn Glu Met Met Gln Thr Arg Met Met Asp
    290                 295                 300

Gln Ala Ile Asn Asn Ala Ile Ser Tyr Leu Gly Ala Glu Ala Phe Arg
305                 310                 315                 320
```

```
Pro Leu Val Gln Thr Pro Pro Ala Pro Thr Ser Glu Met Val Pro Val
            325                 330                 335

Ile Ser Ser Val Tyr Pro Ile Ala Leu Thr Arg Ala Asp Met Pro Met
            340                 345                 350

Gly Ala Pro Gln Glu Met Glu Lys Lys Arg Ile Leu Leu Pro Glu Lys
            355                 360                 365

Ile Leu Pro Ser Glu Arg Gly Leu Ser Pro Asn Asn Ser Ala Gln Asp
        370                 375                 380

Ser Thr Asp Thr Asp Ser Asn His Glu Asp Arg Gln His Leu Tyr Gln
385                 390                 395                 400

Gln Ser His Val Val Leu Pro Gln Ala Arg Asn Gly Met Pro Leu Leu
            405                 410                 415

Lys Glu Val Pro Arg Ser Phe Glu Leu Leu Lys Pro Pro Pro Ile Cys
            420                 425                 430

Leu Arg Asp Ser Ile Lys Val Ile Asn Lys Glu Gly Glu Val Met Asp
        435                 440                 445

Val Phe Arg Cys Asp His Cys His Val Leu Phe Leu Asp Tyr Val Met
450                 455                 460

Phe Thr Ile His Met Gly Cys His Gly Phe Arg Asp Pro Phe Glu Cys
465                 470                 475                 480

Asn Met Cys Gly Tyr Arg Ser His Asp Arg Tyr Glu Phe Ser Ser His
            485                 490                 495

Ile Ala Arg Gly Glu His Arg Ala Met Leu Lys
            500                 505

<210> SEQ ID NO 3
<211> LENGTH: 23
<212> TYPE: DNA
<213> ORGANISM: Artificial Sequence
<220> FEATURE:
<223> OTHER INFORMATION: primer for PCR

<400> SEQUENCE: 3
tayaccatyc acatgggctr cca                                        23

<210> SEQ ID NO 4
<211> LENGTH: 21
<212> TYPE: DNA
<213> ORGANISM: Artificial Sequence
<220> FEATURE:
<223> OTHER INFORMATION: primer for PCR

<400> SEQUENCE: 4
rccrcacatg ttrcactyra a                                          21

<210> SEQ ID NO 5
<211> LENGTH: 24
<212> TYPE: DNA
<213> ORGANISM: Artificial Sequence
<220> FEATURE:
<223> OTHER INFORMATION: primer for PCR

<400> SEQUENCE: 5
gtgtgcgggt tatcctgcat tagc                                       24

<210> SEQ ID NO 6
<211> LENGTH: 24
<212> TYPE: DNA
<213> ORGANISM: Artificial Sequence
<220> FEATURE:
```

<223> OTHER INFORMATION: primer for PCR

<400> SEQUENCE: 6
atcgaagcag tgccgcttct cacc                                            24

<210> SEQ ID NO 7
<211> LENGTH: 628
<212> TYPE: DNA
<213> ORGANISM: Homo sapiens
<220> FEATURE:
<221> NAME/KEY: CDS
<222> LOCATION: (1)...(627)

<400> SEQUENCE: 7

```
gaa aga gat gag aat gtt tta aag tca gaa ccc atg gga aat gca gaa       48
Glu Arg Asp Glu Asn Val Leu Lys Ser Glu Pro Met Gly Asn Ala Glu
 1               5                  10                  15 gag cct gaa atc cct tac agc tat tca aga gaa tat aat gaa tat gaa       96
Glu Pro Glu Ile Pro Tyr Ser Tyr Ser Arg Glu Tyr Asn Glu Tyr Glu
             20                  25                  30 aac att aag ttg gag aga cat gtt gtc tca ttc gat agt agc agg cca      144
Asn Ile Lys Leu Glu Arg His Val Val Ser Phe Asp Ser Ser Arg Pro
         35                  40                  45 acc agt gga aag atg aac tgc gat gtg tgt gga tta tcc tgc atc agc      192
Thr Ser Gly Lys Met Asn Cys Asp Val Cys Gly Leu Ser Cys Ile Ser
     50                  55                  60 ttc aat gtc tta atg gtt cat aag cga agc cat act ggt gaa cgc cca      240
Phe Asn Val Leu Met Val His Lys Arg Ser His Thr Gly Glu Arg Pro
 65                  70                  75                  80 ttc cag tgt aat cag tgt ggg gca tct ttt act cag aaa ggt aac ctc      288
Phe Gln Cys Asn Gln Cys Gly Ala Ser Phe Thr Gln Lys Gly Asn Leu
                 85                  90                  95 ctc cgc cac att aaa ctg cac aca ggg gaa aaa cct ttt aag tgt cac      336
Leu Arg His Ile Lys Leu His Thr Gly Glu Lys Pro Phe Lys Cys His
            100                 105                 110 ctc tgc aac tat gca tgc caa aga aga gat gcg ctc acg ggg cat ctt      384
Leu Cys Asn Tyr Ala Cys Gln Arg Arg Asp Ala Leu Thr Gly His Leu
        115                 120                 125 agg aca cat tct gtg gag aaa ccc tac aaa tgt gag ttt tgt gga agg      432
Arg Thr His Ser Val Glu Lys Pro Tyr Lys Cys Glu Phe Cys Gly Arg
    130                 135                 140 agt tac aag cag aga agt tcc ctt gag gag cac aag gag cgc tgc cgt      480
Ser Tyr Lys Gln Arg Ser Ser Leu Glu Glu His Lys Glu Arg Cys Arg
145                 150                 155                 160 aca ttt ctt cag agc act gac cca ggg gac act gca agt gcg gag gca      528
Thr Phe Leu Gln Ser Thr Asp Pro Gly Asp Thr Ala Ser Ala Glu Ala
                165                 170                 175 aga cac atc aaa gca gag atg gga agt gaa aga gct ctc gta ctg gac      576
Arg His Ile Lys Ala Glu Met Gly Ser Glu Arg Ala Leu Val Leu Asp
            180                 185                 190 aga tta gca agc aat gtg gca aaa cga aaa agc tca atg cct cag aaa      624
Arg Leu Ala Ser Asn Val Ala Lys Arg Lys Ser Ser Met Pro Gln Lys
        195                 200                 205 ttc a                                                                628
Phe
```

<210> SEQ ID NO 8
<211> LENGTH: 209
<212> TYPE: PRT
<213> ORGANISM: Homo sapiens

<400> SEQUENCE: 8

```
Glu Arg Asp Glu Asn Val Leu Lys Ser Glu Pro Met Gly Asn Ala Glu
  1               5                  10                 15

Glu Pro Glu Ile Pro Tyr Ser Tyr Ser Arg Glu Tyr Asn Glu Tyr Glu
                20                  25                 30

Asn Ile Lys Leu Glu Arg His Val Val Ser Phe Asp Ser Ser Arg Pro
             35                  40                  45

Thr Ser Gly Lys Met Asn Cys Asp Val Cys Gly Leu Ser Cys Ile Ser
         50                  55                  60

Phe Asn Val Leu Met Val His Lys Arg Ser His Thr Gly Glu Arg Pro
 65              70                  75                  80

Phe Gln Cys Asn Gln Cys Gly Ala Ser Phe Thr Gln Lys Gly Asn Leu
             85                  90                  95

Leu Arg His Ile Lys Leu His Thr Gly Glu Lys Pro Phe Lys Cys His
             100                 105                 110

Leu Cys Asn Tyr Ala Cys Gln Arg Arg Asp Ala Leu Thr Gly His Leu
             115                 120                 125

Arg Thr His Ser Val Glu Lys Pro Tyr Lys Cys Glu Phe Cys Gly Arg
         130                 135                 140

Ser Tyr Lys Gln Arg Ser Ser Leu Glu Glu His Lys Glu Arg Cys Arg
145                 150                 155                 160

Thr Phe Leu Gln Ser Thr Asp Pro Gly Asp Thr Ala Ser Ala Glu Ala
                 165                 170                 175

Arg His Ile Lys Ala Glu Met Gly Ser Glu Arg Ala Leu Val Leu Asp
                 180                 185                 190

Arg Leu Ala Ser Asn Val Ala Lys Arg Lys Ser Ser Met Pro Gln Lys
             195                 200                 205

Phe

<210> SEQ ID NO 9
<211> LENGTH: 24
<212> TYPE: DNA
<213> ORGANISM: Artificial Sequence
<220> FEATURE:
<223> OTHER INFORMATION: primer for PCR

<400> SEQUENCE: 9
gtaacctcct ccgtcatatt aaac                                    24

<210> SEQ ID NO 10
<211> LENGTH: 24
<212> TYPE: DNA
<213> ORGANISM: Artificial Sequence
<220> FEATURE:
<223> OTHER INFORMATION: primer for PCR

<400> SEQUENCE: 10
cgagcttttc ttcagaaccc tgac                                    24

<210> SEQ ID NO 11
<211> LENGTH: 24
<212> TYPE: DNA
<213> ORGANISM: Artificial Sequence
<220> FEATURE:
<223> OTHER INFORMATION: probe for EMSA

<400> SEQUENCE: 11
tcagcttttg ggataccct gtca                                     24
```

```
<210> SEQ ID NO 12
<211> LENGTH: 24
<212> TYPE: DNA
<213> ORGANISM: Artificial Sequence
<220> FEATURE:
<223> OTHER INFORMATION: probe for EMSA

<400> SEQUENCE: 12
tcagcttttg ggggtaccct gtca                                          24

<210> SEQ ID NO 13
<211> LENGTH: 30
<212> TYPE: DNA
<213> ORGANISM: Artificial Sequence
<220> FEATURE:
<223> OTHER INFORMATION: primer for PCR

<400> SEQUENCE: 13
atggtgaagg tcggtgtgaa cggatttggc                                    30

<210> SEQ ID NO 14
<211> LENGTH: 30
<212> TYPE: DNA
<213> ORGANISM: Artificial Sequence
<220> FEATURE:
<223> OTHER INFORMATION: primer for PCR

<400> SEQUENCE: 14
gcatcgaagg tggaagagtg ggagttgctg                                    30

<210> SEQ ID NO 15
<211> LENGTH: 1788
<212> TYPE: DNA
<213> ORGANISM: Mus musculus
<220> FEATURE:
<221> NAME/KEY: CDS
<222> LOCATION: (223)...(1515)

<400> SEQUENCE: 15
aattcgttct accttctctg aaccccagtg gtgtgtcaag gccggactgg gagcttgggg   60
gaagaggaag aggaagagga atctgcggct catccaggga tcagggtcct tcccaagtgg  120
ccactcagag gggactcaga gcaagtctag atttgtgtgg cagagagaga cagctctcgt  180
ttggccttgg ggaggcacaa gtctgttgat aacctgaaga ca atg gat gtc gat    234
                                                Met Asp Val Asp
                                                 1 gag ggt caa gac atg tcc caa gtt tca gga aag gag agc ccc cca gtc    282
Glu Gly Gln Asp Met Ser Gln Val Ser Gly Lys Glu Ser Pro Pro Val
 5                  10                  15                  20 agt gac act cca gat gaa ggg gat gag ccc atg cct gtc cct gag gac    330
Ser Asp Thr Pro Asp Glu Gly Asp Glu Pro Met Pro Val Pro Glu Asp
                 25                  30                  35 ctg tcc act acc tct gga gca cag cag aac tcc aag agt gat cga ggc    378
Leu Ser Thr Thr Ser Gly Ala Gln Gln Asn Ser Lys Ser Asp Arg Gly
             40                  45                  50 atg ggt gaa cgg cct ttc cag tgc aac cag tct ggg gcc tcc ttt acc    426
Met Gly Glu Arg Pro Phe Gln Cys Asn Gln Ser Gly Ala Ser Phe Thr
         55                  60                  65 cag aaa ggc aac ctc ctg cgg cac atc aag ctg cac tcg ggt gag aag    474
Gln Lys Gly Asn Leu Leu Arg His Ile Lys Leu His Ser Gly Glu Lys
 70                  75                  80 ccc ttc aaa tgc cat ctt tgc aac tat gcc tgc cgc cgg agg gac gcc    522
Pro Phe Lys Cys His Leu Cys Asn Tyr Ala Cys Arg Arg Arg Asp Ala
 85                  90                  95                 100
```

```
ctc acc ggc cac ctg agg acg cac tcc gtt ggt aag cct cac aaa tgt      570
Leu Thr Gly His Leu Arg Thr His Ser Val Gly Lys Pro His Lys Cys
            105                 110                 115 gga tat tgt ggc cgg agc tat aaa cag cga agc tct tta gag gag cat      618
Gly Tyr Cys Gly Arg Ser Tyr Lys Gln Arg Ser Ser Leu Glu Glu His
        120                 125                 130 aaa gag cga tgc cac aac tac ttg gaa agc atg ggc ctt ccg ggc gtg      666
Lys Glu Arg Cys His Asn Tyr Leu Glu Ser Met Gly Leu Pro Gly Val
            135                 140                 145 tgc cca gtc att aag gaa gaa act aac cac aac gag atg gca gaa gac      714
Cys Pro Val Ile Lys Glu Glu Thr Asn His Asn Glu Met Ala Glu Asp
150                 155                 160 ctg tgc aag ata gga gca gag agg tcc ctt gtc ctg gac agg ctg gca      762
Leu Cys Lys Ile Gly Ala Glu Arg Ser Leu Val Leu Asp Arg Leu Ala
165                 170                 175                 180 agc aat gtc gcc aaa cgt aag agc tct atg cct cag aaa ttt ctt gga      810
Ser Asn Val Ala Lys Arg Lys Ser Ser Met Pro Gln Lys Phe Leu Gly
                185                 190                 195 gac aag tgc ctg tca gac atg ccc tat gac agt gcc aac tat gag aag      858
Asp Lys Cys Leu Ser Asp Met Pro Tyr Asp Ser Ala Asn Tyr Glu Lys
            200                 205                 210 gag gat atg atg aca tcc cac gtg atg gac cag gcc atc aac aat gcc      906
Glu Asp Met Met Thr Ser His Val Met Asp Gln Ala Ile Asn Asn Ala
        215                 220                 225 atc aac tac ctg ggg gct gag tcc ctg cgc cca ttg gtg cag aca ccc      954
Ile Asn Tyr Leu Gly Ala Glu Ser Leu Arg Pro Leu Val Gln Thr Pro
            230                 235                 240 ccc ggt agc tcc gag gtg gtg cca gtc atc agc tcc atg tac cag ctg     1002
Pro Gly Ser Ser Glu Val Val Pro Val Ile Ser Ser Met Tyr Gln Leu
245                 250                 255                 260 cac aag ccc ccc tca gat ggc ccc cca cgg tcc aac cat tca gca cag     1050
His Lys Pro Pro Ser Asp Gly Pro Pro Arg Ser Asn His Ser Ala Gln
                265                 270                 275 gac gcc gtg gat aac ttg ctg ctg ctg tcc aag gcc aag tct gtg tca     1098
Asp Ala Val Asp Asn Leu Leu Leu Leu Ser Lys Ala Lys Ser Val Ser
            280                 285                 290 tcg gag cga gag gcc tcc ccg agc aac agc tgc caa gac tcc aca gat     1146
Ser Glu Arg Glu Ala Ser Pro Ser Asn Ser Cys Gln Asp Ser Thr Asp
        295                 300                 305 aca gag agc aac gcg gag gaa cag cgc agc ggc ctt atc tac cta acc     1194
Thr Glu Ser Asn Ala Glu Glu Gln Arg Ser Gly Leu Ile Tyr Leu Thr
            310                 315                 320 aac cac atc aac ccg cat gca cgc aat ggg ctg gct ctc aag gag gag     1242
Asn His Ile Asn Pro His Ala Arg Asn Gly Leu Ala Leu Lys Glu Glu
325                 330                 335                 340 cag cgc gcc tac gag gtg ctg agg gcg gcc tca gag aac tcg cag gat     1290
Gln Arg Ala Tyr Glu Val Leu Arg Ala Ala Ser Glu Asn Ser Gln Asp
                345                 350                 355 gcc ttc cgt gtg gtc agc acg agt ggc gag cag ctg aag gtg tac aag     1338
Ala Phe Arg Val Val Ser Thr Ser Gly Glu Gln Leu Lys Val Tyr Lys
            360                 365                 370 tgc gaa cac tgc cgc gtg ctc ttc ctg gat cac gtc atg tat acc att     1386
Cys Glu His Cys Arg Val Leu Phe Leu Asp His Val Met Tyr Thr Ile
        375                 380                 385 cac atg ggc tgc cat ggc tgc cat ggc ttt cgg gat ccc ttt gag tgt     1434
His Met Gly Cys His Gly Cys His Gly Phe Arg Asp Pro Phe Glu Cys
            390                 395                 400 aac atg tgt ggt tat cac agc cag gac agg tac gag ttc tca tcc cat     1482
Asn Met Cys Gly Tyr His Ser Gln Asp Arg Tyr Glu Phe Ser Ser His
```

```
                405                 410                 415                 420
atc acg cgg ggg gag cat cgt tac cac ctg agc taaacccagc caggccccac            1535
Ile Thr Arg Gly Glu His Arg Tyr His Leu Ser
                    425                 430 tgaagcacaa agatagctgg ttatgcctcc ttcccggcag ctggacccac agcggacaat            1595
gtgggagtgg atttgcaggc agcatttgtt cttttatgtt ggttgtttgg cgtttcattt            1655
gcgttggaag ataagttttt aatgttagtg acaggattgc attgcatcag caacattcac            1715
aacatccatc cttctagcca gttttgttca ctggtagctg aggtttcccg gatatgtggc            1775
ttcctaacac tct                                                              1788

<210> SEQ ID NO 16
<211> LENGTH: 1386
<212> TYPE: DNA
<213> ORGANISM: Homo sapiens
<220> FEATURE:
<221> NAME/KEY: CDS
<222> LOCATION: (1)...(1383)

<400> SEQUENCE: 16 aat gtt aaa gta gag act cag agt gat gaa gag aat ggg cgt gcc tgt             48
Asn Val Lys Val Glu Thr Gln Ser Asp Glu Glu Asn Gly Arg Ala Cys
 1               5                  10                  15 gaa atg aat ggg gaa gaa tgt gcg gag gat tta cga atg ctt gat gcc             96
Glu Met Asn Gly Glu Glu Cys Ala Glu Asp Leu Arg Met Leu Asp Ala
                20                  25                  30 tcg gga gag aaa atg aat ggc tcc cac agg gac caa ggc agc tcg gct            144
Ser Gly Glu Lys Met Asn Gly Ser His Arg Asp Gln Gly Ser Ser Ala
            35                  40                  45 ttg tcg gga gtt gga ggc att cga ctt cct aac gga aaa cta aag tgt            192
Leu Ser Gly Val Gly Gly Ile Arg Leu Pro Asn Gly Lys Leu Lys Cys
        50                  55                  60 gat atc tgt ggg atc att tgc atc ggg ccc aat gtg ctc atg gtt cac            240
Asp Ile Cys Gly Ile Ile Cys Ile Gly Pro Asn Val Leu Met Val His
 65                  70                  75                  80 aaa aga agc cac act gga gaa cgg ccc ttc cag tgc aat cag tgc ggg            288
Lys Arg Ser His Thr Gly Glu Arg Pro Phe Gln Cys Asn Gln Cys Gly
                85                  90                  95 gcc tca ttc acc cag aag ggc aac ctg ctc cgg cac atc aag ctg cat            336
Ala Ser Phe Thr Gln Lys Gly Asn Leu Leu Arg His Ile Lys Leu His
                100                 105                 110 tcc ggg gag aag ccc ttc aaa tgc cac ctc tgc aac tac gcc tgc cgc            384
Ser Gly Glu Lys Pro Phe Lys Cys His Leu Cys Asn Tyr Ala Cys Arg
            115                 120                 125 cgg agg gac gcc ctc act ggc cac ctg agg acg cac tcc gtt ggt aaa            432
Arg Arg Asp Ala Leu Thr Gly His Leu Arg Thr His Ser Val Gly Lys
        130                 135                 140 cct cac aaa tgt gga tat tgt ggc cga agc tat aaa cag cga acg tct            480
Pro His Lys Cys Gly Tyr Cys Gly Arg Ser Tyr Lys Gln Arg Thr Ser
145                 150                 155                 160 tta gag gaa cat aaa gag cgc tgc cac aac tac ttg gaa agc atg ggc            528
Leu Glu Glu His Lys Glu Arg Cys His Asn Tyr Leu Glu Ser Met Gly
                165                 170                 175 ctt ccg ggc aca ctg tac cca gtc att aaa gaa gaa act aag cac agt            576
Leu Pro Gly Thr Leu Tyr Pro Val Ile Lys Glu Glu Thr Lys His Ser
                180                 185                 190 gaa atg gca gaa gac ctg tgc aag ata gga tca gag aga tct ctc gtg            624
Glu Met Ala Glu Asp Leu Cys Lys Ile Gly Ser Glu Arg Ser Leu Val
            195                 200                 205
```

```
ctg gac aga cta gca agt aat gtc gcc aaa cgt aag agc tct atg cct       672
Leu Asp Arg Leu Ala Ser Asn Val Ala Lys Arg Lys Ser Ser Met Pro
    210             215                 220 cag aaa ttt ctt ggg gac aag ggc ctg tcc gac acg ccc tac gac agt       720
Gln Lys Phe Leu Gly Asp Lys Gly Leu Ser Asp Thr Pro Tyr Asp Ser
225                 230                 235                 240 gcc acg tac gag aag gag aac gaa atg atg aag tcc cac gtg atg gac       768
Ala Thr Tyr Glu Lys Glu Asn Glu Met Met Lys Ser His Val Met Asp
                245                 250                 255 caa gcc atc aac aac gcc atc aac tac ctg ggg gcc gag tcc ctg cgc       816
Gln Ala Ile Asn Asn Ala Ile Asn Tyr Leu Gly Ala Glu Ser Leu Arg
            260                 265                 270 ccg ctg gtg cag acg ccc ccg ggc ggt tcc gag gtg gtc ccg gtc atc       864
Pro Leu Val Gln Thr Pro Pro Gly Gly Ser Glu Val Val Pro Val Ile
        275                 280                 285 agc ccg atg tac cag ctg cac agg cgc tcg gag ggc acc ccg cgc tcc       912
Ser Pro Met Tyr Gln Leu His Arg Arg Ser Glu Gly Thr Pro Arg Ser
290                 295                 300 aac cac tcg gcc cag gac agc gcc gtg gag tac ctg ctg ctc tcc           960
Asn His Ser Ala Gln Asp Ser Ala Val Glu Tyr Leu Leu Leu Leu Ser
305                 310                 315                 320 aag gcc aag ttg gtg ccc tcg gag cgc gag gcg tcc ccg agc aac agc      1008
Lys Ala Lys Leu Val Pro Ser Glu Arg Glu Ala Ser Pro Ser Asn Ser
                325                 330                 335 tgc caa gac tcc acg gac acc gag agc aac aac gag gag cag cgc agc      1056
Cys Gln Asp Ser Thr Asp Thr Glu Ser Asn Asn Glu Glu Gln Arg Ser
            340                 345                 350 ggt ctt atc tac ctg acc aac cac atc gcc cga cgc gcg caa cgc gtg      1104
Gly Leu Ile Tyr Leu Thr Asn His Ile Ala Arg Arg Ala Gln Arg Val
        355                 360                 365 tcg ctc aag gag gag cac cgc gcc tac gac ctg ctg cgc gcc gcc tcc      1152
Ser Leu Lys Glu Glu His Arg Ala Tyr Asp Leu Leu Arg Ala Ala Ser
370                 375                 380 gag aac tcg cag gac gcg ctc cgc gtg gtc agc acc agc ggg gag cag      1200
Glu Asn Ser Gln Asp Ala Leu Arg Val Val Ser Thr Ser Gly Glu Gln
385                 390                 395                 400 atg aag gtg tac aag tgc gaa cac tgc cgg gtg ctc ttc ctg gat cac      1248
Met Lys Val Tyr Lys Cys Glu His Cys Arg Val Leu Phe Leu Asp His
                405                 410                 415 gtc atg tac acc atc cac atg ggc tgc cac ggc ttc cgt gat cct ttt      1296
Val Met Tyr Thr Ile His Met Gly Cys His Gly Phe Arg Asp Pro Phe
            420                 425                 430 gag tgc aac atg tgc ggc tac cac agc cag gac cgg tac gag ttc tcg      1344
Glu Cys Asn Met Cys Gly Tyr His Ser Gln Asp Arg Tyr Glu Phe Ser
        435                 440                 445 tcg cac ata acg cga ggg gag cac cgc ttc cac atg agc taa              1386
Ser His Ile Thr Arg Gly Glu His Arg Phe His Met Ser
            450                 455                 460

<210> SEQ ID NO 17
<211> LENGTH: 1296
<212> TYPE: DNA
<213> ORGANISM: Mus musculus
<220> FEATURE:
<221> NAME/KEY: CDS
<222> LOCATION: (1)...(1296)

<400> SEQUENCE: 17 atg gat gtc gat gag ggt caa gac atg tcc caa gtt tca gga aag gag       48
Met Asp Val Asp Glu Gly Gln Asp Met Ser Gln Val Ser Gly Lys Glu
1               5                   10                  15
```

```
agc ccc cca gtc agt gac act cca gat gaa ggg gat gag ccc atg cct        96
Ser Pro Pro Val Ser Asp Thr Pro Asp Glu Gly Asp Glu Pro Met Pro
            20                  25                  30 gtc cct gag gac ctg tcc act acc tct gga gca cag cag aac tcc aag       144
Val Pro Glu Asp Leu Ser Thr Thr Ser Gly Ala Gln Gln Asn Ser Lys
        35                  40                  45 agt gat cga ggc atg gcc agt aat gtt aaa gta gag act cag agt gat       192
Ser Asp Arg Gly Met Ala Ser Asn Val Lys Val Glu Thr Gln Ser Asp
    50                  55                  60 gaa gag aat ggg cgt gcc tgt gaa atg aat ggg gaa gaa tgt gca gag       240
Glu Glu Asn Gly Arg Ala Cys Glu Met Asn Gly Glu Glu Cys Ala Glu
65                  70                  75                  80 gat tta cga atg ctt gat gcc tcg gga gag aaa atg aat ggc tcc cac       288
Asp Leu Arg Met Leu Asp Ala Ser Gly Glu Lys Met Asn Gly Ser His
                85                  90                  95 agg gac caa ggc agc tcg gct ttg tca gga gtt gga ggc att cga ctt       336
Arg Asp Gln Gly Ser Ser Ala Leu Ser Gly Val Gly Gly Ile Arg Leu
            100                 105                 110 cct aac gga aaa cta aag tgt gat atc tgt ggg atc gtt tgc atc ggg       384
Pro Asn Gly Lys Leu Lys Cys Asp Ile Cys Gly Ile Val Cys Ile Gly
        115                 120                 125 ccc aat gtg ctc atg gtt cac aaa aga agt cat act ggt gaa cgg cct       432
Pro Asn Val Leu Met Val His Lys Arg Ser His Thr Gly Glu Arg Pro
    130                 135                 140 ttc cag tgc aac cag tct ggg gcc tcc ttt acc cag aaa ggc aac ctc       480
Phe Gln Cys Asn Gln Ser Gly Ala Ser Phe Thr Gln Lys Gly Asn Leu
145                 150                 155                 160 ctg cgg cac atc aag ctg cac tcg ggt gag aag ccc ttc aaa tgc cat       528
Leu Arg His Ile Lys Leu His Ser Gly Glu Lys Pro Phe Lys Cys His
                165                 170                 175 ctt tgc aac tat gcc tgc cgc cgg agg gac gcc ctc acc ggc cac ctg       576
Leu Cys Asn Tyr Ala Cys Arg Arg Arg Asp Ala Leu Thr Gly His Leu
            180                 185                 190 agg acg cac tcc gga gac aag tgc ctg tca gac atg ccc tat gac agt       624
Arg Thr His Ser Gly Asp Lys Cys Leu Ser Asp Met Pro Tyr Asp Ser
        195                 200                 205 gcc aac tat gag aag gag gat atg atg aca tcc cac gtg atg gac cag       672
Ala Asn Tyr Glu Lys Glu Asp Met Met Thr Ser His Val Met Asp Gln
    210                 215                 220 gcc atc aac aat gcc atc aac tac ctg ggg gct gag tcc ctg cgc cca       720
Ala Ile Asn Asn Ala Ile Asn Tyr Leu Gly Ala Glu Ser Leu Arg Pro
225                 230                 235                 240 ttg gtg cag aca ccc ccc ggt agc tcc gag gtg gtg cca gtc atc agc       768
Leu Val Gln Thr Pro Pro Gly Ser Ser Glu Val Val Pro Val Ile Ser
                245                 250                 255 tcc atg tac cag ctg cac aag ccc ccc tca gat ggc ccc cca cgg tcc       816
Ser Met Tyr Gln Leu His Lys Pro Pro Ser Asp Gly Pro Pro Arg Ser
            260                 265                 270 aac cat tca gca cag gac gcc gtg gat aac ttg ctg ctg ctg tcc aag       864
Asn His Ser Ala Gln Asp Ala Val Asp Asn Leu Leu Leu Leu Ser Lys
        275                 280                 285 gcc aag tct gtg tca tcg gag cga gag gcc tcc ccg agc aac agc tgc       912
Ala Lys Ser Val Ser Ser Glu Arg Glu Ala Ser Pro Ser Asn Ser Cys
    290                 295                 300 caa gac tcc aca gat aca gag agc aac gcg gag gaa cag cgc agc ggc       960
Gln Asp Ser Thr Asp Thr Glu Ser Asn Ala Glu Glu Gln Arg Ser Gly
305                 310                 315                 320 ctt atc tac cta acc aac cac atc aac ccg cat gca cgc aat ggg ctg      1008
Leu Ile Tyr Leu Thr Asn His Ile Asn Pro His Ala Arg Asn Gly Leu
                325                 330                 335
```

```
gct ctc aag gag gag cag cgc gcc tac gag gtg ctg agg gcg gcc tca      1056
Ala Leu Lys Glu Glu Gln Arg Ala Tyr Glu Val Leu Arg Ala Ala Ser
            340                 345                 350 gag aac tcg cag gat gcc ttc cgt gtg gtc agc acg agt ggc gag cag      1104
Glu Asn Ser Gln Asp Ala Phe Arg Val Val Ser Thr Ser Gly Glu Gln
                355                 360                 365 ctg aag gtg tac aag tgc gaa cac tgc cgc gtg ctc ttc ctg gat cac      1152
Leu Lys Val Tyr Lys Cys Glu His Cys Arg Val Leu Phe Leu Asp His
370                 375                 380 gtc atg tat acc att cac atg ggc tgc cat ggc tgc cat ggc ttt cgg      1200
Val Met Tyr Thr Ile His Met Gly Cys His Gly Cys His Gly Phe Arg
385                 390                 395                 400 gat ccc ttt gag tgt aac atg tgt ggt tat cac agc cag gac agg tac      1248
Asp Pro Phe Glu Cys Asn Met Cys Gly Tyr His Ser Gln Asp Arg Tyr
                405                 410                 415 gag ttc tca tcc cat atc acg cgg ggg gag cat cgt tac cac ctg agc      1296
Glu Phe Ser Ser His Ile Thr Arg Gly Glu His Arg Tyr His Leu Ser
            420                 425                 430

<210> SEQ ID NO 18
<211> LENGTH: 2049
<212> TYPE: DNA
<213> ORGANISM: Mus musculus
<220> FEATURE:
<221> NAME/KEY: CDS
<222> LOCATION: (223)...(1776)

<400> SEQUENCE: 18
aattcgttct accttctctg aacccccagtg gtgtgtcaag gccggactgg gagcttgggg    60
gaagaggaag aggaagagga atctgcggct catccaggga tcagggtcct tcccaagtgg   120
ccactcagag gggactcaga gcaagtctag atttgtgtgg cagagagaga cagctctcgt   180
ttggccttgg ggaggcacaa gtctgttgat aacctgaaga ca atg gat gtc gat      234
                                              Met Asp Val Asp
                                               1 gag ggt caa gac atg tcc caa gtt tca gga aag gag agc ccc cca gtc      282
Glu Gly Gln Asp Met Ser Gln Val Ser Gly Lys Glu Ser Pro Pro Val
 5                  10                  15                  20 agt gac act cca gat gaa ggg gat gag ccc atg cct gtc cct gag gac      330
Ser Asp Thr Pro Asp Glu Gly Asp Glu Pro Met Pro Val Pro Glu Asp
                25                  30                  35 ctg tcc act acc tct gga gca cag cag aac tcc aag agt gat cga ggc      378
Leu Ser Thr Thr Ser Gly Ala Gln Gln Asn Ser Lys Ser Asp Arg Gly
            40                  45                  50 atg gcc agt aat gtt aaa gta gag act cag agt gat gaa gag aat ggg      426
Met Ala Ser Asn Val Lys Val Glu Thr Gln Ser Asp Glu Glu Asn Gly
        55                  60                  65 cgt gcc tgt gaa atg aat ggg gaa gaa tgt gca gag gat tta cga atg      474
Arg Ala Cys Glu Met Asn Gly Glu Glu Cys Ala Glu Asp Leu Arg Met
 70                  75                  80 ctt gat gcc tcg gga gag aaa atg aat ggc tcc cac agg gac caa ggc      522
Leu Asp Ala Ser Gly Glu Lys Met Asn Gly Ser His Arg Asp Gln Gly
            85                  90                  95                 100 agc tcg gct ttg tca gga gtt gga ggc att cga ctt cct aac gga aaa      570
Ser Ser Ala Leu Ser Gly Val Gly Gly Ile Arg Leu Pro Asn Gly Lys
                105                 110                 115 cta aag tgt gat atc tgt ggg atc gtt tgc atc ggg ccc aat gtg ctc      618
Leu Lys Cys Asp Ile Cys Gly Ile Val Cys Ile Gly Pro Asn Val Leu
            120                 125                 130 atg gtt cac aaa aga agt cat act ggt gaa cgg cct ttc cag tgc aac      666
```

-continued

```
                Met Val His Lys Arg Ser His Thr Gly Glu Arg Pro Phe Gln Cys Asn
                    135                 140                 145 cag tct ggg gcc tcc ttt acc cag aaa ggc aac ctc ctg cgg cac atc              714
Gln Ser Gly Ala Ser Phe Thr Gln Lys Gly Asn Leu Leu Arg His Ile
        150                 155                 160 aag ctg cac tcg ggt gag aag ccc ttc aaa tgc cat ctt tgc aac tat              762
Lys Leu His Ser Gly Glu Lys Pro Phe Lys Cys His Leu Cys Asn Tyr
165                 170                 175                 180 gcc tgc cgc cgg agg gac gcc ctc acc ggc cac ctg agg acg cac tcc              810
Ala Cys Arg Arg Arg Asp Ala Leu Thr Gly His Leu Arg Thr His Ser
                185                 190                 195 gtt ggt aag cct cac aaa tgt gga tat tgt ggc cgg agc tat aaa cag              858
Val Gly Lys Pro His Lys Cys Gly Tyr Cys Gly Arg Ser Tyr Lys Gln
        200                 205                 210 cga agc tct tta gag gag cat aaa gag cga tgc cac aac tac ttg gaa              906
Arg Ser Ser Leu Glu Glu His Lys Glu Arg Cys His Asn Tyr Leu Glu
215                 220                 225 agc atg ggc ctt ccg ggc gtg tgc cca gtc att aag gaa gaa act aac              954
Ser Met Gly Leu Pro Gly Val Cys Pro Val Ile Lys Glu Glu Thr Asn
        230                 235                 240 cac aac gag atg gca gaa gac ctg tgc aag ata gga gca gag agg tcc             1002
His Asn Glu Met Ala Glu Asp Leu Cys Lys Ile Gly Ala Glu Arg Ser
245                 250                 255                 260 ctt gtc ctg gac agg ctg gca agc aat gtc gcc aaa cgt aag agc tct             1050
Leu Val Leu Asp Arg Leu Ala Ser Asn Val Ala Lys Arg Lys Ser Ser
                265                 270                 275 atg cct cag aaa ttt ctt gga gac aag tgc ctg tca gac atg ccc tat             1098
Met Pro Gln Lys Phe Leu Gly Asp Lys Cys Leu Ser Asp Met Pro Tyr
        280                 285                 290 gac agt gcc aac tat gag aag gag gat atg atg aca tcc cac gtg atg             1146
Asp Ser Ala Asn Tyr Glu Lys Glu Asp Met Met Thr Ser His Val Met
295                 300                 305 gac cag gcc atc aac aat gcc atc aac tac ctg ggg gct gag tcc ctg             1194
Asp Gln Ala Ile Asn Asn Ala Ile Asn Tyr Leu Gly Ala Glu Ser Leu
        310                 315                 320 cgc cca ttg gtg cag aca ccc ccc ggt agc tcc gag gtg gtg cca gtc             1242
Arg Pro Leu Val Gln Thr Pro Pro Gly Ser Ser Glu Val Val Pro Val
325                 330                 335                 340 atc agc tcc atg tac cag ctg cac aag ccc ccc tca gat ggc ccc cca             1290
Ile Ser Ser Met Tyr Gln Leu His Lys Pro Pro Ser Asp Gly Pro Pro
                345                 350                 355 cgg tcc aac cat tca gca cag gac gcc gtg gat aac ttg ctg ctg ctg             1338
Arg Ser Asn His Ser Ala Gln Asp Ala Val Asp Asn Leu Leu Leu Leu
        360                 365                 370 tcc aag gcc aag tct gtg tca tcg gag cga gag gcc tcc ccg agc aac             1386
Ser Lys Ala Lys Ser Val Ser Ser Glu Arg Glu Ala Ser Pro Ser Asn
375                 380                 385 agc tgc caa gac tcc aca gat aca gag agc aac gcg gag gaa cag cgc             1434
Ser Cys Gln Asp Ser Thr Asp Thr Glu Ser Asn Ala Glu Glu Gln Arg
        390                 395                 400 agc ggc ctt atc tac cta acc aac cac atc aac ccg cat gca cgc aat             1482
Ser Gly Leu Ile Tyr Leu Thr Asn His Ile Asn Pro His Ala Arg Asn
405                 410                 415                 420 ggg ctg gct ctc aag gag gag cag cgc gcc tac gag gtg ctg agg gcg             1530
Gly Leu Ala Leu Lys Glu Glu Gln Arg Ala Tyr Glu Val Leu Arg Ala
                425                 430                 435 gcc tca gag aac tcg cag gat gcc ttc cgt gtg gtc agc acg agt ggc             1578
Ala Ser Glu Asn Ser Gln Asp Ala Phe Arg Val Val Ser Thr Ser Gly
        440                 445                 450
```

-continued

| | | |
|---|---|---|
| gag cag ctg aag gtg tac aag tgc gaa cac tgc cgc gtg ctc ttc ctg<br>Glu Gln Leu Lys Val Tyr Lys Cys Glu His Cys Arg Val Leu Phe Leu<br>    455                 460                 465 | | 1626 |
| gat cac gtc atg tat acc att cac atg ggc tgc cat ggc tgc cat ggc<br>Asp His Val Met Tyr Thr Ile His Met Gly Cys His Gly Cys His Gly<br>470                 475                 480 | | 1674 |
| ttt cgg gat ccc ttt gag tgt aac atg tgt ggt tat cac agc cag gac<br>Phe Arg Asp Pro Phe Glu Cys Asn Met Cys Gly Tyr His Ser Gln Asp<br>485                 490                 495                 500 | | 1722 |
| agg tac gag ttc tca tcc cat atc acg cgg ggg gag cat cgt tac cac<br>Arg Tyr Glu Phe Ser Ser His Ile Thr Arg Gly Glu His Arg Tyr His<br>            505                 510                 515 | | 1770 |
| ctg agc taaacccagc caggcccac tgaagcacaa agatagctgg ttatgcctcc<br>Leu Ser | | 1826 |
| ttcccggcag ctggaccac agcggacaat gtgggagtgg atttgcaggc agcatttgtt | | 1886 |
| cttttatgtt ggttgtttgg cgtttcattt gcgttggaag ataagttttt aatgttagtg | | 1946 |
| acaggattgc attgcatcag caacattcac aacatccatc cttctagcca gttttgttca | | 2006 |
| ctggtagctg aggtttcccg gatatgtggc ttcctaacac tct | | 2049 |

<210> SEQ ID NO 19
<211> LENGTH: 1170
<212> TYPE: DNA
<213> ORGANISM: Mus musculus
<220> FEATURE:
<221> NAME/KEY: CDS
<222> LOCATION: (1)...(1170)

<400> SEQUENCE: 19

| | | |
|---|---|---|
| atg gat gtc gat gag ggt caa gac atg tcc caa gtt tca gga aag gag<br>Met Asp Val Asp Glu Gly Gln Asp Met Ser Gln Val Ser Gly Lys Glu<br>1               5                   10                  15 | | 48 |
| agc ccc cca gtc agt gac act cca gat gaa ggg gat gag ccc atg cct<br>Ser Pro Pro Val Ser Asp Thr Pro Asp Glu Gly Asp Glu Pro Met Pro<br>            20                  25                  30 | | 96 |
| gtc cct gag gac ctg tcc act acc tct gga gca cag cag aac tcc aag<br>Val Pro Glu Asp Leu Ser Thr Thr Ser Gly Ala Gln Gln Asn Ser Lys<br>        35                  40                  45 | | 144 |
| agt gat cga ggc atg ggt gaa cgg cct ttc cag tgc aac cag tct ggg<br>Ser Asp Arg Gly Met Gly Glu Arg Pro Phe Gln Cys Asn Gln Ser Gly<br>    50                  55                  60 | | 192 |
| gcc tcc ttt acc cag aaa ggc aac ctc ctg cgg cac atc aag ctg cac<br>Ala Ser Phe Thr Gln Lys Gly Asn Leu Leu Arg His Ile Lys Leu His<br>65                  70                  75                  80 | | 240 |
| tcg ggt gag aag ccc ttc aaa tgc cat ctt tgc aac tat gcc tgc cgc<br>Ser Gly Glu Lys Pro Phe Lys Cys His Leu Cys Asn Tyr Ala Cys Arg<br>                85                  90                  95 | | 288 |
| cgg agg gac gcc ctc acc ggc cac ctg agg acg cac tcc gtc att aag<br>Arg Arg Asp Ala Leu Thr Gly His Leu Arg Thr His Ser Val Ile Lys<br>            100                 105                 110 | | 336 |
| gaa gaa act aac cac aac gag atg gca gaa gac ctg tgc aag ata gga<br>Glu Glu Thr Asn His Asn Glu Met Ala Glu Asp Leu Cys Lys Ile Gly<br>        115                 120                 125 | | 384 |
| gca gag agg tcc ctt gtc ctg gac agg ctg gca agc aat gtc gcc aaa<br>Ala Glu Arg Ser Leu Val Leu Asp Arg Leu Ala Ser Asn Val Ala Lys<br>    130                 135                 140 | | 432 |
| cgt aag agc tct atg cct cag aaa ttt ctt gga gac aag tgc ctg tca<br>Arg Lys Ser Ser Met Pro Gln Lys Phe Leu Gly Asp Lys Cys Leu Ser<br>145                 150                 155                 160 | | 480 |
| gac atg ccc tat gac agt gcc aac tat gag aag gag gat atg atg aca<br>Asp Met Pro Tyr Asp Ser Ala Asn Tyr Glu Lys Glu Asp Met Met Thr | | 528 |

-continued

```
Asp Met Pro Tyr Asp Ser Ala Asn Tyr Glu Lys Glu Asp Met Met Thr
                165                 170                 175 tcc cac gtg atg gac cag gcc atc aac aat gcc atc aac tac ctg ggg      576
Ser His Val Met Asp Gln Ala Ile Asn Asn Ala Ile Asn Tyr Leu Gly
            180                 185                 190 gct gag tcc ctg cgc cca ttg gtg cag aca ccc ccc ggt agc tcc gag      624
Ala Glu Ser Leu Arg Pro Leu Val Gln Thr Pro Pro Gly Ser Ser Glu
        195                 200                 205 gtg gtg cca gtc atc agc tcc atg tac cag ctg cac aag ccc ccc tca      672
Val Val Pro Val Ile Ser Ser Met Tyr Gln Leu His Lys Pro Pro Ser
    210                 215                 220 gat ggc ccc cca cgg tcc aac cat tca gca cag gac gcc gtg gat aac      720
Asp Gly Pro Pro Arg Ser Asn His Ser Ala Gln Asp Ala Val Asp Asn
225                 230                 235                 240 ttg ctg ctg ctg tcc aag gcc aag tct gtg tca tcg gag cga gag gcc      768
Leu Leu Leu Leu Ser Lys Ala Lys Ser Val Ser Ser Glu Arg Glu Ala
                245                 250                 255 tcc ccg agc aac agc tgc caa gac tcc aca gat aca gag agc aac gcg      816
Ser Pro Ser Asn Ser Cys Gln Asp Ser Thr Asp Thr Glu Ser Asn Ala
            260                 265                 270 gag gaa cag cgc agc ggc ctt atc tac cta acc aac cac atc aac ccg      864
Glu Glu Gln Arg Ser Gly Leu Ile Tyr Leu Thr Asn His Ile Asn Pro
        275                 280                 285 cat gca cgc aat ggg ctg gct ctc aag gag gag cag cgc gcc tac gag      912
His Ala Arg Asn Gly Leu Ala Leu Lys Glu Glu Gln Arg Ala Tyr Glu
    290                 295                 300 gtg ctg agg gcg gcc tca gag aac tcg cag gat gcc ttc cgt gtg gtc      960
Val Leu Arg Ala Ala Ser Glu Asn Ser Gln Asp Ala Phe Arg Val Val
305                 310                 315                 320 agc acg agt ggc gag cag ctg aag gtg tac aag tgc gaa cac tgc cgc     1008
Ser Thr Ser Gly Glu Gln Leu Lys Val Tyr Lys Cys Glu His Cys Arg
                325                 330                 335 gtg ctc ttc ctg gat cac gtc atg tat acc att cac atg ggc tgc cat     1056
Val Leu Phe Leu Asp His Val Met Tyr Thr Ile His Met Gly Cys His
            340                 345                 350 ggc tgc cat ggc ttt cgg gat ccc ttt gag tgt aac atg tgt ggt tat     1104
Gly Cys His Gly Phe Arg Asp Pro Phe Glu Cys Asn Met Cys Gly Tyr
        355                 360                 365 cac agc cag gac agg tac gag ttc tca tcc cat atc acg cgg ggg gag     1152
His Ser Gln Asp Arg Tyr Glu Phe Ser Ser His Ile Thr Arg Gly Glu
    370                 375                 380 cat cgt tac cac ctg agc                                             1170
His Arg Tyr His Leu Ser
385                 390

<210> SEQ ID NO 20
<211> LENGTH: 1128
<212> TYPE: DNA
<213> ORGANISM: Mus musculus
<220> FEATURE:
<221> NAME/KEY: CDS
<222> LOCATION: (1)...(1128)

<400> SEQUENCE: 20 atg gat gtc gat gag ggt caa gac atg tcc caa gtt tca gga aag gag       48
Met Asp Val Asp Glu Gly Gln Asp Met Ser Gln Val Ser Gly Lys Glu
1               5                   10                  15 agc ccc cca gtc agt gac act cca gat gaa ggg gat gag ccc atg cct       96
Ser Pro Pro Val Ser Asp Thr Pro Asp Glu Gly Asp Glu Pro Met Pro
            20                  25                  30 gtc cct gag gac ctg tcc act acc tct gga gca cag cag aac tcc aag      144
```

|     |     |     |     |     |     |     |     |     |     |     |     |     |     |     |     |
|---|---|---|---|---|---|---|---|---|---|---|---|---|---|---|---|
|     | Val | Pro | Glu | Asp | Leu | Ser | Thr | Thr | Ser | Gly | Ala | Gln | Gln | Asn | Ser | Lys |
|     |     |     | 35  |     |     |     |     | 40  |     |     |     |     | 45  |     |     |     |

```
agt gat cga ggc atg gcc agt aat gtt aaa gta gag act cag agt gat      192
Ser Asp Arg Gly Met Ala Ser Asn Val Lys Val Glu Thr Gln Ser Asp
 50                  55                  60 gaa gag aat ggg cgt gcc tgt gaa atg aat ggg gaa gaa tgt gca gag      240
Glu Glu Asn Gly Arg Ala Cys Glu Met Asn Gly Glu Glu Cys Ala Glu
 65                  70                  75                  80 gat tta cga atg ctt gat gcc tcg gga gag aaa atg aat ggc tcc cac      288
Asp Leu Arg Met Leu Asp Ala Ser Gly Glu Lys Met Asn Gly Ser His
                 85                  90                  95 agg gac caa ggc agc tcg gct ttg tca gga gtt gga ggc att cga ctt      336
Arg Asp Gln Gly Ser Ser Ala Leu Ser Gly Val Gly Gly Ile Arg Leu
                100                 105                 110 cct aac gga aaa cta aag tgt gat atc tgt ggg atc gtt tgc atc ggg      384
Pro Asn Gly Lys Leu Lys Cys Asp Ile Cys Gly Ile Val Cys Ile Gly
            115                 120                 125 ccc aat gtg ctc atg gtt cac aaa aga agt cat act gga gac aag tgc      432
Pro Asn Val Leu Met Val His Lys Arg Ser His Thr Gly Asp Lys Cys
        130                 135                 140 ctg tca gac atg ccc tat gac agt gcc aac tat gag aag gag gat atg      480
Leu Ser Asp Met Pro Tyr Asp Ser Ala Asn Tyr Glu Lys Glu Asp Met
145                 150                 155                 160 atg aca tcc cac gtg atg gac cag gcc atc aac aat gcc atc aac tac      528
Met Thr Ser His Val Met Asp Gln Ala Ile Asn Asn Ala Ile Asn Tyr
                165                 170                 175 ctg ggg gct gag tcc ctg cgc cca ttg gtg cag aca ccc ccc ggt agc      576
Leu Gly Ala Glu Ser Leu Arg Pro Leu Val Gln Thr Pro Pro Gly Ser
            180                 185                 190 tcc gag gtg gtg cca gtc atc agc tcc atg tac cag ctg cac aag ccc      624
Ser Glu Val Val Pro Val Ile Ser Ser Met Tyr Gln Leu His Lys Pro
        195                 200                 205 ccc tca gat ggc ccc cca cgg tcc aac cat tca gca cag gac gcc gtg      672
Pro Ser Asp Gly Pro Pro Arg Ser Asn His Ser Ala Gln Asp Ala Val
    210                 215                 220 gat aac ttg ctg ctg ctg tcc aag gcc aag tct gtg tca tcg gag cga      720
Asp Asn Leu Leu Leu Leu Ser Lys Ala Lys Ser Val Ser Ser Glu Arg
225                 230                 235                 240 gag gcc tcc ccg agc aac agc tgc caa gac tcc aca gat aca gag agc      768
Glu Ala Ser Pro Ser Asn Ser Cys Gln Asp Ser Thr Asp Thr Glu Ser
                245                 250                 255 aac gcg gag gaa cag cgc agc ggc ctt atc tac cta acc aac cac atc      816
Asn Ala Glu Glu Gln Arg Ser Gly Leu Ile Tyr Leu Thr Asn His Ile
            260                 265                 270 aac ccg cat gca cgc aat ggg ctg gct ctc aag gag gag cag cgc gcc      864
Asn Pro His Ala Arg Asn Gly Leu Ala Leu Lys Glu Glu Gln Arg Ala
        275                 280                 285 tac gag gtg ctg agg gcg gcc tca gag aac tcg cag gat gcc ttc cgt      912
Tyr Glu Val Leu Arg Ala Ala Ser Glu Asn Ser Gln Asp Ala Phe Arg
    290                 295                 300 gtg gtc agc acg agt ggc gag cag ctg aag gtg tac aag tgc gaa cac      960
Val Val Ser Thr Ser Gly Glu Gln Leu Lys Val Tyr Lys Cys Glu His
305                 310                 315                 320 tgc cgt gtg ctc ttc ctg gat cac gtc atg tat acc att cac atg ggc     1008
Cys Arg Val Leu Phe Leu Asp His Val Met Tyr Thr Ile His Met Gly
                325                 330                 335 tgc cat ggc tgc cat ggc ttt cgg gat ccc ttt gag tgt aac atg tgt     1056
Cys His Gly Cys His Gly Phe Arg Asp Pro Phe Glu Cys Asn Met Cys
            340                 345                 350
```

| | |
|---|---|
| ggt tat cac agc cag gac agg tac gag ttc tca tcc cat atc acg cgg<br>Gly Tyr His Ser Gln Asp Arg Tyr Glu Phe Ser Ser His Ile Thr Arg<br>355                     360                 365 | 1104 |
| ggg gag cat cgt tac cac ctg agc<br>Gly Glu His Arg Tyr His Leu Ser<br>370                     375 | 1128 |

<210> SEQ ID NO 21
<211> LENGTH: 1004
<212> TYPE: DNA
<213> ORGANISM: Homo sapiens
<220> FEATURE:
<221> NAME/KEY: CDS
<222> LOCATION: (1)...(1002)

<400> SEQUENCE: 21

| | |
|---|---|
| gga gaa cgg ccc ttc cag tgc aat cag tgc ggg gcc tca ttc acc cag<br>Gly Glu Arg Pro Phe Gln Cys Asn Gln Cys Gly Ala Ser Phe Thr Gln<br>1               5                   10                 15 | 48 |
| aag ggc aac ctg ctc cgg cac atc aag ctg cat tcc ggg gag aag ccc<br>Lys Gly Asn Leu Leu Arg His Ile Lys Leu His Ser Gly Glu Lys Pro<br>                20                   25                   30 | 96 |
| ttc aaa tgc cac ctc tgc aac tac gcc tgc cgc cgg agg gac gcc ctc<br>Phe Lys Cys His Leu Cys Asn Tyr Ala Cys Arg Arg Arg Asp Ala Leu<br>                35                   40                   45 | 144 |
| act ggc cac ctg agg acg cac tcc gtc att aaa gaa gaa act aag cac<br>Thr Gly His Leu Arg Thr His Ser Val Ile Lys Glu Glu Thr Lys His<br>50                    55                   60 | 192 |
| agt gaa atg gca gaa gac ctg tgc aag ata gga tca gag aga tct ctc<br>Ser Glu Met Ala Glu Asp Leu Cys Lys Ile Gly Ser Glu Arg Ser Leu<br>65                    70                   75                  80 | 240 |
| gtg ctg gac aga cta gca agt aat gtc gcc aaa cgt aag agc tct atg<br>Val Leu Asp Arg Leu Ala Ser Asn Val Ala Lys Arg Lys Ser Ser Met<br>                      85                   90                   95 | 288 |
| cct cag aaa ttt ctt ggg gac aag ggc ctg tcc gac acg ccc tac gac<br>Pro Gln Lys Phe Leu Gly Asp Lys Gly Leu Ser Asp Thr Pro Tyr Asp<br>                  100                105               110 | 336 |
| agt gcc acg tac gag aag gag aac gaa atg atg aag tcc cac gtg atg<br>Ser Ala Thr Tyr Glu Lys Glu Asn Glu Met Met Lys Ser His Val Met<br>                 115                120              125 | 384 |
| gac caa gcc atc aac aac gcc atc aac tac ctg ggg gcc gag tcc ctg<br>Asp Gln Ala Ile Asn Asn Ala Ile Asn Tyr Leu Gly Ala Glu Ser Leu<br>130                    135                140 | 432 |
| cgc ccg ctg gtg cag acg ccc ccg ggt ggt tcc gag gtg gtc ccg gtc<br>Arg Pro Leu Val Gln Thr Pro Pro Gly Gly Ser Glu Val Val Pro Val<br>145                    150                155               160 | 480 |
| atc agc ccg atg tac cag ctg cac agg cgc tcg gag ggc acc ccg cgc<br>Ile Ser Pro Met Tyr Gln Leu His Arg Arg Ser Glu Gly Thr Pro Arg<br>                  165                170              175 | 528 |
| tcc aac cac tcg gcc cag gac agc gcc gtg gag tac ctg ctg ctc<br>Ser Asn His Ser Ala Gln Asp Ser Ala Val Glu Tyr Leu Leu Leu Leu<br>                    180                185               190 | 576 |
| tcc aag gcc aag ttg gtg ccc tcg gag cgc gag gcg tcc ccg agc aac<br>Ser Lys Ala Lys Leu Val Pro Ser Glu Arg Glu Ala Ser Pro Ser Asn<br>195                    200                205 | 624 |
| agc tgc caa gac tcc acg gac acc gag agc aac aac gag gag cag cgc<br>Ser Cys Gln Asp Ser Thr Asp Thr Glu Ser Asn Asn Glu Glu Gln Arg<br>210                    215                220 | 672 |
| agc ggt ctt atc tac ctg acc aac cac atc gcc cga cgc gcg caa cgc<br>Ser Gly Leu Ile Tyr Leu Thr Asn His Ile Ala Arg Arg Ala Gln Arg<br>225                    230                235               240 | 720 |

```
                                                                -continued gtg tcg ctc aag gag gag cac cgc gcc tac gac ctg ctg cgc gcc gcc       768
Val Ser Leu Lys Glu Glu His Arg Ala Tyr Asp Leu Leu Arg Ala Ala
            245                 250                 255 tcc gag aac tcg cag gac gcg ctc cgc gtg gtc agc acc agc ggg gag       816
Ser Glu Asn Ser Gln Asp Ala Leu Arg Val Val Ser Thr Ser Gly Glu
        260                 265                 270 cag atg aag gtg tac aag tgc gaa cac tgc cgg gtg ctc ttc ctg gat       864
Gln Met Lys Val Tyr Lys Cys Glu His Cys Arg Val Leu Phe Leu Asp
    275                 280                 285 cac gtc atg tac acc atc cac atg ggc tgc cac ggc ttc cgt gat cct       912
His Val Met Tyr Thr Ile His Met Gly Cys His Gly Phe Arg Asp Pro
290                 295                 300 ttt gag tgc aac atg tgc ggc tac cac agc cag gac cgg tac gag ttc       960
Phe Glu Cys Asn Met Cys Gly Tyr His Ser Gln Asp Arg Tyr Glu Phe
305                 310                 315                 320 tcg tcg cac ata acg cga ggg gag cac cgc ttc cac atg agc               1002
Ser Ser His Ile Thr Arg Gly Glu His Arg Phe His Met Ser
                325                 330 ta                                                                    1004

<210> SEQ ID NO 22
<211> LENGTH: 470
<212> TYPE: PRT
<213> ORGANISM: Artificial Sequence
<220> FEATURE:
<223> OTHER INFORMATION: majority sequence
<221> NAME/KEY: VARIANT
<222> LOCATION: (1)...(470)
<223> OTHER INFORMATION: Xaa = Any Amino Acid

<400> SEQUENCE: 22

Xaa Xaa Ala Ser Asn Val Lys Val Glu Thr Gln Ser Asp Glu Glu Asn
  1               5                  10                  15

Gly Arg Ala Cys Glu Met Asn Gly Glu Glu Cys Ala Glu Asp Leu Arg
             20                  25                  30

Met Leu Asp Ala Ser Gly Glu Lys Met Asn Gly Ser His Arg Asp Gln
         35                  40                  45

Gly Ser Ser Ala Leu Ser Gly Val Gly Gly Ile Arg Leu Pro Asn Gly
     50                  55                  60

Lys Leu Lys Cys Asp Ile Cys Gly Ile Xaa Cys Ile Gly Pro Asn Val
 65                  70                  75                  80

Leu Met Val His Lys Arg Ser His Thr Gly Glu Arg Pro Phe Gln Cys
                 85                  90                  95

Asn Gln Cys Gly Ala Ser Phe Thr Gln Lys Gly Asn Leu Leu Arg His
            100                 105                 110

Ile Lys Leu His Ser Gly Glu Lys Pro Phe Lys Cys His Leu Cys Asn
        115                 120                 125

Tyr Ala Cys Arg Arg Arg Asp Ala Leu Thr Gly His Leu Arg Thr His
    130                 135                 140

Ser Val Gly Lys Pro His Lys Cys Gly Tyr Cys Gly Arg Ser Tyr Lys
145                 150                 155                 160

Gln Arg Xaa Ser Leu Glu Glu His Lys Glu Arg Cys His Asn Tyr Leu
                165                 170                 175

Glu Ser Met Gly Leu Pro Gly Xaa Xaa Xaa Pro Val Ile Lys Glu Glu
            180                 185                 190

Thr Xaa His Xaa Glu Met Ala Glu Asp Leu Cys Lys Ile Gly Xaa Glu
        195                 200                 205

Arg Ser Leu Val Leu Asp Arg Leu Ala Ser Asn Val Ala Lys Arg Lys
```

```
            210                 215                 220
Ser Ser Met Pro Gln Lys Phe Leu Gly Asp Lys Xaa Leu Ser Asp Xaa
225                 230                 235                 240

Pro Tyr Asp Ser Ala Xaa Tyr Glu Lys Glu Xaa Xaa Met Met Xaa Ser
                245                 250                 255

His Val Met Asp Xaa Ala Ile Asn Asn Ala Ile Asn Tyr Leu Gly Ala
                260                 265                 270

Glu Ser Leu Arg Pro Leu Val Gln Thr Pro Gly Xaa Ser Glu Val
        275                 280                 285

Val Pro Val Ile Ser Pro Met Tyr Gln Leu His Xaa Xaa Xaa Ser Xaa
        290                 295                 300

Gly Xaa Pro Arg Ser Asn His Ser Ala Gln Asp Xaa Ala Val Xaa Xaa
305                 310                 315                 320

Leu Leu Leu Leu Ser Lys Ala Lys Xaa Val Xaa Ser Glu Arg Glu Ala
                325                 330                 335

Ser Pro Ser Asn Ser Cys Gln Asp Ser Thr Asp Thr Glu Ser Asn Xaa
                340                 345                 350

Glu Glu Gln Arg Ser Gly Leu Ile Tyr Leu Thr Asn His Ile Xaa Xaa
                355                 360                 365

Xaa Ala Xaa Xaa Xaa Xaa Xaa Leu Lys Glu Glu Xaa Arg Ala Tyr Xaa
370                 375                 380

Xaa Leu Arg Ala Ala Ser Glu Asn Ser Gln Asp Ala Xaa Arg Val Val
385                 390                 395                 400

Ser Thr Ser Gly Glu Gln Xaa Lys Val Tyr Lys Cys Glu His Cys Arg
                405                 410                 415

Val Leu Phe Leu Asp His Val Met Tyr Thr Ile His Met Xaa Xaa Xaa
                420                 425                 430

Gly Cys His Gly Phe Arg Asp Pro Phe Glu Cys Asn Met Cys Gly Tyr
                435                 440                 445

His Ser Gln Asp Arg Tyr Glu Phe Ser Ser His Ile Thr Arg Gly Glu
                450                 455                 460

His Arg Xaa His Xaa Ser
465                 470

<210> SEQ ID NO 23
<211> LENGTH: 334
<212> TYPE: PRT
<213> ORGANISM: Homo sapiens

<400> SEQUENCE: 23

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
                20                  25                  30

Phe Lys Cys His Leu Cys Asn Tyr Ala Cys Arg Arg Arg Asp Ala Leu
                35                  40                  45

Thr Gly His Leu Arg Thr His Ser Val Ile Lys Glu Glu Thr Lys His
        50                  55                  60

Ser Glu Met Ala Glu Asp Leu Cys Lys Ile Gly Ser Glu Arg Ser Leu
65              70                  75                  80

Val Leu Asp Arg Leu Ala Ser Asn Val Ala Lys Arg Lys Ser Ser Met
                85                  90                  95

Pro Gln Lys Phe Leu Gly Asp Lys Gly Leu Ser Asp Thr Pro Tyr Asp
                100                 105                 110
```

```
Ser Ala Thr Tyr Glu Lys Glu Asn Glu Met Met Lys Ser His Val Met
        115                 120                 125

Asp Gln Ala Ile Asn Asn Ala Ile Asn Tyr Leu Gly Ala Glu Ser Leu
130                 135                 140

Arg Pro Leu Val Gln Thr Pro Gly Gly Ser Glu Val Val Pro Val
145                 150                 155                 160

Ile Ser Pro Met Tyr Gln Leu His Arg Arg Ser Glu Gly Thr Pro Arg
                165                 170                 175

Ser Asn His Ser Ala Gln Asp Ser Ala Val Glu Tyr Leu Leu Leu Leu
            180                 185                 190

Ser Lys Ala Lys Leu Val Pro Ser Glu Arg Glu Ala Ser Pro Ser Asn
        195                 200                 205

Ser Cys Gln Asp Ser Thr Asp Thr Glu Ser Asn Asn Glu Glu Gln Arg
    210                 215                 220

Ser Gly Leu Ile Tyr Leu Thr Asn His Ile Ala Arg Arg Ala Gln Arg
225                 230                 235                 240

Val Ser Leu Lys Glu Glu His Arg Ala Tyr Asp Leu Leu Arg Ala Ala
                245                 250                 255

Ser Glu Asn Ser Gln Asp Ala Leu Arg Val Val Ser Thr Ser Gly Glu
            260                 265                 270

Gln Met Lys Val Tyr Lys Cys Glu His Cys Arg Val Leu Phe Leu Asp
        275                 280                 285

His Val Met Tyr Thr Ile His Met Gly Cys His Gly Phe Arg Asp Pro
    290                 295                 300

Phe Glu Cys Asn Met Cys Gly Tyr His Ser Gln Asp Arg Tyr Glu Phe
305                 310                 315                 320

Ser Ser His Ile Thr Arg Gly Glu His Arg Phe His Met Ser
                325                 330

<210> SEQ ID NO 24
<211> LENGTH: 431
<212> TYPE: PRT
<213> ORGANISM: Mus musculus

<400> SEQUENCE: 24

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Ser Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Gly Lys
            100                 105                 110

Pro His Lys Cys Gly Tyr Cys Gly Arg Ser Tyr Lys Gln Arg Ser Ser
        115                 120                 125

Leu Glu Glu His Lys Glu Arg Cys His Asn Tyr Leu Glu Ser Met Gly
    130                 135                 140

Leu Pro Gly Val Cys Pro Val Ile Lys Glu Glu Thr Asn His Asn Glu
145                 150                 155                 160
```

```
Met Ala Glu Asp Leu Cys Lys Ile Gly Ala Glu Arg Ser Leu Val Leu
                165                 170                 175

Asp Arg Leu Ala Ser Asn Val Ala Lys Arg Lys Ser Ser Met Pro Gln
            180                 185                 190

Lys Phe Leu Gly Asp Lys Cys Leu Ser Asp Met Pro Tyr Asp Ser Ala
        195                 200                 205

Asn Tyr Glu Lys Glu Asp Met Met Thr Ser His Val Met Asp Gln Ala
    210                 215                 220

Ile Asn Asn Ala Ile Asn Tyr Leu Gly Ala Glu Ser Leu Arg Pro Leu
225                 230                 235                 240

Val Gln Thr Pro Pro Gly Ser Ser Glu Val Val Pro Val Ile Ser Ser
                245                 250                 255

Met Tyr Gln Leu His Lys Pro Pro Ser Asp Gly Pro Pro Arg Ser Asn
            260                 265                 270

His Ser Ala Gln Asp Ala Val Asp Asn Leu Leu Leu Leu Ser Lys Ala
        275                 280                 285

Lys Ser Val Ser Ser Glu Arg Glu Ala Ser Pro Ser Asn Ser Cys Gln
    290                 295                 300

Asp Ser Thr Asp Thr Glu Ser Asn Ala Glu Glu Gln Arg Ser Gly Leu
305                 310                 315                 320

Ile Tyr Leu Thr Asn His Ile Asn Pro His Ala Arg Asn Gly Leu Ala
                325                 330                 335

Leu Lys Glu Glu Gln Arg Ala Tyr Glu Val Leu Arg Ala Ala Ser Glu
            340                 345                 350

Asn Ser Gln Asp Ala Phe Arg Val Val Ser Thr Ser Gly Glu Gln Leu
        355                 360                 365

Lys Val Tyr Lys Cys Glu His Cys Arg Val Leu Phe Leu Asp His Val
    370                 375                 380

Met Tyr Thr Ile His Met Gly Cys His Gly Cys His Gly Phe Arg Asp
385                 390                 395                 400

Pro Phe Glu Cys Asn Met Cys Gly Tyr His Ser Gln Asp Arg Tyr Glu
                405                 410                 415

Phe Ser Ser His Ile Thr Arg Gly Glu His Arg Tyr His Leu Ser
            420                 425                 430

<210> SEQ ID NO 25
<211> LENGTH: 461
<212> TYPE: PRT
<213> ORGANISM: Homo sapiens

<400> SEQUENCE: 25

Asn Val Lys Val Glu Thr Gln Ser Asp Glu Glu Asn Gly Arg Ala Cys
1               5                   10                  15

Glu Met Asn Gly Glu Glu Cys Ala Glu Asp Leu Arg Met Leu Asp Ala
            20                  25                  30

Ser Gly Glu Lys Met Asn Gly Ser His Arg Asp Gln Gly Ser Ser Ala
        35                  40                  45

Leu Ser Gly Val Gly Gly Ile Arg Leu Pro Asn Gly Lys Leu Lys Cys
    50                  55                  60

Asp Ile Cys Gly Ile Ile Cys Ile Gly Pro Asn Val Leu Met Val His
65                  70                  75                  80

Lys Arg Ser His Thr Gly Glu Arg Pro Phe Gln Cys Asn Gln Cys Gly
                85                  90                  95

Ala Ser Phe Thr Gln Lys Gly Asn Leu Leu Arg His Ile Lys Leu His
```

-continued

```
                    100                 105                 110
Ser Gly Glu Lys Pro Phe Lys Cys His Leu Cys Asn Tyr Ala Cys Arg
        115                 120                 125
Arg Arg Asp Ala Leu Thr Gly His Leu Arg Thr His Ser Val Gly Lys
    130                 135                 140
Pro His Lys Cys Gly Tyr Cys Gly Arg Ser Tyr Lys Gln Arg Thr Ser
145                 150                 155                 160
Leu Glu Glu His Lys Glu Arg Cys His Asn Tyr Leu Glu Ser Met Gly
                165                 170                 175
Leu Pro Gly Thr Leu Tyr Pro Val Ile Lys Glu Thr Lys His Ser
            180                 185                 190
Glu Met Ala Glu Asp Leu Cys Lys Ile Gly Ser Glu Arg Ser Leu Val
        195                 200                 205
Leu Asp Arg Leu Ala Ser Asn Val Ala Lys Arg Lys Ser Ser Met Pro
    210                 215                 220
Gln Lys Phe Leu Gly Asp Lys Gly Leu Ser Asp Thr Pro Tyr Asp Ser
225                 230                 235                 240
Ala Thr Tyr Glu Lys Glu Asn Glu Met Met Lys Ser His Val Met Asp
                245                 250                 255
Gln Ala Ile Asn Asn Ala Ile Asn Tyr Leu Gly Ala Glu Ser Leu Arg
            260                 265                 270
Pro Leu Val Gln Thr Pro Pro Gly Gly Ser Glu Val Val Pro Val Ile
        275                 280                 285
Ser Pro Met Tyr Gln Leu His Arg Arg Ser Glu Gly Thr Pro Arg Ser
    290                 295                 300
Asn His Ser Ala Gln Asp Ser Ala Val Glu Tyr Leu Leu Leu Ser
305                 310                 315                 320
Lys Ala Lys Leu Val Pro Ser Glu Arg Glu Ala Ser Pro Ser Asn Ser
                325                 330                 335
Cys Gln Asp Ser Thr Asp Thr Glu Ser Asn Asn Glu Gln Arg Ser
            340                 345                 350
Gly Leu Ile Tyr Leu Thr Asn His Ile Ala Arg Arg Ala Gln Arg Val
        355                 360                 365
Ser Leu Lys Glu Glu His Arg Ala Tyr Asp Leu Leu Arg Ala Ala Ser
    370                 375                 380
Glu Asn Ser Gln Asp Ala Leu Arg Val Val Ser Thr Ser Gly Glu Gln
385                 390                 395                 400
Met Lys Val Tyr Lys Cys Glu His Cys Arg Val Leu Phe Leu Asp His
                405                 410                 415
Val Met Tyr Thr Ile His Met Gly Cys His Gly Phe Arg Asp Pro Phe
            420                 425                 430
Glu Cys Asn Met Cys Gly Tyr His Ser Gln Asp Arg Tyr Glu Phe Ser
        435                 440                 445
Ser His Ile Thr Arg Gly Glu His Arg Phe His Met Ser
    450                 455                 460
```

<210> SEQ ID NO 26
<211> LENGTH: 432
<212> TYPE: PRT
<213> ORGANISM: Mus musculus

<400> SEQUENCE: 26

```
Met Asp Val Asp Glu Gly Gln Asp Met Ser Gln Val Ser Gly Lys Glu
1               5                   10                  15
```

```
Ser Pro Pro Val Ser Asp Thr Pro Asp Glu Gly Asp Glu Pro Met Pro
            20                  25                  30

Val Pro Glu Asp Leu Ser Thr Ser Gly Ala Gln Gln Asn Ser Lys
        35                  40                  45

Ser Asp Arg Gly Met Ala Ser Asn Val Lys Val Glu Thr Gln Ser Asp
50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Ile Arg Leu
                100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Gly Glu Arg Pro
        130                 135                 140

Phe Gln Cys Asn Gln Ser Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
                180                 185                 190

Arg Thr His Ser Gly Asp Lys Cys Leu Ser Asp Met Pro Tyr Asp Ser
            195                 200                 205

Ala Asn Tyr Glu Lys Glu Asp Met Met Thr Ser His Val Met Asp Gln
        210                 215                 220

Ala Ile Asn Asn Ala Ile Asn Tyr Leu Gly Ala Glu Ser Leu Arg Pro
225                 230                 235                 240

Leu Val Gln Thr Pro Pro Gly Ser Ser Glu Val Val Pro Val Ile Ser
            245                 250                 255

Ser Met Tyr Gln Leu His Lys Pro Pro Ser Asp Gly Pro Pro Arg Ser
            260                 265                 270

Asn His Ser Ala Gln Asp Ala Val Asp Asn Leu Leu Leu Leu Ser Lys
        275                 280                 285

Ala Lys Ser Val Ser Ser Glu Arg Glu Ala Ser Pro Ser Asn Ser Cys
        290                 295                 300

Gln Asp Ser Thr Asp Thr Glu Ser Asn Ala Glu Glu Gln Arg Ser Gly
305                 310                 315                 320

Leu Ile Tyr Leu Thr Asn His Ile Asn Pro His Ala Arg Asn Gly Leu
                325                 330                 335

Ala Leu Lys Glu Glu Gln Arg Ala Tyr Glu Val Leu Arg Ala Ala Ser
            340                 345                 350

Glu Asn Ser Gln Asp Ala Phe Arg Val Val Ser Thr Ser Gly Glu Gln
            355                 360                 365

Leu Lys Val Tyr Lys Cys Glu His Cys Arg Val Leu Phe Leu Asp His
            370                 375                 380

Val Met Tyr Thr Ile His Met Gly Cys His Gly Cys His Gly Phe Arg
385                 390                 395                 400

Asp Pro Phe Glu Cys Asn Met Cys Gly Tyr His Ser Gln Asp Arg Tyr
            405                 410                 415

Glu Phe Ser Ser His Ile Thr Arg Gly Glu His Arg Tyr His Leu Ser
            420                 425                 430
```

```
<210> SEQ ID NO 27
<211> LENGTH: 518
<212> TYPE: PRT
<213> ORGANISM: Mus musculus

<400> SEQUENCE: 27

Met Asp Val Asp Glu Gly Gln Asp Met Ser Gln Val Ser Gly Lys Glu
 1               5                  10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Gly Glu Arg Pro
    130                 135                 140

Phe Gln Cys Asn Gln Ser Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Val Cys Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
            260                 265                 270

Arg Lys Ser Ser Met Pro Gln Lys Phe Leu Gly Asp Lys Cys Leu Ser
        275                 280                 285

Asp Met Pro Tyr Asp Ser Ala Asn Tyr Glu Lys Glu Asp Met Met Thr
    290                 295                 300

Ser His Val Met Asp Gln Ala Ile Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
            340                 345                 350

Asp Gly Pro Pro Arg Ser Asn His Ser Ala Gln Asp Ala Val Asp Asn
        355                 360                 365

Leu Leu Leu Leu Ser Lys Ala Lys Ser Val Ser Ser Glu Arg Glu Ala
    370                 375                 380
```

-continued

```
Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
            405                 410                 415

His Ala Arg Asn Gly Leu Ala Leu Lys Glu Glu Gln Arg Ala Tyr Glu
        420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
    450                 455                 460

Val Leu Phe Leu Asp His Val Met Tyr Thr Ile His Met Gly Cys His
465                 470                 475                 480

Gly Cys His Gly Phe Arg Asp Pro Phe Glu Cys Asn Met Cys Gly Tyr
                485                 490                 495

His Ser Gln Asp Arg Tyr Glu Phe Ser Ser His Ile Thr Arg Gly Glu
            500                 505                 510

His Arg Tyr His Leu Ser
        515

<210> SEQ ID NO 28
<211> LENGTH: 390
<212> TYPE: PRT
<213> ORGANISM: Mus musculus

<400> SEQUENCE: 28

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Ser Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Ile Lys
            100                 105                 110

Glu Glu Thr Asn His Asn Glu Met Ala Glu Asp Leu Cys Lys Ile Gly
        115                 120                 125

Ala Glu Arg Ser Leu Val Leu Asp Arg Leu Ala Ser Asn Val Ala Lys
    130                 135                 140

Arg Lys Ser Ser Met Pro Gln Lys Phe Leu Gly Asp Lys Cys Leu Ser
145                 150                 155                 160

Asp Met Pro Tyr Asp Ser Ala Asn Tyr Glu Lys Asp Met Met Thr
                165                 170                 175

Ser His Val Met Asp Gln Ala Ile Asn Asn Ala Ile Asn Tyr Leu Gly
            180                 185                 190

Ala Glu Ser Leu Arg Pro Leu Val Gln Thr Pro Pro Gly Ser Ser Glu
        195                 200                 205

Val Val Pro Val Ile Ser Ser Met Tyr Gln Leu His Lys Pro Pro Ser
    210                 215                 220

Asp Gly Pro Pro Arg Ser Asn His Ser Ala Gln Asp Ala Val Asp Asn
225                 230                 235                 240
```

```
Leu Leu Leu Leu Ser Lys Ala Lys Ser Val Ser Ser Glu Arg Glu Ala
            245                 250                 255

Ser Pro Ser Asn Ser Cys Gln Asp Ser Thr Asp Thr Glu Ser Asn Ala
            260                 265                 270

Glu Glu Gln Arg Ser Gly Leu Ile Tyr Leu Thr Asn His Ile Asn Pro
            275                 280                 285

His Ala Arg Asn Gly Leu Ala Leu Lys Glu Gln Arg Ala Tyr Glu
            290                 295                 300

Val Leu Arg Ala Ala Ser Glu Asn Ser Gln Asp Ala Phe Arg Val Val
305                 310                 315                 320

Ser Thr Ser Gly Glu Gln Leu Lys Val Tyr Lys Cys Glu His Cys Arg
            325                 330                 335

Val Leu Phe Leu Asp His Val Met Tyr Thr Ile His Met Gly Cys His
            340                 345                 350

Gly Cys His Gly Phe Arg Asp Pro Phe Glu Cys Asn Met Cys Gly Tyr
            355                 360                 365

His Ser Gln Asp Arg Tyr Glu Phe Ser Ser His Ile Thr Arg Gly Glu
            370                 375                 380

His Arg Tyr His Leu Ser
385                 390

<210> SEQ ID NO 29
<211> LENGTH: 376
<212> TYPE: PRT
<213> ORGANISM: Mus musculus

<400> SEQUENCE: 29

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
            35                  40                  45

Ser Asp Arg Gly Met Ala Ser Asn Val Lys Val Glu Thr Gln Ser Asp
50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
            85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
            115                 120                 125

Pro Asn Val Leu Met Val His Lys Arg Ser His Thr Gly Asp Lys Cys
            130                 135                 140

Leu Ser Asp Met Pro Tyr Asp Ser Ala Asn Tyr Glu Lys Glu Asp Met
145                 150                 155                 160

Met Thr Ser His Val Met Asp Gln Ala Ile Asn Asn Ala Ile Asn Tyr
            165                 170                 175

Leu Gly Ala Glu Ser Leu Arg Pro Leu Val Gln Thr Pro Gly Ser
            180                 185                 190

Ser Glu Val Val Pro Val Ile Ser Ser Met Tyr Gln Leu His Lys Pro
            195                 200                 205

Pro Ser Asp Gly Pro Pro Arg Ser Asn His Ser Ala Gln Asp Ala Val
```

```
                   210                 215                 220
Asp Asn Leu Leu Leu Ser Lys Ala Lys Ser Val Ser Ser Glu Arg
225                 230                 235                 240

Glu Ala Ser Pro Ser Asn Ser Cys Gln Asp Ser Thr Asp Thr Glu Ser
                245                 250                 255

Asn Ala Glu Glu Gln Arg Ser Gly Leu Ile Tyr Leu Thr Asn His Ile
            260                 265                 270

Asn Pro His Ala Arg Asn Gly Leu Ala Leu Lys Glu Gln Arg Ala
        275                 280                 285

Tyr Glu Val Leu Arg Ala Ala Ser Glu Asn Ser Gln Asp Ala Phe Arg
    290                 295                 300

Val Val Ser Thr Ser Gly Glu Gln Leu Lys Val Tyr Lys Cys Glu His
305                 310                 315                 320

Cys Arg Val Leu Phe Leu Asp His Val Met Tyr Thr Ile His Met Gly
                325                 330                 335

Cys His Gly Cys His Gly Phe Arg Asp Pro Phe Glu Cys Asn Met Cys
            340                 345                 350

Gly Tyr His Ser Gln Asp Arg Tyr Glu Phe Ser Ser His Ile Thr Arg
        355                 360                 365

Gly Glu His Arg Tyr His Leu Ser
    370                 375

<210> SEQ ID NO 30
<211> LENGTH: 240
<212> TYPE: PRT
<213> ORGANISM: Gallus gallus

<400> SEQUENCE: 30

Pro Pro Leu Leu Leu Val Pro Gly Glu Lys Arg His Cys Phe Asp Ala
1               5                   10                  15

Asn Tyr Asn Pro Gly Tyr Met Tyr Glu Lys Glu Asn Glu Met Met Gln
            20                  25                  30

Thr Arg Met Met Asp Gln Ala Ile Asn Asn Ala Ile Ser Tyr Leu Gly
        35                  40                  45

Ala Glu Ala Val Arg Pro Leu Val Gln Thr Pro Ala Pro Thr Ser
    50                  55                  60

Glu Met Val Pro Val Ile Ser Ser Val Tyr Pro Ile Ala Leu Thr Arg
65                  70                  75                  80

Ala Asp Met Pro Asn Gly Ala Pro Gln Glu Met Glu Lys Lys Arg Ile
                85                  90                  95

Leu Leu Pro Glu Lys Ile Leu Pro Ser Glu Arg Gly Leu Ser Pro Asn
            100                 105                 110

Asn Ser Ala Gln Asp Ser Thr Asp Thr Asp Ser Asn His Glu Asp Arg
        115                 120                 125

Gln His Leu Tyr Gln Gln Ser His Val Val Leu Pro Gln Ala Arg Asn
    130                 135                 140

Gly Met Pro Leu Leu Lys Glu Val Pro Arg Ser Phe Glu Leu Leu Lys
145                 150                 155                 160

Pro Pro Pro Ile Cys Leu Arg Asp Ser Ile Lys Val Ile Asn Lys Glu
                165                 170                 175

Gly Glu Val Met Asp Val Phe Arg Cys Asp His Cys His Val Leu Phe
            180                 185                 190

Leu Asp Tyr Val Met Phe Thr Ile His Met Gly Cys His Gly Phe Arg
        195                 200                 205
```

```
Asp Pro Phe Glu Cys Asn Met Cys Gly Tyr Arg Ser His Asp Arg Tyr
210                 215                 220

Glu Phe Ser Ser His Ile Ala Arg Gly Glu His Arg Ala Met Leu Lys
225                 230                 235                 240
```

<210> SEQ ID NO 31
<211> LENGTH: 232
<212> TYPE: PRT
<213> ORGANISM: Gallus gallus

<400> SEQUENCE: 31

```
Asp Arg Leu Asp Leu Pro Tyr Asp Ala Thr Thr Asn Tyr Glu Lys Glu
1               5                   10                  15

Asn Glu Ile Met Gln Thr His Val Ile Asp Gln Ala Ile Asn Asn Ala
                20                  25                  30

Ile Ser Tyr Leu Gly Ala Glu Ser Leu Arg Pro Leu Val Gln Thr Pro
            35                  40                  45

Pro Val Gly Ser Glu Val Val Pro Val Ile Ser Pro Met Tyr Gln Leu
50                  55                  60

His Lys Pro His Gly Asp Asn Gln Thr Arg Ser Asn His Thr Ala Gln
65                  70                  75                  80

Asp Ser Ala Val Glu Asn Leu Leu Leu Ser Lys Ala Lys Ser Val
                85                  90                  95

Ser Ser Glu Arg Asp Ala Ser Pro Ser Asn Ser Cys Gln Asp Ser Thr
                100                 105                 110

Asp Thr Glu Ser Asn Asn Glu Glu Arg Ser Gly Leu Ile Tyr Leu Thr
            115                 120                 125

Asn His Ile Gly Pro His Ala Arg Asn Gly Ile Ser Val Lys Glu Glu
130                 135                 140

Ser Arg Gln Phe Asp Val Leu Arg Ala Gly Thr Asp Asn Ser Gln Asp
145                 150                 155                 160

Ala Phe Lys Val Ile Ser Ser Asn Gly Glu Gln Val Arg Val Tyr Lys
                165                 170                 175

Cys Glu His Cys Arg Val Leu Phe Leu Asp His Val Met Tyr Thr Ile
                180                 185                 190

His Met Gly Cys His Gly Phe Arg Asp Pro Phe Glu Cys Asn Met Cys
            195                 200                 205

Gly Tyr His Ser Gln Asp Arg Tyr Glu Phe Ser Ser His Ile Thr Arg
210                 215                 220

Gly Glu His Arg Phe His Met Ser
225                 230
```

<210> SEQ ID NO 32
<211> LENGTH: 101
<212> TYPE: PRT
<213> ORGANISM: Mus musculus

<400> SEQUENCE: 32

```
Ile Arg His Glu Glu Ala Pro Ala Asn Glu Asp Glu Asp Ala Gly Glu
1               5                   10                  15

Asp Ser Met Lys Val Lys Asp Glu Tyr Ser Asp Arg Asp Glu Asn Ile
                20                  25                  30

Met Lys Pro Glu Pro Met Gly Asp Ala Glu Glu Ser Glu Met Pro Tyr
            35                  40                  45

Ser Tyr Ala Arg Glu Tyr Ser Asp Tyr Glu Ser Ile Lys Leu Glu Arg
50                  55                  60
```

```
His Val Pro Tyr Asp Asn Ser Arg Pro Thr Ser Gly Lys Met Asn Cys
 65                  70                  75                  80

Asp Val Cys Gly Leu Ser Cys Ile Ser Phe Asn Val Leu Met Val His
                 85                  90                  95

Lys Arg Ser His Thr
            100
```

<210> SEQ ID NO 33
<211> LENGTH: 56
<212> TYPE: PRT
<213> ORGANISM: Mus musculus

<400> SEQUENCE: 33

```
Gly Glu Arg Pro Phe Gln Cys Asn Gln Cys Gly Ala Ser Phe Thr Gln
  1               5                  10                  15

Lys Gly Asn Leu Leu Arg His Ile Lys Leu His Thr Gly Glu Lys Pro
                 20                  25                  30

Phe Lys Cys His Leu Cys Asn Tyr Ala Cys Gln Arg Arg Asp Ala Leu
             35                  40                  45

Thr Gly His Leu Arg Thr His Ser
         50                  55
```

<210> SEQ ID NO 34
<211> LENGTH: 39
<212> TYPE: PRT
<213> ORGANISM: Mus musculus

<400> SEQUENCE: 34

```
Val Glu Lys Pro Tyr Lys Cys Glu Phe Cys Gly Arg Ser Tyr Lys Gln
  1               5                  10                  15

Arg Ser Ser Leu Glu Glu His Lys Glu Arg Cys Arg Ala Phe Leu Gln
                 20                  25                  30

Asn Pro Asp Leu Gly Asp Ala
             35
```

<210> SEQ ID NO 35
<211> LENGTH: 39
<212> TYPE: PRT
<213> ORGANISM: Mus musculus

<400> SEQUENCE: 35

```
Ala Ser Val Glu Ala Arg His Ile Lys Ala Glu Met Gly Ser Glu Arg
  1               5                  10                  15

Ala Leu Val Leu Asp Arg Leu Ala Ser Asn Val Ala Lys Arg Lys Ser
                 20                  25                  30

Ser Met Pro Gln Lys Phe Ile
             35
```

<210> SEQ ID NO 36
<211> LENGTH: 233
<212> TYPE: PRT
<213> ORGANISM: Mus musculus

<400> SEQUENCE: 36

```
Gly Glu Lys Arg His Cys Phe Asp Ala Asn Tyr Asn Pro Gly Tyr Met
  1               5                  10                  15

Tyr Glu Lys Glu Asn Glu Met Met Gln Thr Arg Met Met Asp Gln Ala
                 20                  25                  30

Ile Asn Asn Ala Ile Ser Tyr Leu Gly Ala Glu Ala Phe Arg Pro Leu
             35                  40                  45
```

```
Val Gln Thr Pro Pro Ala Pro Thr Ser Glu Met Val Pro Val Ile Ser
     50                  55                  60
Ser Val Tyr Pro Ile Ala Leu Thr Arg Ala Asp Met Pro Met Gly Ala
 65                  70                  75                  80
Pro Gln Glu Met Glu Lys Lys Arg Ile Leu Leu Pro Glu Lys Ile Leu
                 85                  90                  95
Pro Ser Glu Arg Gly Leu Ser Pro Asn Asn Ser Ala Gln Asp Ser Thr
                100                 105                 110
Asp Thr Asp Ser Asn His Glu Asp Arg Gln His Leu Tyr Gln Gln Ser
            115                 120                 125
His Val Val Leu Pro Gln Ala Arg Asn Gly Met Pro Leu Leu Lys Glu
        130                 135                 140
Val Pro Arg Ser Phe Glu Leu Leu Lys Pro Pro Ile Cys Leu Arg
145                 150                 155                 160
Asp Ser Ile Lys Val Ile Asn Lys Glu Gly Glu Val Met Asp Val Phe
                165                 170                 175
Arg Cys Asp His Cys His Val Leu Phe Leu Asp Tyr Val Met Phe Thr
            180                 185                 190
Ile His Met Gly Cys His Gly Phe Arg Asp Pro Phe Glu Cys Asn Met
        195                 200                 205
Cys Gly Tyr Arg Ser His Asp Arg Tyr Glu Phe Ser Ser His Ile Ala
    210                 215                 220
Arg Gly Glu His Arg Ala Met Leu Lys
225                 230

<210> SEQ ID NO 37
<211> LENGTH: 208
<212> TYPE: PRT
<213> ORGANISM: Artificial Sequence
<220> FEATURE:
<223> OTHER INFORMATION: majority sequence
<221> NAME/KEY: VARIANT
<222> LOCATION: (1)...(208)
<223> OTHER INFORMATION: Xaa = Any Amino Acid

<400> SEQUENCE: 37

Xaa Arg Asp Glu Asn Xaa Xaa Lys Xaa Glu Pro Met Gly Xaa Ala Glu
 1               5                  10                  15
Glu Xaa Glu Xaa Pro Tyr Ser Tyr Xaa Arg Glu Tyr Xaa Xaa Tyr Glu
                 20                  25                  30
Xaa Ile Lys Leu Glu Arg His Val Xaa Xaa Asp Xaa Ser Arg Pro Thr
             35                  40                  45
Ser Gly Lys Met Asn Cys Asp Val Cys Gly Leu Ser Cys Ile Ser Phe
 50                  55                  60
Asn Val Leu Met Val His Lys Arg Ser His Thr Gly Glu Arg Pro Phe
 65                  70                  75                  80
Gln Cys Asn Gln Cys Gly Ala Ser Phe Thr Gln Lys Gly Asn Leu Leu
                 85                  90                  95
Arg His Ile Lys Leu His Thr Gly Glu Lys Pro Phe Lys Cys His Leu
                100                 105                 110
Cys Asn Tyr Ala Cys Gln Arg Arg Asp Ala Leu Thr Gly His Leu Arg
            115                 120                 125
Thr His Ser Val Glu Lys Pro Tyr Lys Cys Glu Phe Cys Gly Arg Ser
        130                 135                 140
Tyr Lys Gln Arg Ser Ser Leu Glu Glu His Lys Glu Arg Cys Arg Xaa
145                 150                 155                 160
```

-continued

```
Phe Leu Gln Xaa Xaa Asp Xaa Gly Asp Xaa Ala Ser Xaa Glu Ala Arg
            165             170             175

His Ile Lys Ala Glu Met Gly Ser Glu Arg Ala Leu Val Leu Asp Arg
            180             185             190

Leu Ala Ser Asn Val Ala Lys Arg Lys Ser Ser Met Pro Gln Lys Phe
            195             200             205

<210> SEQ ID NO 38
<211> LENGTH: 24
<212> TYPE: DNA
<213> ORGANISM: Artificial Sequence
<220> FEATURE:
<223> OTHER INFORMATION: primer for PCR

<400> SEQUENCE: 38
atgaaagtga aagatgaata cagc                                          24
```

AIOLOS GENE

This application is a divisional of Ser. No. 08/733,622, filed Oct. 17, 1996 (now U.S. Pat. No. 6,528,634), which claims the benefit of previously filed Provisional Application Nos. 60/017,646, filed May 14, 1996 and 60/005,529, filed Oct. 18, 1995, the contents of which are incorporated in their entirety.

BACKGROUND OF THE INVENTION

The invention relates to the Aiolos gene, Aiolos polypeptide, Aiolos homodimers, Aiolos/Ikaros heterodimers and methods of using Aiolos nucleic acids and polypeptides.

SUMMARY OF THE INVENTION

In general, the invention features an Aiolos polypeptide, e.g., a polypeptide which includes all or part of the sequence shown in SEQ ID NO:2 or SEQ ID NO:8. The invention also features fragments and analogs of Aiolos polypeptides, preferably having at least one biological activity of an Aiolos polypeptide.

In preferred embodiments, the polypeptide is a recombinant or a substantially pure preparation of an Aiolos polypeptide.

In preferred embodiments, the polypeptide is a vertebrate, e.g., a mammalian, e.g., a human polypeptide.

In preferred embodiments, the Aiolos polypeptide includes additional Aiolos coding sequences 5' to that of SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments: the polypeptide has at least one biological activity, e.g., it reacts with an antibody, or antibody fragment, specific for an Aiolos polypeptide; the polypeptide includes an amino acid sequence at least 60%, 80%, 90%, 95%, 98%, or 99% homologous to an amino acid sequence from SEQ ID NO:2 or SEQ ID NO:8; the polypeptide includes an amino acid sequence essentially the same as an amino acid sequence in SEQ ID NO:2 or SEQ ID NO:8; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:2 or SEQ ID NO:8; the polypeptide is preferably at least 10, but no more than 100, amino acids in length; the Aiolos polypeptide is either, an agonist or an antagonist, of a biological activity of a naturally occurring Aiolos polypeptide.

In preferred embodiments: the Aiolos polypeptide is encoded by the nucleic acid sequence of SEQ ID NO:1 or SEQ ID NO:7, or by a nucleic acid having at least 60%, 70%, 80%, 90%, 95%, 98%, or 99% homology with the nucleic acid of SEQ ID NO:1 or SEQ ID NO:7. For example, the Aiolos polypeptide can be encoded by a nucleic acid sequence which differs from a nucleic acid sequence of SEQ ID NO:1 or SEQ ID NO:7 due to degeneracy in the genetic code.

In a preferred embodiment, the Aiolos polypeptide encodes amino acid residues 1–507 of SEQ ID NO:2 or a functionally equivalent residue in the Aiolos sequence of another vertebrate or mammal, e.g., a human.

In a preferred embodiment, the Aiolos polypeptide encodes amino acid residues 58–507 of SEQ ID NO:2 or a functionally equivalent residue in the Aiolos sequence of another vertebrate or mammal, e.g., a human.

In a preferred embodiment, the Aiolos polypeptide encodes amino acid residues 72–507 of SEQ ID NO:2 or a functionally equivalent residue in the Aiolos sequence of another vertebrate or mammal, e.g., a human.

In a preferred embodiment, the Aiolos polypeptide encodes amino acid residues 76–507 of SEQ ID NO:2 or a functionally equivalent residue in the Aiolos sequence of another vertebrate or mammal, e.g., a human.

In a preferred embodiment, the Aiolos polypeptide encodes amino acid residues 1–206 of SEQ ID NO:8.

In a preferred embodiment the Aiolos polypeptide is an agonist of a naturally-occurring mutant or wild type Aiolos polypeptide (e.g., a polypeptide having an amino acid sequence shown in SEQ ID NO:2 or SEQ ID NO:8). In another preferred embodiment, the polypeptide is an antagonist which, for example, inhibits an undesired activity of a naturally-occurring Aiolos polypeptide (e.g., a mutant polypeptide).

In a preferred embodiment, the Aiolos polypeptide differs in amino acid sequence at 1, 2, 3, 5, 10 or more residues, from a sequence in SEQ ID NO:2 or SEQ ID NO:8. The differences, however, are such that the Aiolos polypeptide exhibits at least one biological activity of an Aiolos polypeptide, e.g., the Aiolos polypeptide retains a biological activity of a naturally occurring Aiolos polypeptide.

In preferred embodiments the Aiolos polypeptide includes an Aiolos polypeptide sequence, as described herein, as well as other N-terminal and/or C-terminal amino acid sequences.

In preferred embodiments, the polypeptide includes all or a fragment of an amino acid sequence from SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In yet other preferred embodiments, the Aiolos polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase, a DNA binding domain, or a polymerase activating domain. In preferred embodiment the fusion protein can be used in a two-hybrid assay.

In a preferred embodiment, the Aiolos polypeptide is a fragment or analog of a naturally occurring Aiolos polypeptide which inhibits reactivity with antibodies, or $F(ab')_2$ fragments, specific for a naturally occurring Aiolos polypeptide.

In a preferred embodiment, the Aiolos polypeptide includes a sequence which is not present in the mature protein.

Polypeptides of the invention include those which arise as a result of the existence of multiple genes, alternative transcription events, alternative RNA splicing events, and alternative translational and postranslational events.

In preferred embodiments, the Aiolos polypeptide: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the Aiolos polypeptide includes: the YAS5 interaction domain; the YAS3 interaction domain; the YIZ Ikaros dimerization domain.

In preferred embodiments, an Aiolos polypeptide encodes: one, two, three, four, five exons, or more exons; exons 3, 4, 5 and 7; exons 3–7; exon 7(the exons are shown in FIG. 4).

In preferred embodiments, the Aiolos polypeptide has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has at least one zinc finger domain;

(f) it is not expressed in stem cells; or (g) it is a transcriptional activator of a lymphoid gene.

In other preferred embodiments, the Aiolos polypeptide has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has an N-terminal zinc finger domain;

(f) it is not expressed in stem cells; or (g) it is a transcriptional activator of a lymphoid gene.

In yet other preferred embodiments, the Aiolos polypeptide has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;.

(e) it has at least one or preferably two C-terminal zinc finger domains;

(f) it is not expressed in stem cells; or (g) it is a transcriptional activator of a lymphoid gene.

The invention includes an immunogen which includes an active or inactive Aiolos polypeptide, or an analog or a fragment thereof, in an immunogenic preparation, the immunogen being capable of eliciting an immune response specific for the Aiolos polypeptide, e.g., a humoral response, an antibody response, or a cellular response. In preferred embodiments, the immunogen comprising an antigenic determinant, e.g., a unique determinant, from a protein represented by SEQ ID NO:2 or SEQ ID NO:8. For example, the immunogen comprises amino acids 1–124 of SEQ ID NO:2 or amino acids 275–48 of SEQ ID NO:2.

The invention also includes an antibody preparation, preferably a monoclonal antibody preparation, specifically reactive with an epitope of the Aiolos immunogen or generally of an Aiolos polypeptide.

In another aspect, the invention provides a substantially pure nucleic acid having, or comprising, a nucleotide sequence which encodes a polypeptide, the amino acid sequence of which includes, or is, the sequence of an Aiolos polypeptide, or analog or fragment thereof.

In preferred embodiments, the nucleic acid encodes a vertebrate, e.g., a mammalian, e.g., a human polypeptide.

In preferred embodiments, the nucleic acid encodes an Aiolos polypeptide which includes additional Aiolos coding sequences 5' to that SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments, the nucleic acid encodes a polypeptide having one or more of the following characteristics: at least one biological activity of an Aiolos, e.g., a polypeptide specifically reactive with an antibody, or antibody fragment, directed against an Aiolos polypeptide; an amino acid sequence at least 60%, 80%, 90%, 95%, 98%, or 99% homologous to an amino acid sequence from SEQ ID NO:2 or SEQ ID NO:8; an amino acid sequence essentially the same as an amino acid sequence in SEQ ID NO:2 or SEQ ID NO:8, the polypeptide is at least 5, 10, 20, 50, 100, 150, 200, or 250 amino acids in length; at least 5, preferably at least 10, more preferably at least 20, most preferably at least 50, 100, 150, 200, or 250 contiguous amino acids from SEQ ID NO:2 or SEQ ID NO:8; an amino acid sequence which is preferably at least 10, but no more than 100, amino acids in length; the ability to act as an agonist or an antagonist of a biological activity of a naturally occurring Aiolos polypeptide.

In preferred embodiments: the nucleic acid is or includes the nucleotide sequence of SEQ ID NO:1 or SEQ ID NO:7; the nucleic acid is at least 60%, 70%, 80%, 90%, 95%, 98%, or 99% homologous with a nucleic acid sequence of SEQ ID NO:1 or SEQ ID NO:7; the nucleic acid includes a fragment of SEQ ID NO:1 or SEQ ID NO:7 which is at least 25, 50, 100, 200, 300, 400, 500, or 1,000 bases in length; the nucleic acid differs from the nucleotide sequence of SEQ ID NO:1 due to degeneracy in the genetic code.

In a preferred embodiment, the Aiolos encoding nucleic acid sequence encodes amino acid residues 1–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 58–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 72–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 76–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 1–206 of SEQ ID NO:8.

In a preferred embodiment the polypeptide encoded by the nucleic acid is an agonist which, for example, is capable of enhancing an activity of a naturally-occurring mutant or wild type Aiolos polypeptide. In another preferred embodiment, the encoded polypeptide is an antagonist which, for example, inhibits an undesired activity of a naturally-occurring Aiolos polypeptide (e.g., a polypeptide having an amino acid sequence shown in SEQ ID NO:2 or SEQ ID NO:8).

In a preferred embodiment, the encoded Aiolos polypeptide differs in amino acid sequence at 1, 2, 3, 5, 10 or more residues, from a sequence in SEQ ID NO:2 or SEQ ID NO:8. The differences, however, are such that the encoded Aiolos polypeptide exhibits at least one biological activity of a naturally occurring Aiolos polypeptide (e.g., the Aiolos polypeptide of SEQ ID NO:2 or SEQ ID NO:8).

In preferred embodiments, the nucleic acid encodes an Aiolos polypeptide which includes an Aiolos polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In preferred embodiments, the encoded polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase; a DNA binding domain; or a polymerase activating domain. In preferred embodiments the fusion protein can be used in a two-hybrid assay.

In preferred embodiments, the encoded polypeptide is a fragment or analog of a naturally occurring Aiolos polypeptide which inhibits reactivity with antibodies, or $F(ab')_2$ fragments, specific for a naturally occurring Aiolos polypeptide.

In preferred embodiments, the nucleic acid will include a transcriptional regulatory sequence, e.g. at least one of a transcriptional promoter or transcriptional enhancer sequence, operably linked to the Aiolos gene sequence, e.g.; to render the Aiolos gene sequence suitable for use as an expression vector.

In yet another preferred embodiment, the nucleic acid of the invention hybridizes under stringent conditions to a nucleic acid probe corresponding to at least 12 consecutive nucleotides from SEQ ID NO:1 or SEQ ID NO:7, or more preferably to at least 20 consecutive nucleotides from SEQ ID NO:1 or SEQ ID NO:7, or more preferably to at least 40 consecutive nucleotides from SEQ ID NO:1 or SEQ ID NO:7.

In a preferred embodiment, the nucleic acid encodes an Aiolos polypeptide which includes a sequence which is not present in the mature protein.

In preferred embodiments, the nucleic acid encodes an Aiolos polypeptide which: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous, with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the nucleic acid encodes an Aiolos polypeptide which includes: the YAS5 interaction domain; the YAS3 interaction domain; the YIZ Ikaros dimerization domain.

In preferred embodiments, the nucleic acid encodes an Aiolos polypeptide which encodes: one, two, three, four, five exons, or more exons; exons 3, 4, 5 and 7; exons 3–7; exon 7 (the exons are shown in FIG. 4).

In preferred embodiments, the nucleic acid encodes an Aiolos polypeptide which has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has at least one zinc finger domain;

(f) it is not expressed in stem cells; or (g) it is a transcriptional activator of a lymphoid gene.

In other preferred embodiments, the nucleic acid encodes an Aiolos polypeptide which has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has an N-terminal zinc finger domain;

(f) it is not expressed in stem cells; or (g) it is a transcriptional activator of a lymphoid gene.

In yet other preferred embodiments, the nucleic acid encodes an Aiolos polypeptide which has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has at least one or preferably two C-terminal zinc finger domains;

(f) it is not expressed in stem cells; or (g) it is a transcriptional activator of a lymphoid gene.

In another aspect, the invention includes: a vector including a nucleic acid which encodes an Aiolos polypeptide; a host cell transfected with the vector; and a method of producing a recombinant Aiolos polypeptide, including culturing the cell, e.g., in a cell culture medium, and isolating the Aiolos polypeptide, e.g., an Aiolos polypeptide from the cell or from the cell culture medium.

In another aspect, the invention features, a purified recombinant nucleic acid having at least 50%, 60%, 70%, 80%, 90%, 95%, 98%, or 99% homology with a nucleotide sequence shown in SEQ ID NO:1 or SEQ ID NO:8.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1 or SEQ ID NO:8, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

The invention includes vertebrate, e.g., mammalian, e.g., rodent, e.g., mouse or rat, or human Aiolos polypeptides.

In another aspect, the invention features a method of evaluating a compound for the ability to interact with, e.g., bind, or modulate, e.g., inhibit or promote, the activity of an Aiolos polypeptide, e.g., an Aiolos monomer, or an Aiolos-Aiolos dimer or an Aiolos-Ikaros dimer. The method includes contacting the compound with the Aiolos polypeptide, and evaluating the ability of the compound to interact with or form a complex with the Aiolos polypeptide. This method can be performed in vitro, e.g., in a cell free system, or in vivo, e.g., in a two-hybrid interaction trap assay. This method can be used to identify naturally occurring molecules which interact with the Aiolos polypeptide. It can also be used to find natural or synthetic inhibitors of mutant or wild type Aiolos polypeptide. The compound can be a peptide or a non peptide molecule, e.g., a small molecule preferably 500 to 5,000 molecular weight, more preferably 500 to 1,000 molecular weight, having an aromatic scaffold, e.g., a bis-amide phenol, decorated with various functional groups.

In brief, a two hybrid assay system (see e.g., Bartel et al. (1993) *Cellular Interaction in Development: A practical Approach*, D. A. Hartley, ed., Oxford University Press, Oxford, pp. 153–179) allows for detection of protein-protein interactions in yeast cells. The known protein, e.g., an Aiolos polypeptide, is often referred to as the "bait" protein. The proteins tested for binding to the bait protein are often referred to as "fish" proteins. The "bait" protein, e.g., an Aiolos polypeptide, is fused to the GAL4 DNA binding domain. Potential "fish" proteins are fused to the GAL4 activating domain. If the "bait" protein and a "fish" protein interact, the two GAL4 domains are brought into close proximity, thus rendering the host yeast cell capable of surviving a specific growth selection.

In another aspect, the invention features a method of identifying active fragments or analogs of an Aiolos polypeptide. The method includes first identifying a compound, e.g., an Ikaros peptide, which interacts with an Aiolos polypeptide and determining the ability of the compound to bind the candidate fragment or analog. The two hybrid assay described above can bemused to obtain fragment-binding compounds. These compounds can then be used as "bait" to fish for and identify fragments of the Aiolos polypeptide which interact, bind, or form a complex with these compounds.

In another aspect, the invention features a method of making an Aiolos polypeptide, having a non-wild type activity, e.g., an antagonist, agonist, or super agonist of a naturally occurring Aiolos polypeptide. The method includes altering the sequence of an Aiolos polypeptide (e.g., SEQ ID NO:2 or SEQ ID NO:8) by, for example, substitution or deletion of one or more residues of a non-conserved region, and testing the altered polypeptide for the desired activity.

In another aspect, the invention features a method of making a fragment or analog of an Aiolos polypeptide, e.g., an Aiolos polypeptide having at least one biological activity of a naturally occurring Aiolos polypeptide. The method includes altering the sequence, e.g., by substitution or deletion of one or more residues, preferably which are non-conserved residues, of an Aiolos polypeptide, and testing the altered polypeptide for the desired activity.

In another aspect, the invention features, a method of evaluating a compound for the ability to bind a nucleic acid encoding an Aiolos gene regulatory sequence. The method includes: contacting the compound with the nucleic acid; and evaluating ability of the compound to form a complex with the nucleic acid. In preferred embodiments the Aiolos gene regulatory sequence is functionally linked to a heterologous gene, e.g., a reporter gene.

In another aspect, the invention features a human cell, e.g., a hematopoietic stem cell or a lymphocyte e.g., a T or a B cell, transformed with a nucleic acid which encodes an Aiolos polypeptide.

In another aspect, the invention features a method for treating an animal, e.g., a human, a mouse, a transgenic animal, or an animal model for a disorder, e.g., an immune system disorder, e.g., a T or B cell related disorder, e.g., a nude mouse or a SCID mouse, including administering a therapeutically-effective amount of an Aiolos polypeptide to the animal. The Aiolos polypeptide can be monomeric or an Aiolos-Aiolos or Aiolos-Ikaros dimer.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a cell selected, e.g., selected in vitro, for the expression of a product of the Aiolos gene, e.g., hematopoietic stem cells, e.g., cells transformed with Aiolos-peptide-encoding DNA, e.g., hematopoietic stem cells transformed with Aiolos-peptide-encoding DNA.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a nucleic acid encoding an Aiolos peptide and expressing the nucleic acid.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method of evaluating the effect of a treatment, e.g., a treatment designed to promote or inhibit hematopoiesis, including carrying out the treatment and evaluating the effect of the treatment on the expression of the Aiolos gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a hum an, is at risk for a disorder related to mis-expression of the Aiolos gene, e.g., a proliferative disorder, e.g., a leukemic disorder, Hodgkin's lymphoma, a cutaneuous cell lymphoma, e.g., a cutaneous T cell lymphoma, or a disorder of the immune system, e.g., an immunodeficiency, or a T or B cell related disorder, e.g., a disorder characterized by a shortage of T or B cells. The method includes examining the subject for the expression of the Aiolos gene, non-wild type expression or mis-expression being indicative of risk.

In preferred embodiments: the disorder is characterized by-unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method for determining if a subject, e.g., a human, is at risk for a disorder related to mis-expression of the Aiolos gene, e.g., a a proliferative disorder, e.g., a leukemic disorder, Hodgkin's lymphoma, a cutaneuous cell lymphoma, e.g., a cutaneous T cell lymphoma, or a disorder of the immune system, e.g., an immunodeficiency, or a T or B cell related disorder, e.g., a disorder characterized by a shortage of T or B cells. The method includes providing a nucleic acid sample from the subject and determining if the structure of an Aiolos gene allele of the subject differs from wild type.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In preferred embodiments: the determination includes determining if an Aiolos gene allele of the subject has a gross chromosomal rearrangement; the determination includes sequencing the subject's Aiolos gene.

In another aspect, the invention features, a method of evaluating an animal or cell model for a a proliferative disorder, e.g., a leukemic disorder, Hodgkin's lymphoma, a cutaneuous cell lymphoma, e.g., a cutaneous T cell lymphoma, or an immune disorder, e.g., a T cell related disorder, e.g., a disorder characterized by a shortage of T or B cells. The method includes determining if the Aiolos gene in the animal or cell model is expressed at a predetermined level or if the Aiolos gene is mis-expressed. In preferred embodiments: the predetermined level is lower than the level in a wild type or normal animal; the predetermined level is higher than the level in a wild type or normal animal; or the pattern of isoform expression is altered from wildtype.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features, a transgenic animal, e.g., a mammal, e.g., a mouse or a nonhuman primate having an Aiolos transgene.

In preferred embodiments the animal is a transgenic mouse having a mutated Aiolos transgene, the mutation occurring in, or altering, e.g., a domain of the Aiolos gene described herein.

In preferred embodiments the transgenic animal, e.g., a transgenic mouse, is homozygous for null mutations, e.g., it is homozygous for a deletion of the C terminal end of the protein, at the Aiolos locus.

In preferred embodiments the transgenic animal, e.g., a transgenic mouse, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In other preferred embodiments the transgenic animal or cell: is heterozygous for an Aiolos transgene; homozygous for an Aiolos transgene; includes a first Aiolos transgene and a second Aiolos transgene; includes an Aiolos transgene and a second transgene which is other than an Aiolos transgene, e.g., an Ikaros transgene.

In another aspect, the invention features a method for evaluating the effect of a treatment on a transgenic cell or animal having an Aiolos transgene, e.g., the effect of the treatment on the development of the immune system. The method includes administering the treatment to a cell or animal having an Aiolos transgene, and evaluating the effect of the treatment on the cell or animal. The effect can be, e.g., the effect of the treatment on: Aiolos or Ikaros expression or misexpression; the immune system or a component thereof; the nervous system or a component thereof; or the cell cycle. Immune system effects include e.g., T cell activation, T cell development, the ability to mount an immune response, the ability to give rise to a component of the immune system, B cell development, NK cell development, or the ratios $CD4^+$/$CD8^+$, $CD4^+$/$CD8^-$ and $CD4^-$/$CD8^+$.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which activates or boosts the function of the immune system; introduction of a nucleic acid, e.g., a nucleic acid which encodes or expresses a gene product, e.g., a component of the immune system; the introduction of a protein, e.g., a protein which is a component of the immune system.

In another aspect, the invention features a method for evaluating the effect of a treatment on an immune system component. The method includes: (1) supplying a transgenic cell or animal having an Aiolos transgene; (2) supplying the immune system component; (3) administering the treatment; and (4) evaluating the effect of the treatment on the immune system component.

In yet another aspect, the invention features a method for evaluating the interaction of a first immune system component with a second immune system component. The method includes: (1) supplying a transgenic cell or animal, e.g., a mammal, having an Aiolos transgene; (2) introducing the first and second immune system component into the transgenic cell or mammal; and (3) evaluating an interaction between the first and second immune system components.

Mice with mutant Aiolos transgenes which eliminate many of the normal components of the immune system, e.g., mice homozygous for a transgene having a deletion for some or all of exon 7 (corresponding to amino acids 275–507 of SEQ ID NO:2), are particularly useful for "reconstitution experiments."

In another aspect, the invention features a method for evaluating the effect of a treatment on an immune system disorder, e.g., a neoplastic disorder, a leukemia or a lymphoma, a T cell related lymphoma, including: administering the treatment to a cell or animal having an Aiolos transgene, and evaluating the effect of the treatment on the cell or animal. The effect can be, e.g., the effect of the treatment on: Aiolos or Ikaros expression or misexpression; the immune system or a component thereof; or the cell cycle. Immune system effects include e.g., T cell activation, T cell development, the ability to mount an immune response, the ability to give rise to a component of the immune system, B cell development, NK cell development, or the ratios $CD4^+$/$CD8^+$, $CD4^+$/$CD8^-$ and $CD4^-$/$CD8^+$.

The inventors have also discovered that Ikaros and Aiolos can form dimers (heterodimers) with other polypeptides. E.g., an Ikaros polypeptide can form dimers not only with Ikaros polypeptides, but with other polypeptides which bind to its C terminal region, e.g, other polypeptides having Zinc-finger regions, e.g., Aiolos polypeptides. Similarly, an Aiolos polypeptide can form dimers not only with Aiolos polypeptides, but with other polypeptides which bind to its C terminal region, e.g, other polypeptides having Zinc-finger regions, e.g., Ikaros polypeptides.

The invention also includes Ikaros-Aiolos dimers. The Ikaros member of the dimer can be any Ikaros polypeptide, e.g., any naturally occuring Ikaros or any Ikaros referred to in U.S. Ser. No. 08/238,212, filed May 2, 1994, hereby incorporated by reference. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID NO:18, and amino acid residues 229–461 of the human Ikaros protein represented by SEQ ID NO:16) but differ in the 5' region. The Ikaros family includes all naturally occurring splicing variants which arise from transcription and processing of the Ikaros gene. Five such isoforms are described herein and in U.S. Ser. No. 08/238,212, filed May 2, 1994, hereby incorporated by reference. The Ikaros family also includes other isoforms, including those generated by mutagenesis and/or by in vitro exon shuffling. The naturally occurring Ikaros proteins can bind and activate (to differing extents) the enhancer of the CD3 δ gene, and are expressed primarily in early hematopoietic and lymphoid cells in the adult. The expression pattern of this transcription factor during embryonic development suggests that Ikaros proteins play a role as a genetic switch regulating entry into the lymphoid and T cell lineages. The Ikaros gene is also expressed in the proximal corpus striatum during early embryogenesis in mice. As is discussed herein, Ikaros and Aiolos polypeptide can form Ikaros-Aiolos dimers.

Accordingly, the invention includes a substantially pure dimer which includes (or consiststs essentially of) an Aiolos polypeptide and an Ikaros polypeptide.

The Ikaros polypeptide of the Ikaros-Aiolos dimer includes one or more Ikaros exons. In preferred embodiments: the Ikaros exon is E1/2, E3, E4, E5, E6, or E7; the peptide does not include exon E7.

In other preferred embodiments: the Ikaros peptide of the Ikaros-Aiolos dimer further includes a second Ikaros exon; the second exon is any of E1/2, E3, E4, E5, E6, or E7; the first exon is E7 and the second exon is any of E1/2, E3, E4, E5, E6.

In other preferred embodiments: the Ikaros peptide of the Ikaros-Aiolos dimer further includes a third Ikaros exon; the third exon is any of E1/2, E3, E4, E5, E6, or E7; the first exon is E7, the second exon is E3, and the third exon is E1/2; the peptide is Ikaros isoform 5.

In other preferred embodiments: the Ikaros peptide of the Ikaros-Aiolos dimer further includes a fourth Ikaros exon; the fourth exon is any of E1/2, E3, E4, E5, E6, or E7; the first exon is E7, the second exon is E4, the third exon is E3, and the fourth exon is E1/2; the first exon is E7, the second exon is E4, the third exon is E3, and the fourth exon is E1/2; the peptide is Ikaros isoform 3 or 4.

In other preferred embodiments: the Ikaros peptide of the Ikaros-Aiolos dimer further includes a fifth Ikaros exon; the fifth exon is any of E1/2, E3, E4, E5, E6, or E7; the first exon is E7, the second exon is E6, the third exon is E5, the fourth exon is E4, and the fifth exon is E1/2; the peptide is Ikaros Isoform 2.

In other preferred embodiments: the Ikaros peptide of the Ikaros-Aiolos dimer further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1. In preferred embodiments: the sequence of the Ikaros exon is essentially the same as that of a naturally occurring Ikaros exon, or a fragment thereof having Ikaros activity; the amino acid sequence of the Ikaros exon is such that a nucleic acid sequence which encodes it is at least 85%, more preferably at least 90%, yet more preferably at least 95%, and most preferably at least 98 or 99% homologous with a naturally occurring Ikaros exon, or a fragment thereof having Ikaros activity, e.g., Ikaros having an amino acid sequence represented in any of SEQ ID NOS:15–21 or SEQ ID NO:22; the amino acid sequence of the Ikaros exon is such that a nucleic acid sequence which encodes it hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon represented in any of SEQ ID NOS:15–21 the amino acid sequence of the Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the Ikaros exon is essentially equal in length to a naturally occurring Ikaros exon; the amino acid sequence of the Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:15, SEQ ID NO:16, SEQ ID NO:17, SEQ ID NO:18, SEQ ID NO:19, SEQ ID NO:20, or SEQ ID NO:21; the Ikaros exon amino acid sequence is the same, or essentially the same, as that of a naturally occurring Ikaros exon, or a fragment of the sequence thereof, e.g., an Ikaros exon described in any of SEQ ID NOS:15–21; and the peptide has Ikaros peptide activity; the peptide has Ikaros antagonist activity.

In preferred embodiments: the Ikaros protein of the Ikaros-Aiolos dimer comprises a polypeptide represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the polypeptide includes at least one exon containing a zinc finger domain; the polypeptide includes at least one exon selected from E3, E4 or E5.

In preferred embodiments: the exons in the Ikaros peptide of the Ikaros-Aiolos dimer are arranged in the same relative linear order as found in a naturally occurring isoform, e.g., in Ikaros isoform 1, e.g., in a peptide having the exons E3 and E7, E3 is located N-terminal to E7; the linear order of the exons is different from that found in a naturally occurring isoform, e.g., in Ikaros isoform 1, e.g., in a peptide having exons E3, E5, and E7, the direction N-terminal to C-terminal end, is E5, E3, E7; the exons in the peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, or 5; e.g. the Ikaros protein is an isoform generated by in vitro exon shuffling.

The invention also includes: a cell, e.g., a cultured cell or a stem cell, containing purified Ikaros-protein-encoding-DNA and purified Aiolos-protein-encoding-DNA; a cell capable of expressing an Ikaros and an Aiolos protein; a cell capable of giving rise to a transgenic animal or to a homogeneous population of hemopoietic cells, e.g., lymphoid cells, e.g., T cells; an essentially homogeneous population of cells, each of which includes purified Ikaros-protein-encoding-DNA and purified Aiolos-protein-encoding-DNA; and a method for manufacture of a dimer of the invention including culturing a cell which includes a DNA, preferably a purified DNA, of the invention in a medium to express the peptides.

The invention also includes: a preparation of cells, e.g., cultured cells or a stem cells, including a cell a containing purified Ikaros-protein-encoding-DNA and a cell encoding purified Aiolos-protein-encoding-DNA.

The invention also includes substantially pure preparation of an antibody, preferably a monoclonal antibody directed against an Ikaros-Aiolos dimer (which preferably does not bind to an Ikaros-Ikaros or Aiolos-Aiolos dimer); a therapeutic composition including an Ikaros-Aiolos dimer and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering a therapeutically-effective amount of an Ikaros-Aiolos dimer to the animal.

In another aspect, the invention features a method for treating an animal, e.g., a human, a mouse, a transgenic animal, or an animal model for an immune system disorder, e.g., a T or B cell related disorder, e.g., a nude mouse or a SCID mouse including administering to the animal cells selected, e.g., selected in vitro, for the expression of a product of the Ikaros gene and of the Aiolos gene, e.g., hematopoietic stem cells, e.g., cells transformed with Ikaros-peptide-encoding DNA and or Aiolos-peptide-encoding DNA, e.g., hematopoietic stem cells transformed with Ikaros and or Aiolos-peptide-encoding DNA. The Ikaros and Aiolos DNA can be present in the same or in different cells.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering to the animal a nucleic acid encoding an Ikaros peptide and a nucleic acid encoding an Aiolos peptide and expressing the nucleic acids.

In another aspect, the invention features a method of evaluating the effect of a treatment, e.g., a treatment designed to promote or inhibit hematopoiesis, including carrying out the treatment and evaluating the effect of the treatment on the expression of the Ikaros and the Aiolos gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including examining the subject for the expression of the Ikaros-Aiolos dimers, non-wild type expression or mis-expression being indicative of risk.

In another aspect, the invention features, a method of evaluating an animal or cell model for an immune disorder, e.g., a T cell related disorder, e.g., a disorder characterized by a shortage of T or B cells, including determining if Ikaros-Aiolos dimers in the animal or cell model are expressed at a predetermined level. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an Ikaros gene or Ikaros protein encoding DNA and an Aiolos gene or Aiolos protein encoding DNA. In preferred embodiments: the Ikaros and or Aiolos gene or DNA includes a deletion, e.g. a deletion of all or part of one or more exons.

In another aspect, the invention features a method for treating an animal, e.g., a human, a mouse, a transgenic animal, or an animal model for a disorder of the nervous system, e.g., a disorder of the corpus striatum, e.g., Alzheimer's disease, immune system disorder, including administering a therapeutically effective amount of an Ikaros-Aiolos dimer to the animal.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal cells selected, e.g., selected in vitro, for the production of an Ikaros-Aiolos dimer, e.g., hematopoietic stem cells, e.g., cells transformed with Ikaros and or Aiolos protein-encoding DNA, e.g., hematopoietic stem cells transformed with Ikaros and or Aiolos-protein-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered: the cells are taken from an animal which is of the same species as is the animal to which they are administered.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal a nucleic acid encoding an Ikaros peptide and a nucleic acid encoding an Aiolos peptide and expressing the nucleic acids.

In another aspect, the invention features a method for determining if a subject, e.g., a human, is at risk for a disorder related to mis-expression of an Ikaros-Aiolos dimer, e.g., a disorder of the nervous system, e.g., a disorder of the corpus striatum, e.g., Alzheimer's disease, including examining the subject for the expression of an Ikaros-Aiolos dimer, non-wild type expression or mis-expression being indicative of risk.

In another aspect, the invention features, a method of inhibiting an interaction, e.g., binding, between a protein, e.g., an Ikaros isoform, Aiolos, an Ikaros-Ikaros dimer, an Aiolos-Aiolos dimer, or a first Ikaros-Aiolos dimer, and a DNA sequence, e.g., a DNA sequence under the control of a &A sequence, an NKFB sequence, a sequence which corresponds to an Ikaros or Aiolos binding site, or a site present in the control region of a lymphocyte restricted gene, e.g., TCR-$\alpha$, -$\beta$, or -$\delta$, CD3-$\delta$, $\epsilon$, -$\gamma$ genes, the SL3 gene, or the HIV LTR gene. The methods includes contacting the DNA sequence with an effective amount of a second Ikaros-Aiolos dimer, e.g., an Ikaros-aiolos dimer described herein.

In another aspect, the invention features, a method of inhibiting an interaction, e.g., binding, between a protein, e.g., an Ikaros isoform, Aiolos, an Ikaros-Ikaros dimer, an Aiolos-Aiolos dimer, or an Ikaros-Aiolos dimer, and a DNA sequence, e.g., a $\delta$A sequence, an NKFB sequence, a sequence which corresponds to an Ikaros binding oligonucleotide described herein, or a site present in the control region of a lymphocyte restricted gene, e.g., TCR-$\alpha$, -$\beta$, or -$\delta$, CD3-$\delta$, -$\epsilon$, -$\gamma$ genes, the SL3 gene, or the HIV LTR gene. The methods includes contacting the protein with an effective amount of an Ikaros, Aiolos, or Ikaros-Aiolos dimer-binding oligonucleotide.

In another aspect, the invention features, a method of modulating hematopoietic development, e.g., a progression of a cell through a lymphoid lineage, e.g., a lymphocyte maturation and/or function, the method including altering, in a cell or animal, a wild type expression of Ikaros-Aiolos and/or Aiolos-Aiolos dimers.

In preferred embodiments, the expression can be altered by providing Aiolos and/or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In another aspect, the invention features, a method of modulating hematopoietic development, e.g., a progression of a cell through a lymphoid lineage, e.g., a lymphocyte maturation and/or function, the method including altering, in a cell or animal, the ratio of Ikaros-Ikaros dimers to any of Aiolos-Aiolos or Aiolos-Ikaros dimers.

In preferred embodiments, the ratio can be altered by providing Aiolos or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In another aspect, the invention features, a method of modulating hematopoietic development, e.g., a progression of a cell through a lymphoid lineage, e.g., a lymphocyte maturation and/or function, the method including altering, in a cell or animal, the ratio of Aiolos-Aiolos dimers to any of Ikaros-Ikaros or Aiolos-Ikaros dimers.

In preferred embodiments, the ratio can be altered by providing Aiolos or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In general, the invention features, a method of providing a proliferation-deregulated cell, or a cell which has non-wild type, e.g., increased, antibody production. The method includes: providing a mammal having a cell which misexpresses Aiolos, e.g., a hematopoietic cell; and isolating a proliferation-deregulated or antibody overexpressing cell from the mammal. The proliferation-deregulated or antibody overexpressing cell can be, e.g., a hematopoietic cell, e.g., a B lymphocyte.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated or antibody producing cell, e.g., a lymphocyte; providing a plurality of the proliferation-deregulated cells e.g., lymphocytes or transformed lymphocytes from the mammal.

In preferred embodiments: the proliferation-deregulated or antibody producing cell e.g., a lymphocyte, e.g., a transformed lymphocyte, is isolated from a lymphoma of the mammal.

In preferred embodiments: the mammal is heterozygous at the Aiolos locus; the mammal carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the mammal carries a mutation in the control region of the Aiolos gene.

In preferred embodiments the mammal, e.g., a mouse, is homozygous for null mutations, e.g., it is homozygous for a deletion of the C terminal end of the protein, at the Aiolos locus.

In preferred embodiments the mammal, e.g., a mouse, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the mammal carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In preferred embodiments: the proliferation-deregulated or antibody producing cell is a homozygous mutant Aiolos cell e.g., a lymphocyte; the proliferation-deregulated or antibody producing lymphocyte is a B lymphocyte; the proliferation-deregulated or antibody producing cell is heterozygous or homozygous for an Aiolos transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte.

In a preferred embodiment the method further comprises isolating one or more cells, e.g., lymphocytes, from the mammal, and allowing the cell or cells to proliferate into a clonal population of cells, e.g., lymphocytes.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In preferred embodiments the method further includes providing a lymphocyte e.g., a B lymphocyte, or a substantially homogenous population of lymphocytes, e.g,. B lymphocytes, which produce an antibody molecule, e.g. an IgG, IgA, or IgE molecule, which recognizes a selected antigen.

In another aspect, the invention features, a method of providing a proliferation-deregulated cell, or a cell which has non-wild type, e.g., increased, antibody production. The method includes: causing a subject cell to misexpress the Aiolos gene, e.g., by inducing an Aiolos mutation, thereby providing a a proliferation-deregulated or antibody overexpressing cell. The proliferation-deregulated or antibody overexpressing cell can be, e.g., a hematopoietic cell, e.g., a B lymphocyte.

In preferred embodiments: the subject cell is from a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated or antibody producing cell, e.g., a lymphocyte; providing a plurality of the proliferation-deregulated cells e.g., lymphocytes or transformed lymphocytes from the mammal.

In preferred embodiments: the proliferation-deregulated or antibody producing cell e.g., a lymphocyte, e.g., a transformed lymphocyte, is isolated from cell or tissue culture.

In preferred embodiments: the cell is heterozygous at the Aiolos locus; the cell carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the cell carries a mutation in the control region of the Aiolos gene.

In preferred embodiments: the cell carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In preferred embodiments the cell, e.g., a cell, is homozygous for null mutations, e.g., it is homozygous for a deletion of the C terminal end of the protein, at the Aiolos locus.

In preferred embodiments the cell, e.g., a mouse cell, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the proliferation-deregulated or antibody producing cell is a homozygous mutant Aiolos cell e.g., a lymphocyte; the proliferation-deregulated or antibody producing lymphocyte is a B lymphocyte; the proliferation-deregulated or antibody producing cell is heterozygous or homozygous for an Aiolos transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment the method further comprises allowing the subject cell, to proliferate into a clonal population of cells, e.g., lymphocytes.

In preferred embodiments: the mammal which supplies the subject cell is immunized with an antigen. The antigen can be: an alloantigen; an xenoantigen; an autoantigen; a protein; or an antigen which gives rise to an anti-idiotypic lymphocyte.

In preferred embodiments the method further includes providing a lymphocyte e.g., a B lymphocyte, or a substantially homogenous population of lymphocytes, e.g,. B lymphocytes, which produce an antibody molecule, e.g. an IgG, IgA, or IgE molecule, which recognizes a selected antigen.

In another aspect, the invention features, a cell, e.g., a hematopoietic cell, e.g., a B lymphocyte, or, a clonal population or substantially purified preparation of such cells, preferably produced by a method of the invention described herein. Preferably, the cells misexpress Aiolos.

In another aspect, the invention features, a cell which produces or over produces an antibody, e.g., an IgA, IgG, or IgE antibody. The cell can be, e.g., a hematopoietic cell, e.g., a B lymphocyte, or a population, or substantially purified preparation, of such cells, preferably produced by a method of the invention described herein. Preferably the cells misexpress Aiolos.

In preferred embodiments the cell, e.g., a cell, is homozygous for null mutations, e.g., it is homozygous for a deletion of the C terminal end of the protein, at the Aiolos locus.

In preferred embodiments the cell, e.g., a mouse cell, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In another aspect, the invention features, a proliferation-deregulated cell. The cell can be, e.g., a hematopoietic cell, e.g., a B lymphocyte, or a population, or substantially purified preparation, of such cells, preferably produced by a method of the invention described herein. Preferably the cells misexpress Aiolos.

In preferred embodiments the cell, e.g., a cell, is homozygous for null mutations, e.g., it is homozygous for a deletion of the C terminal end of the protein, at the Aiolos locus.

In preferred embodiments the cell, e.g., a mouse cell, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In another aspect, the invention features, a lymphocyte, e.g., a B lymphoctye, or, a substantially homogenous population or substantially purified preparation of lymphocytes, preferably produced by a method of the invention described herein, which lymphocytes or population recognize a selected antigen. Preferably, the lymphocytes misexpress Aiolos.

In preferred embodiments the cell, e.g., a cell, is homozygous for null mutations, e.g., it is homozygous for a deletion of the C terminal end of the protein, at the Aiolos locus.

In preferred embodiments the cell, e.g., a mouse cell, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In another aspect, the invention features, a method of culturing an Aiolos-misexpressing cell having at least one mutant allele at the Aiolos locus. The cell can be, e.g., a hematopoietic cell, e.g., a B lymphocyte. The method includes: introducing the cell into a mammal, wherein, preferably, the mammal is other than the one from which the cell has been isolated originally; and culturing the cell.

In a preferred embodiment, the method further includes: allowing the cell to proliferate in the mammal.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell cell to divide and give rise to a proliferation-deregulated cell, e.g., a transformed lymphocyte; providing a plurality of the proliferation-deregulated cells e.g., lymphocytes or transformed lymphocytes from the mammal.

In preferred embodiments: the mammal, the cell or both, are heterozygous at the Aiolos locus; the mammal, the cell or both, carry a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the mammal, the cell or both, carry a mutation in the control region of the Aiolos gene.

In preferred embodiments: the mammal, the cell or both, carry a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal, the cell or both, carry a deletion for all or part of exon 7.

In preferred embodiments the cell, e.g., a cell, is homozygous for null mutations, e.g., it is homozygous for a deletion of the C terminal end of the protein, at the Aiolos locus.

In preferred embodiments the cell, e.g., a mouse cell, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the Aiolos-misexpressing cell is a homozygous mutant Aiolos cell e.g., a lymphocyte; the Aiolos-misexpressing cell is a B lymphocyte; the Aiolos-misexpressing cell is heterozygous or homozygous for an Aiolos transgene.

In preferred embodiments, the Aiolos-misexpressing cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte.

Aiolos wild type cells can be cultured in Aiolos misexpressing mammals.

In another aspect, the invention features, a method of modulating the activity of, or promoting the interaction of an Aiolos misexpressing cell with, a target tissue or cell. The method includes: supplying the target; and exposing the target to a Aiolos misexpressing cell, e.g., a hematopoietic cell, e.g., a B lymphocyte, preferably having at least one mutant allele at the Aiolos locus, preferably provided that: the target is not Aiolos-misexpressing; the target and the cell differ in genotype at a locus other than the Aiolos locus; the target and the cell are from different animals; the target and the cell are from different species; the target activity is modulated in a recipient mammal and either the target or the cell is from a donor mammal other than the recipient mammal; or the target is exposed to the cell in an in vitro system.

In a preferred embodiment: the donor of the Aiolos-misexpressing cell is heterozygous or homozygous for an Aiolos transgene; the donor of the Aiolos-misexpressing cell is heterozygous at the Aiolos locus; the donor of the Aiolos-misexpressing cell carries a point mutation in or a deletion for all or part of the Aiolos gene, e.g., mutation in the DNA binding region, e.g., a point mutation in, or a deletion for all or part of one or more of the four N-terminal zinc finger regions which mediate Aiolos binding to DNA or in one or both of the C-terminal zinc finger regions which mediates Aiolos dimerization; the donor of the Aiolos-misexpressing cell is human or a non-human mammal, e.g., a swine, a monkey, a goat, or a rodent, e.g., a rat or a mouse. In preferred embodiments, e.g., in the case of the human donor, the manipulation that gives rise to Aiolos deregulation, e.g., an Aiolos lesion, can be made in vitro.

In preferred embodiments: the mammal which provides the Aiolos misexpressing cell carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In another preferred embodiment: the cell is heterozygous or homozygous for an Aiolos transgene; the cell is a heterozygous Aiolos cell; the cell is a homozygous mutant Aiolos cell; the lymphocyte is a B lymphocyte.

In preferred embodiments, the cell is a lymphocyte and is: a B cell; a cell which secretes one or more anti-inflammatory cytokines; a T cell which is antigen or idiotype specific.

In a preferred embodiment: the method is performed in an in vitro system; the method is performed in vivo, e.g., in a mammal, e.g., a rodent, e.g., a mouse or a rat, or a primate, e.g., a non-human primate or a human. If the method is performed in vitro, the donor of the target cell or tissue and the lymphocyte can be same or different. If the method is performed in vivo, there is a recipient animal and one or more donors.

In preferred embodiments: the method is performed in vivo and one or more of the recipient, the donor of the target cell or tissue, the donor of the cell, is immunized with an antigen; the method is performed in vitro and one or more of the donor of the target cell or tissue, the donor of the cell is immunized with an antigen. The antigen can be: an alloantigen; a xenoantigen or an autoantigen; a protein; or an antigen which gives rise to an anti-idiotypic lymphocyte.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, bone marrow tissue, lymph node tissue or thymic tissue, or the target is a syngeneic, allogeneic, or xenogeneic tissue.

In another preferred embodiment, the target is from a mammal, e.g., a human; the mammal is a non-human mammal, e.g., a swine, a monkey, a goat, or a rodent, e.g., a rat or a mouse.

In preferred embodiments, the activity of the target which is modulated is: the production of a cytokine; the proliferation or activation of a cell of the immune system; the production of an antibody; the lysis of an antigen presenting cell or the activation of a cytolytic T lymphocyte; the effect of target on resistance to infection; the effect of target on life span; the effect of target on body weight; the effect of target on the presence, function, or morphology of tissues or organs of the immune system; the effect of target on the ability of a component of the immune system to respond to a stimulus (e.g., a diffusable substance, e.g., cytokines, other cells of the immune system, or antigens); the effect of target on the ability to exhibit immunological tolerance to an alloantigen or a xenoantigen.

In preferred embodiments the interaction is the binding of an antibody produced by the Aiolos misexpressing cell with the target.

In preferred embodiments: the target and the cell differ in genotype at a locus other than the Aiolos locus; the target and the cell are from different animals; the target is not Aiolos-misexpressing.

In another aspect, the invention features, a method of reconstituting an immune system. The method includes: supplying a recipient mammal, and introducing, preferably exogenously, into the recipient mammal, an immune system component from a donor mammal, which is Aiolos misexpressing, e.g., which carries at least one mutant allele at the Aiolos locus. The recipient mammal, can be, e.g., a human or a nonhuman mammal, e.g., a swine, a nonhuman primate, e.g., a monkey; a goat, or a rodent, e.g., a rat or a mouse. The donor mammal can be, e.g., a human or a nonhuman mammal, e.g., a swine, a monkey, a goat, or a rodent, e.g., a rat or a mouse. If the donor mammal is human, the manipulation that gives rise to Aiolos misexpression e.g., an the introduction of an Aiolos lesion, can be made in vitro. The donor mammal and the recipient mammal can be different individuals or the same individual.

In preferred embodiments, the component is or includes an Aiolos misexpressing cell, e.g., a hematopoietic cell, e.g., a pluripotent stem cell, or a descendent of a stem cell, e.g., a lymphocyte.

In preferred embodiments, the component is from a donor mammal, e.g., a human or a nonhuman mammal, e.g., a swine, a monkey, a goat, or a rodent, e.g., a rat or a mouse.

In a preferred embodiment, the method further includes: prior to introduction of a component into the subject, treating the lymphocyte to inhibit proliferation, e.g., by irradiating the component.

In a preferred embodiment, the donor mammal carries a mutation at the Aiolos gene, e.g., a deletion of all or part of the Aiolos gene.

In another preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In a preferred embodiment: the immune system component is from the same species as the recipient mammal; the immune system component is from species different from the species of the recipient mammal.

In preferred embodiments: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In preferred embodiments: the immune system component is heterozygous at the Aiolos locus; the immune system component is carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the immune system component is heterozygous or homozygous for an Aiolos transgene; the immune system component carries a mutation in the control region of the Aiolos gene.

In preferred embodiments: the immune system component carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the immune system component carries deletion for all or part of exon 7.

In preferred embodiments: the method is performed in vivo, and the recipient mammal or the donor mammal or both are immunized with an antigen. The antigen can be: an alloantigen; a xenoantigen or an autoantigen; a protein; or an antigen which gives rise to an anti-idiotypic lymphocyte.

In a preferred embodiment, the method further includes: determining a value for a parameter related to immune system function. The parameter related to the immune system function can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In another aspect, the invention features, a method of evaluating the interaction of an Aiolos misexpressing cell, e.g., a hematopoietic cell, a B lymphocyte, with an immune system component. The method includes: supplying an animal, e.g., a swine, a nonhuman primate, e.g., a monkey, a goat, or a rodent, e.g., a rat or a mouse; introducing the cell and the immune component into the animal; and evaluating the interaction between the Aiolos misexpressing cell and the immune system component.

In a preferred embodiment, the method further includes: prior to introduction of a cell into the subject, treating the lymphocyte to inhibit proliferation, e.g., by irradiating the cell.

In a preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal; the immune system component is from the same species as the lymphocyte; the immune system component is from species different from the species from which the lymphocyte is obtained.

In another preferred embodiment: the cell is from the same species as the animal; the cell is from a species which is different from the species of the animal.

In another preferred embodiment: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In a preferred embodiment: the cell is heterozygous or homozygous for an Aiolos transgene.

In preferred embodiments evaluating can include evaluating any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the method is performed in vivo, and one or more of the animal, the donor of the Aiolos misexpressing cell, the donor of the immune system component, is immunized with an antigen. The antigen can be: an alloantigen; a xenoantigen or an autoantigen; a protein; or an antigen which gives rise to an anti-idiotypic lymphocyte.

In another aspect, the invention features, a mammal, e.g., a nonhuman mammal, e.g., e.g., a swine, a nonhuman primate, e.g., a monkey, a goat, or a rodent, e.g., a rat or a mouse, having an exogenously introduced immune system component, the component being from a human or nonhuman mammal, e.g., a swine, a nonhuman primate, e.g., a monkey, a goat, or a rodent, e.g., a rat or a mouse, or cell culture which is Aiolos misexpressing or which carries at least one mutant allele at the Aiolos locus. In preferred embodiments, e.g., if the immune system component is from a wild-type animal, e.g., a human, the manipulation that gives rise to Aiolos deregulation, e.g., an Aiolos lesion, can be made in vitro.

In preferred embodiments, the component is from a human or nonhuman mammal, e.g., a swine, a nonhuman primate, e.g., a monkey, a goat, or a rodent, e.g., a rat or a mouse, which is Aiolos misexpressing.

In preferred embodiments: the component is from a mammal which is Aiolos misexpressing; the component is from a mammal which is heterozygous at the Aiolos locus; the component is from a mammal which carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the component is from a mammal which is heterozygous or homozygous for an Aiolos transgene; the component is from a mammal which carries a mutation in the control region of the Aiolos gene.

In preferred embodiments: the component is from a mammal which carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the component is from a mammal which carries deletion for all or part of exon 7.

In preferred embodiments, the immune system component is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal.

In preferred embodiments: the mammal or the donor animal which produces the immune system component or both are immunized with an antigen. The antigen can be: an alloantigen; a xenoantigen or an autoantigen; a protein; or an antigen which gives rise to an anti-idiotypic lymphocyte.

In another aspect, the invention features, a reaction mixture, preferably an in vitro reaction mixture, including an immune system component, the component including cells which misexpress Aiolos or being from an animal or cell culture which is misexpresses Aiolos or which carries at least one mutant allele at the Aiolos locus, and a target tissue or cell, wherein preferably, the immune system component and the target differ in genotype at a locus other than the Aiolos or Ikaros locus; the component and the target are from different species, or the component and the target are from different animals.

In preferred embodiments, the component is from an animal or cell culture which misexpresses Aiolos.

In preferred embodiments: the immune system component is a lymphocyte heterozygous or homozygous for an Aiolos transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for a C terminal deletion.

In preferred embodiments, the immune system component is: a B cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the target cell; the immune system component is from species different from the species of the target cell.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, lymph node tissue, bone marrow tissue or thymic tissue, or is syngeneic, allogeneic, xenogeneic, or congenic tissue.

In preferred embodiments: the donor of the immune system component or the donor of the target or both are immunized with an antigen. The antigen can be: an alloantigen; a xenoantigen or an autoantigen; a protein; or an antigen which gives rise to an anti-idiotypic lymphocyte.

In preferred embodiments the donor of the components is: a human or nonhuman mammal, e.g., a swine, a nonhuman primate, e.g., a monkey, a goat, or a rodent, e.g., a rat or mouse. In preferred embodiments, e.g., in the case of a wild-type donor, e.g., a human, the manipulation that gives rise to Aiolos deregulation, e.g., an Aiolos lesion, can be introduced in vitro.

In preferred embodiments the donor of the target is: a human or nonhuman mammal, e.g., a swine, a nonhuman primate, e.g., a monkey, a goat, or a rodent, e.g., a rat or mouse.

In preferred embodiments the reaction mixture includes an exogenously add cytokine or antigen, e.g., a protein antigen.

In another aspect, the invention features, a method of promoting or inhibiting the proliferation of a cell, or of modulating the entry of a cell into the cell cycle. The method includes: administering to the cell a compound which inhibits the formation Aiolos-Aiolos or Aiolos-Ikaros dimers. The method can be performed in vivo or in vitro. The cell can be, e.g., a hematopoietic cell, e.g., a B lymphocyte In preferred embodiments, the compound is: a competitive or noncompetitive inhibitor of the association of Aiolos or Ikaros subunits, e.g., a mutant Aiolos peptide, e.g., a mutant Aiolos peptide which has a mutation which inhibits the ability of the Aiolos protein to bind DNA but which does not inhibit the ability of the protein to form a dimer, e.g., a mutation in one or more of the four N terminal Zinc fingers binding regions. Aiolos mutants which have mutations which inhibit dimerization, e.g., mutations inone of more of the two C terminal zinc finger regions can also be used.

In preferred embodiments the compound is: a protein or peptide; a peptomimetic, a small molecule; a nucleic acid which encodes an inhibitor.

Methods for increasing cell division can be combined with procedures where it is desirable to increase cell division, e.g., the treatment, e.g., by chemotherapy or radiotherapy, of tumors or other cell-proliferative disorders.

Proliferation can be inhibited by administering wildtype Aiolos.

In another aspect, the invention features a cell, or purified preparation of cells, which include an Aiolos transgene, or which otherwise misexpress an Aiolos gene. The cell preparation can consist of human or non human cells, e.g., rodent cells, e.g., mouse or rat cells, rabbit cells, or pig cells. In preferred embodiments, the cell or cells include an Aiolos transgene, e.g., a heterologous form of an Aiolos gene, e.g., a gene derived from humans (in the case of a non-human cell). The Aiolos transgene can be misexpressed, e.g., overexpressed or underexpressed. In other preferred embodiments, the cell or cells include a gene which misexpress an endogenous Aiolos gene, e.g., a gene the expression of which is disrupted, e.g., a knockout. Such cells can serve as a model for studying disorders which are related to mutated or mis-expressed Aiolos alleles or for use in drug screening.

In another aspect, the invention features, a method of providing an antibody, e.g., a polyclonal or monoclonal antibody. The method includes:

providing a mammal, e.g., a mouse, having a cell which is Aiolos deregulated, e.g., which misexpresses, preferably underexpresses, Aiolos, e.g., a hematopoietic cell; and isolating an antibody from the animal or from a cell derived from the animal, e.g., a hybridoma.

In preferred embodiments: the mammal is immunized with an antigen; the cell is exogenously supplied and one or both of the mammal, or the mammal which donates the cell, are immunized with an antigen. The antigen can be: an alloantigen; a xenoantigen; an autoantigen; a protein; or an antigen which gives rise to an anti-idiotypic lymphocyte. In preferred embodiments the antigen is an autoantigen and the animal is not immunized.

In a preferred embodiment the antigen, e.g., a protein or polypeptide, or an epitope on a protein or polypeptide, is poorly antigenic in wild type animals. Poorly antigenic in wild type animals means that the immune response of a homozygous null Aiolos animal to an antigen is greater than the response to the same antigen in an otherwise similar but Aiolos wild type animal. The immune response can be measured, e.g., as antibody titer in the serum of an animal. The Aiolos response is preferably at least twice, and more preferably at least 10, 50, or 100, -fold greater than that in the wild type animal. Preferably the antigen is conserved between two species, wherein the first species is the animal which provides the antibody and the second species is the species which provides the antigen. In preferred embodiments the antigen has at least 80, 90, 95, 99, or 100% homology between the first and second species, between humans and the animal which supplies the antibody, or between humans and mice.

In preferred embodiments, the antibody is an IgG, IgA, or IgE antibody.

In particularly preferred embodiments, the antibody is an IgG antibody.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated or antibody producing cell, e.g., a lymphocyte.

In preferred embodiments: the proliferation-deregulated or antibody producing cell e.g., a lymphocyte, e.g., a transformed lymphocyte, is isolated from a lymphoma of the mammal.

In preferred embodiments: the mammal carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediate DNA binding of the Aiolos protein or for one or more of the two C terminal zinc finger regions which mediate dimerization of the Aiolos protein; the mammal is heterozygous or homozygous for an Aiolos transgene; the mammal carries a mutation in the control region of the Aiolos gene.

In preferred embodiments the mammal, e.g., a mouse, is homozygous for null mutations, e.g., it is homozygous for a deletion of the C terminal end of the protein, at the Aiolos locus.

In preferred embodiments the mammal, e.g., a mouse, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the mammal carries homozygous mutations at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries homozygous deletions for all or part of exon 7.

In preferred embodiments: the proliferation-deregulated or antibody producing cell is a homozygous mutant Aiolos cell e.g., a lymphocyte; the proliferation-deregulated or antibody producing lymphocyte is a B lymphocyte; the proliferation-deregulated or antibody producing cell is heterozygous or homozygous for an Aiolos transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte. The exogenously supplied cell can be homozygous for null mutations, e.g., homozygous for a deletion of the C terminal end of the protein, at the Aiolos locus. The exogenously supplied cell can be homozygous for null mutations, e.g., homozygous for a deletion of the C terminal end of the protein, at the Aiolos locus and include a mutation at Ikaros, e.g., a dominant negative mutation at Ikaros. Preferably the Ikaros mutaion is heterozygous.

In a preferred embodiment the method further comprises isolating one or more cells, e.g., lymphocytes, from the mammal, and allowing the cell or cells to proliferate into a clonal population of cells, e.g., lymphocytes.

In a preferred embodiment the method further comprises isolating one or more cells, e.g., lymphocytes, from the mammal, and allowing the cell or cells to proliferate into a clonal population of cells, e.g., lymphocytes, and isolating the antibody therefrom.

In preferred embodiments a cell from the animal is fused with a second cell to provide a hybridoma.

In preferred embodiments a cell from the animal is fused with a second cell to provide a hybridoma and the antibody is isolated from the hybridoma.

In preferred embodiments the method further includes providing a lymphocyte e.g., a B lymphocyte, or a substantially homogenous population of lymphocytes, e.g,. B lymphocytes, which produce an antibody molecule, e.g., an IgG, IgA, or IgE molecule, which recognizes a selected antigen.

In preferred embodiments the method further includes providing a lymphocyte e.g., a B lymphocyte, or a substantially homogenous population of lymphocytes, e.g,. B lymphocytes,which produce an antibody molecule, e.g. an IgG, IgA, or IgE molecule, which recognizes a selected antigen, and isolating the antibody therefrom.

In another aspect, the invention features, a method of providing an antibody, e.g., a polyclonal or monoclonal antibody. The method includes:

providing a mammal, e.g., a mouse, having a cell which is homozygous for null or underexpressing mutations at the Aiolos locus; and isolating an antibody from the animal.

In preferred embodiments: the mammal is a non-human mammal, e.g., a swine, a nonhuman primate, e.g., a monkey, a goat, or a rodent, e.g., a rat or a mouse.

In preferred embodiments: the mammal is immunized with an antigen; the cell is exogenously supplied and one or both of the mammal, or the mammal which donates the cell, are immunized with an antigen. The antigen can be: an alloantigen; a xenoantigen; an autoantigen; a protein; or an antigen which gives rise to an anti-idiotypic lymphocyte.

In a preferred embodiment the antigen, e.g., a protein or polypeptide, or an epitope on a protein or polypeptide, is poorly antigenic in wild type animals. Poorly antigenic in wild type animals means that the immune response of a homozygous null Aiolos animal to an antigen is greater than the response to the same antigen in an otherwise similar but Aiolos wild type animal. The immune response can be measured, e.g., as antibody titer in the serum of an animal. The Aiolos response is preferably at least twice, and more preferably at least 10, 50, or 100, -fold greater than that in the wild type animal. Preferably the antigen is conserved between two species, wherein the first species is the animal which provides the antibody and the second species is the species which provides the antigen. In preferred embodiments the antigen has at least 80, 90, 95, 99, or 100% homology between the first and second species, between humans and the animal which supplies the antibody, or between humans and mice.

In preferred embodiments: the mammal carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal carries a mutation in the control region of the Aiolos gene.

In preferred embodiments the mammal, e.g., a mouse, is homozygous for null mutations, e.g., it is homozygous for a deletion of the C terminal end of the protein, at the Aiolos locus.

In preferred embodiments the mammal, e.g., a mouse, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the mammal carries homozygous mutations at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries homozygous deletions for all or part of exon 7.

In preferred embodiments, the antibody is an IgG, IgA, or IgE antibody.

In particularly preferred embodiments, the antibody is an IgG antibody.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte. The exogenously supplied cell can be homozygous for null mutations, e.g., homozygous for a deletion of the C terminal end of the protein, at the Aiolos locus. The exogenously supplied cell can be homozygous for null mutations, e.g., homozygous for a deletion of the C terminal end of the protein, at the Aiolos locus and include a mutation at Ikaros, e.g., a dominant negative mutation at Ikaros. Preferably the Ikaros mutaion is heterozygous.

In preferred embodiments: the mammal which supplies the subject cell is immunized with an antigen. The antigen can be: an alloantigen; a xenoantigen; an autoantigen; a protein; or an antigen which gives rise to an anti-idiotypic lymphocyte.

In preferred embodiments the method further includes providing a lymphocyte e.g., a B lymphocyte, or a substantially homogenous population of lymphocytes, e.g,. B lymphocytes, which produce an antibody molecule, e.g. an IgG, IgA, or IgE molecule, which recognizes a selected antigen.

In another aspect, the invention features, a method of providing an antibody, e.g., a monoclonal antibody. The method includes:

providing a mammal, e.g., a mouse, having a cell which is homozygous for null or underexpressing mutations at the Aiolos locus; and isolating a cell from the animal; and isolating an antibody from the cell or a derivative of the cell, e.g., a hybridoma.

In preferred embodiments: the mammal is immunized with an antigen. The antigen can be: an alloantigen; a xenoantigen; an autoantigen; a protein; or an antigen which gives rise to an anti-idiotypic lymphocyte.

In a preferred embodiment the antigen, e.g., a protein or polypeptide, or an epitope on a protein or polypeptide, is poorly antigenic in wild type animals. Poorly antigenic in wild type animals means that the immune response of a homozygous null Aiolos animal to an antigen is greater than the response to the same antigen in an otherwise similar but Aiolos wild type animal. The immune response can be measured, e.g., as antibody titer in the serum of an animal. The Aiolos response is preferably at least twice, and more preferably at least 10, 50, or 100, -fold greater than that in the wild type animal. Preferably the antigen is conserved between two species, wherein the first species is the animal which provides the antibody and the second species is the species which provides the antigen. In preferred embodiments the antigen has at least 80, 90, 95, 99, or 100% homology between the first and second species, between humans and the animal which supplies the antibody, or between humans and mice.

In preferred embodiments: the mammal is a non-human mammal, e.g., a swine, a nonhuman primate, e.g., a monkey, a goat, or a rodent, e.g., a rat or a mouse.

In preferred embodiments: the mammal carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal carries a mutation in the control region of the Aiolos gene.

In preferred embodiments the mammal, e.g., a mouse, is homozygous for null mutations, e.g., it is homozygous for a deletion of the C terminal end of the protein, at the Aiolos locus.

In preferred embodiments the mammal, e.g., a mouse, is homozygous for null mutations, e.g., it is homozygous for a deletion of the C terminal end of the protein, at the Aiolos locus and includes a mutation at Ikaros, e.g., a dominant negative mutation at Ikaros. Preferably the Ikaros mutaion is heterozygous.

In preferred embodiments: the mammal carries homozygous mutations at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries homozygous deletions for all or part of exon 7.

In preferred embodiments, the antibody is an IgG, IgA, or IgE antibody.

In particularly preferred embodiments, the antibody is an IgG antibody.

In a preferred embodiment the method further comprises isolating one or more cells, e.g., lymphocytes, from the mammal, and allowing the cell or cells to proliferate into a clonal population of cells, e.g., lymphocytes and isolating an antibody from the cells.

In preferred embodiments a cell from the animal is fused with a second cell to provide a hybridoma.

In preferred embodiments a cell from the animal is fused with a second cell to provide a hybridoma and the antibody is isolated from the hybridoma.

In preferred embodiments the method further includes providing a lymphocyte e.g., a B lymphocyte, or a substantially homogenous population of lymphocytes, e.g,. B lymphocytes, which produce an antibody molecule, e.g. an IgG, IgA, or IgE molecule, which recognizes a selected antigen.

In another aspect, the invention features a preparation of an antibody, e.g., a polyclonal or monoclonal antibody, produced by an animal or cell described herein.

In a preferred embodiment the antigen, e.g., a protein or polypeptide, or an epitope on a protein or polypeptide, is poorly antigenic in wild type animals. Poorly antigenic in wild type animals means that the immune response of a homozygous null Aiolos animal to an antigen is greater than the response to the same antigen in an otherwise similar but Aiolos wild type animal. The immune response can be measured, e.g., as antibody titer in the serum of an animal.

The Aiolos response is preferably at least twice, and more preferably at least 10, 50, or 100, -fold greater than that in the wild type animal. Preferably the antigen is conserved between two species, wherein the first species is the animal which provides the antibody and the second species is the species which provides the antigen. In preferred embodiments the antigen has at least 80, 90, 95, 99, or 100% homology between the first and second species, between humans and the animal which supplies the antibody, or between humans and mice.

Cells, e.g., stem cells, treated by the method of the invention can be introduced into mammals, e.g., humans, non-human primates, or other mammals, e.g., rodents. In preferred embodiments the treatment is performed ex vivo and: the cell is autologous, e.g., it is returned to the same individual from which it was derived; the cell is allogeneic, i.e., it is from the same species as the mammal to which it is administered; the cell is xenogeneic, i.e., it is from a different species from the mammal to which it is administered.

Aiolos animals and cells can be used to produce antibodies against antigens that are only poorly antigenic or not antigenic in Aiolos wild type animals.

Aiolos animals and cells can be used to produce IgG antibodies more rapidly than is practical in Aiolos wild type animals.

An Aiolos-deregulated cell is a cell which has a mutant or misexpressed Aiolos gene, e.g., an inactiviated Aiolos gene.

A hematopoietic cell, can be, e.g., stem cell, e.g., a totipotent or a pluripotent stem cell, or a descendent of a stem cell, e.g., a lymphocyte, e.g. a B lymphocyte or a T lymphocyte.

A proliferation-deregulated cell, as used herein, refers to a cell with other than wild An Aiolos misexpressing animal, as used herein, is an animal in which one or more, and preferably substantially all, of the cells misexpress Aiolos.

A mutation at the Aiolos locus, as used herein, includes any mutation which alters the expression, structure, or activity of the Aiolos gene or its gene product. These include point mutations in and in particular deletions of all or part of the Aiolos coding region or its control region.

An exogenously supplied cell, tissue, or cell product, e.g., a cytokine, as used herein, is a cell, tissue, or a cell product which is derived from an animal other than the one to which is supplied or administered. It can be from the same species or from different species than the animal to which it is supplied.

A clonal population of lymphocytes, as used herein, is a population of two or more lymphocytes which have one or more of the following properties: they share a common stem cell ancestor; they share a common pre-thymocyte or pre b cell ancestor; they share a common thymocyte ancestor; they share the same T cell receptor genomic rearrangement; they share a common CD4+CD8+ ancestor; they share a common CD4+ ancestor; they share a common CD8+ ancestor; they share a common CD4−CD8− ancestor; they recognize the same antigen.

A substantially homogenous population of two or more cells e.g., lymphocytes, as used herein, means a population of cells in which at least 50% of the cells, more preferably at least 70% of the cells, more preferably at least 80% of the cells, most preferably at least 90%, 95% or 99% of the subject cell type, e.g., lymphocytes. With respect to the Aiolos locus however, the cells can be all (+/−), all (−/−), or a mixture of (+/−) and (−/−) cells.

Culturing, as used herein, means contacting a cell or tissue with an environment which will support viability of the cell or tissue and which preferably supports proliferation of the cell or tissue.

A substantially purified preparation of cells, e.g., lymphocytes, as used herein, means a preparation of cells in which at least 50% of the cells, more preferably at least 70% of the cells, more preferably at least 80% of the cells, most preferably at least 90%, 95% or 99% of the cells of the subject cell, e.g., are lymphocytes. With respect to the Aiolos locus however, the cells can be all (+/−), all (−/−), or a mixture of (+/−) and (−/−) cells.

Immunocompromised, as used herein, refers to a mammal in which at least one aspect of the immune system functions below the levels observed in a wild-type mammal. The mammal can be immunocompromised by a chemical treatment, by irradiation, or by a genetic lesion resulting in, e.g., a nude, a beige, a nude-beige, or an Ikaros-phenotype. The mammal can also be immunocompromised by an acquired disorder, e.g., by a virus, e.g., HIV.

As used herein, an Aiolos transgene, is a transgene which includes all or part of an Aiolos coding sequence or regulatory sequence. The term also includes DNA sequences which when integrated into the genome disrupt or otherwise mutagenize the Aiolos locus. Aiolos transgenes sequences which when integrated result in a deletion of all or part of the Aiolos gene. Included are transgenes: which upon insertion result in the misexpression of an endogenous Aiolos gene; which upon insertion result in an additional copy of an Aiolos gene in the cell; which upon insertion place a non-Aiolos gene under the control of an Aiolos regulatory region. Also included are transgenes: which include a copy of the Aiolos gene having a mutation, e.g., a deletion or other mutation which results in misexpression of the transgene (as compared with wild type); which include a functional copy of an Aiolos gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Aiolos regulatory region which can (optionally) be operably linked to a nucleic acid sequence which encodes a wild type or mutant Aiolos gene product or, a gene product other than an Aiolos gene product, e.g., a reporter gene, a toxin gene, or a gene which is to be expressed in a tissue or at a developmental stage at which Aiolos is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Aiolos sequence. Preferably, the transgene includes a deletion of all or some of exons 3 and 4, or a deletion for some or all of exon 7 of the Aiolos gene.

A "heterologous promoter", as used herein is a promoter which is not naturally associated with the Aiolos gene.

A "purified preparation" or a "substantially pure preparation" of an Aiolos polypeptide, or a fragment or analog thereof (or an Aiolos-Aiolos or Aiolos-Ikaros dimer), as used herein, means an Aiolos polypeptide, or a fragment or analog thereof (or an Aiolos-Aiolos or Aiolos-Ikaros dimer), which is free of one or more other proteins lipids, and nucleic acids with which the Aiolos polypeptide (or an Aiolos-Aiolos or Aiolos-Ikaros dimer) naturally occurs. Preferably, the polypeptide, or a fragment or analog thereof (or an Aiolos-Aiolos or Aiolos-Ikaros dimer), is also separated from substances which are used to purify it, e.g., antibodies or gel matrix, such as polyacrylamide. Preferably, the polypeptide, or a fragment or analog thereof (or an Aiolos-Aiolos or Aiolos-Ikaros dimer), constitutes at least 10, 20, 50 70, 80 or 95% dry weight of the purified preparation. Preferably, the preparation contains: sufficient polypeptide to allow protein sequencing; at least 1, 10, or 100 μg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

A "substantially pure nucleic acid", e.g., a substantially pure DNA encoding an Aiolos polypeptide, is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional Aiolos sequences.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). The determination of percent homology between two sequences can be accomplished using a mathematical algorithim. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Programs which are equivalent in terms of the results they produce can be used.

The terms "peptides", "proteins", and "polypeptides" are used interchangeably herein.

As used herein, the term "transgene" means a nucleic acid sequence (encoding, e.g., by one or more Aiolos polypeptides or Aiolos-Ikaros dimers), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence, such as the Aiolos and/or Ikaros gene, operably linked to the promoter, and which effects expression of the selected DNA sequence in specific cells of a tissue, such as lymphocytes. The term also covers so-called "leaky" promoters, which regulate expression of a selected DNA primarily in one tissue, but cause expression in other tissues as well.

A polypeptide has Aiolos biological activity if it has one or more of the following properties: (1) the ability to react with an antibody, or antibody fragment, specific for (a) a wild type Aiolos polypeptide, (b) a naturally-occurring mutant Aiolos polypeptide, or (c) a fragment of either (a) or (b); (2) the ability to form Aiolos dimers and/or Aiolos/Ikaros dimers; (3) the ability to modulate lymphocyte differentiation; (4) the ability to stimulate transcription from a sequence, e.g., a sequence described herein; or (5) the ability to act as an antagonist or agonist of the activities recited in (1), (2), (3) or (4).

"Misexpression", as used herein, refers to a non-wild type pattern of Aiolos gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-transitional modification, stability, or biological activity of the expressed Aiolos and/or Ikaros polypeptide; a pattern of expression that differs from wild type in terms of the effect of an environmental stimulus or extracellular stimulus on expression of the Aiolos and/or Ikaros gene, e.g., a pattern of increased or decreased expression (as compared with wild type)in the presence of an increase or decrease in the strength of the stimulus; a ratio of Ikaros-Ikaros dimer to Aiolos-Aiolos dimer which differs from wild type; a ratio of Aiolos to Aiolos-Aiolos dimer, Ikaros-Ikaros dimer, or Ikaros-Aiolos dimer that differs from wild type; a ratio of Ikaros-Aiolos dimer to Aiolos, Ikaros, Aiolos-Aiolos dimer, or Ikaros-Ikaros dimer that differs from wild type.

As described herein, one aspect of the invention features a pure (or recombinant) nucleic acid which includes a nucleotide sequence encoding an Aiolos, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for an Aiolos polypeptide. Equivalent nucleotide sequences will include sequences that differ by one or more nucleotide substitutions, additions or deletions, such as allelic variants, and will, therefore, include sequences that differ from the nucleotide sequence of Aiolos shown in SEQ ID NO:1 or SEQ ID NO:7 due to the degeneracy of the genetic code.

An Aiolos-responsive control element, as used herein is a region of DNA which, when present upstream or downstream from a gene, results in regulation, e.g., increased transcription of the gene in the presence of an Aiolos protein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity.

An Aiolos-deregulated animal, is an animal in which the physiological function of the Aiolos protein is inhibited and deregulated B cell responses, e.g., production of autoantibodies, are manifested. The physiological function of an Aiolos protein can be inhibited by, for example, inhibiting the Aiolos protein from binding to DNA or heterodimerizing with another Ikaros family member, e.g., an Ikaros protein; or misexpressing the Aiolos gene, e.g., by altering the expression, structure, or activity of the Aiolos gene or its gene product. Aiolos can also be deregulated by introducing into an animal, e.g., an Aiolos wild type animal, an Ikaros dominant negative mutation. The mutant Ikaros proteins can lower the number of active or available Aiolos molecules.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The Aiolos genes and polypeptides of the present invention are useful for studying, diagnosing and/or treating diseases associated with unwanted cell proliferation, e.g., leukemias or lymphomas. The gene (or fragment thereof) can be used to prepare antisense constructs capable of inhibiting expression of a mutant or wild type Aiolos gene encoding a polypeptide having an undesirable function. Alternatively, an Aiolos polypeptide can be used to raise antibodies capable of detecting proteins or protein levels associated with abnormal cell proliferation or lymphocyte differentiation, e.g., T cell maturation. Furthermore, Aiolos peptides, antibodies or nucleic acids, can be used to identify the stage of lymphocyte differentiation, e.g., the stage of T cell differntiation.

Other features and advantages of the invention will be apparent from the following detailed description, and from the claims.

IN BRIEF DESCRIPTION OF THE FIGURES

FIG. 1 is a diagram depicting mouse Aiolos cDNA. 1A: is a mouse Aiolos cDNA nucleotide sequence (SEQ ID NO:1). 1B: is a corresponding amino acid sequence 507 amino acids in length (SEQ ID NO:2).

FIG. 2 is a diagram depicting homology at the amino acid level between the mouse (amino acid residues 275 to 507 of SEQ ID NO:2) and chicken (SEQ ID NO:30) Aiolos sequence and the mouse (amino acid residues 283 to 518 of SEQ ID NO:27) and chicken Ikaros exon 7 (SEQ ID NO:31) sequence.

FIG. 3 is a diagram depicting the homolgy between mouse Aiolos amino acid sequence (amino acid residues 109 to 305 of SEQ ID NO:2) and mouse Ikaros amino acid sequence (amino acid residues 1 to 310 of SEQ ID NO:27).

FIG. 4 is a diagram depicting Aiolos exons (exon 3: SEQ ID NO:32; exon 4: SEQ ID NO:33; exon 5: SEQ ID NO:34; exon 6: SEQ ID NO:18; exon 7: SEQ ID NO:36). Based on homology to Ikaros, the exons encoding different segments of the Aiolos gene are deduced. The exon boundaries of exons 5/6 and 6/7 have been confirmed from genomic sequence (6/7) or from differential splice products (5/6). Three classes of cDNA were recovered. The first contains exons 3 though 7. A second class splices exon 5 directly to exon 7, skipping exon 6. The third contains exon 7 and contiguous genomic sequence extending upstream of this exon.

FIG. 5A: is a human Aiolos cDNA nucleotide sequence. Consensus sequence of human Aiolos cDNA from RTPCR using mouse AioF primer (ex3) in forward direction and human hAio2 primer (ex6) in reverse direction. This sequence does not include the AioF primer sequence but does include the hAio2 sequence. AioF=atg aaa gtg aaa gat gaa tac agc (SEQ ID NO:38) only human sequence is shown here. EcoRI sites flank directly 5' and 3'. The cDNA sequence in FIG. 5A is SEQ ID NO: 7. 5B: shows a corresponding human amino acid sequence 209 amino acids in length (SEQ ID NO:8). 5B also shows the corresponding mouse sequence and shows regions of shared sequence (amino acid residues 66 to 273 of SEQ ID NO:2). The consensus sequence in 5B is SEQ ID NO:37.

FIG. 6 is a diagram depicting comparison of the amino acid sequence of Aiolos (top sequence; SEQ ID NO:2) and Ikaros (bottom sequence; SEQ ID NO:27) proteins. The boxed methionines represent the three translation initiation codons. The boxed cysteines and histidines represent the paired cysteines and histidines of the zinc finger motifs. The conserved activation domain (amino acids 290–344 of Aiolos protein) is shaded. Identical residues are indicated by bars and conservative residues are indicated by dots.

DETAILED DESCRIPTION OF THE INVENTION

Overview

Figure 7:
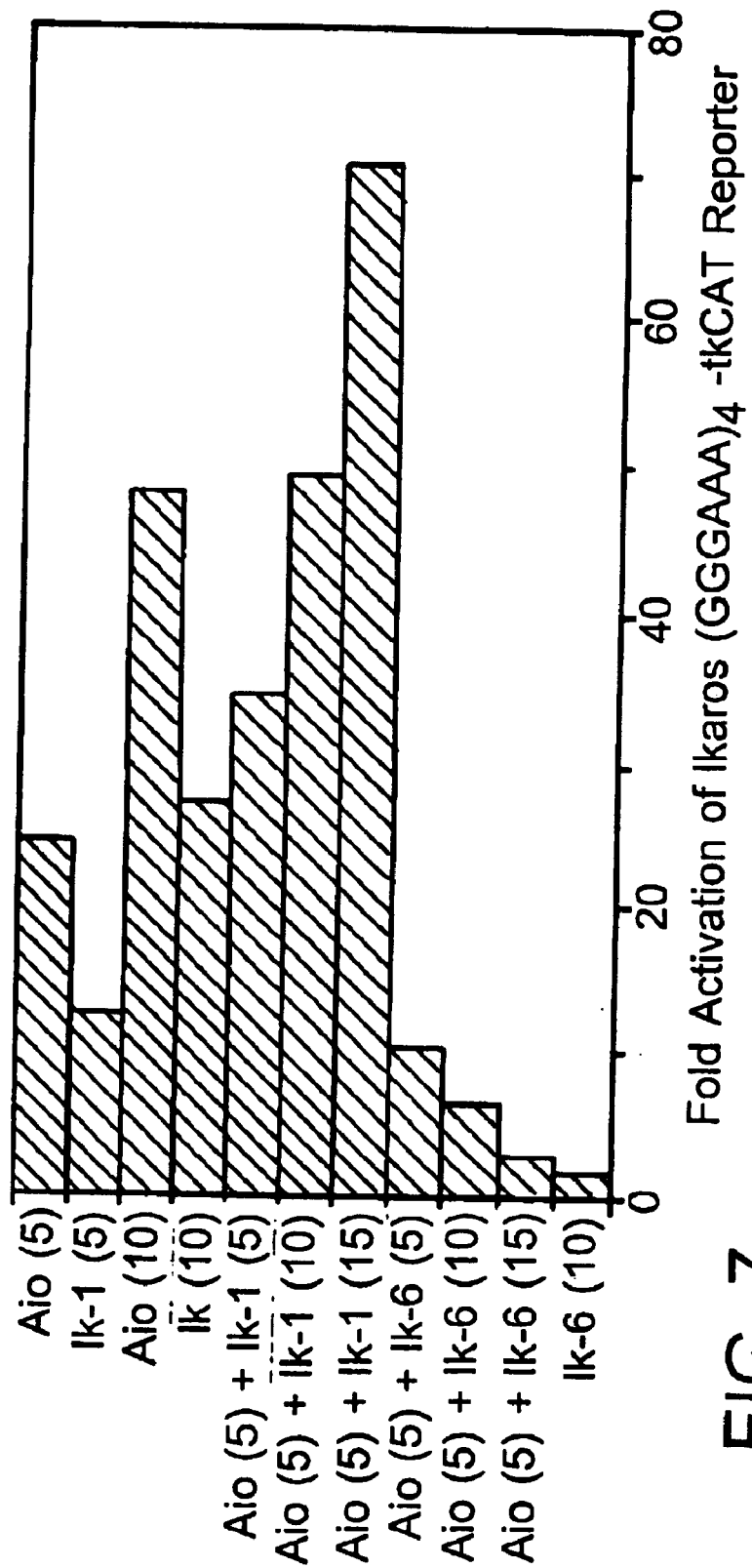
FIG. 7 is a bar graph depicting the effect of different isoforms on the transcriptional activation of Ikaros.

The development of lymphocytes is dependent on the activity of the zinc finger transcription factor Ikaros (Georgopoulos et al. (1992) *Science* 258, 808; Georgopoulos et al. (1994) *Cell* 79, 143; Molnar et al. (1994) *Mol. Cell Biol.* 14 8292; and Kaham et al. (1994) *Mol. Cell Biol.* 14, 7111). Ikaros mutant phenotypes suggest that this protein acts in concert with another protein with which it dimerizes. The Aiolos gene encodes a transcription factor which is homologous to Ikaros and can form dimers with it. In contrast to Ikaros which is expressed in pluripotent stem cells, Aiolos expression is first detected in committed lymphoid progenitors and increases as T and B cells mature. The expression patterns of Aiolos and Ikaros, the relative transcriptional activity of homo- and heterodimers of these proteins, and the dominant interfering effect of mutant Ikaros isoforms on the Aiolos activity suggest that Aiolos is an important regulator of lymphoid development. Thus, varying levels of Ikaros and Aiolos homodimers as well as heterodimers between these proteins modulate gene expression and regulate progression through the lymphoid lineages.

These examples are described in more detail herein.

Ikaros and Aiolos

The Ikaros gene encodes, by alternate splicing, a family of zinc finger transcription factors which are essential for development of the lymphopoietic system (Georgopoulos et al. (1992) *Science* 258, 808–812; Georgopoulos et al. (1994) *Cell* 79 143–156; Molnar et al. (1994) *Mol. Cell. Biol.* 14 8292–8303; and Hahm et al. (1994) *Mol. Cell Biol.* 14, 7111–7123). Ikaros expression is first detected in pluripotentient hemopoeitic stem cells and expression is maintained through all stages of lymphoid development. Mice homozygous for a deletion of the region encoding the Ikaros DNA binding domain lack committed progenitors as well as mature T and B lymphocytes and natural killer cells. (Georgopoulos et al. (1994) *Cell* 79, 143–156). In addition to this apparent role in the early development of lyphoid progenitors, Ikaros is also required for later events during T cell maturation (Winandy et al. (1995) *Cell* 83 289–299). Mice heterozygous for this Ikaros mutation generate T cells which proliferate abnormally. They develop lymphoproliferative disorders and ultimately die of T cell leukemias and lymphomas.

The Ikaros protein isoforms all share a common C-terminal domain containing two zinc fingers to which different combinations of N-terminal zinc fingers are appended. The N-terminal zinc fingers are required for sequence specific DNA binding while the C-terminal zinc fingers mediate homo- and heterodimerization among the Ikaros isoforms (Molnar et al. (1994) *Mol. Cell. Biol.* 14 8292–8303. Homo- and heterodimerization or isoforms which contain a DNA-binding domain greatly increases their affinity for DNA and their transcriptional activity. Heterodimers containing one isoform which lacks a DNA binding domain are transcriptionally inert. Hence such isoforms can interfere with the activity of Ikaros isoforms which contain a DNA binding domain in a dominant negative fashion.

The C-terminal domain shared by all of the Ikaros isoforms was targeted by deletion in the mouse germ line. Mice homozygous for this mutation display a phenotype which is less severe than that caused by deletion of the DNA binding domain. The C-terminal Ikaros mutant mice lack most lymphocytes and NK cells but they do develop $\alpha\beta$ T cells. The milder phenotype may be due to a low level of activity retained in the proteins generated by the C-terminal Ikaros mutant allele. Alternatively, the C-terminal mutation could be the equivalent of a null for Ikaros activity while the more severe phenotype of the N-terminal deletion mutant may be explained by a dominant interfering effect of the Ikaros isoforms produced by the mutant allele on the activity of some other protein which is also required for commitment to and differentiation of the $\alpha\beta$ T lineage. The dominant negative influence of these proteins on other Ikaros isoforms with an intact DNA binding domain has been demonstrated by in vitro and in vivo assays. Since the zinc fingers in the Ikaros C-terminal domain display strong homology to the C-terminal zinc fingers of the Drosophila suppressor protein Hunchback (Tautz et al. (1987) *Nature* 327, 383) it appears that this domain existed prior to the expansion of the vertebrate genome and may be included in other proteins as well. Such proteins would have the potential to interact with Ikaros proteins when co-expressed and would be candidate targets for the dominant negative activity of the truncated Ikaros isoforms.

Degenerate oligonucleotides were used to amplify the C-terminal zinc finger domain from the mouse genome. Among the genes identified was Aiolos, a homolog of Ikaros whose expression is restricted to lymphoyed lineage. The Aiolos protein showes extensive homology to the largest Ikaros isoform, Ik-1, throughout the DNA binding and C-terminal domains and can form homodimers and heterodimers with the Ikaros proteins. Aiolos homodimers are potent transcriptional activators while heterodimers between Aiolos and different Ikaros isoforms range in activity from slightly less potent to transcriptionally inert. Unlike Ikaros, Aiolos is not expressed in the hematopoietic stem cell compartment. Its expression is first detected at low levels in lymphoyed progenitors and is trongly upregulated at the stage when rearrangement of T and B antigen receptors occurs. Thus, heterodimers of Aiolos and Ikaros are essentisal for the normal maturation of lymphocytes. The profound effects of the Ikaros DNA binding mutation reflect interference with the normal activity of both Aiolos and Ikaros during lymphocyte development.

Cloning of the Aiolos cDNA

In order to identify Ikaros homologs, degenerate primers were constructed to the sequences conserved between mouse Ikaros and Drosophila hunchback proteins (PCR primers: Deg 3 TAC/TACCATC/TCACATGGGCTG/ACCA (SEQ ID NO:3) starting at residue 1278 of SEQ ID NO:1 and Deg 4 G/ACCA/GCACATGTTG/ACACTC/TG/AAA (SEQ ID NO:4) starting at residue 1339 of SEQ ID NO:1. PCR was performed on chicken genomic DNA and products of the expected size (61 bp) were purified on a low melt agarose gel and subcloned into PCR2 vector (Invitrogen). Nucleotide sequence demonstrated that these clones fell into three classes. Phage containing the genomic sequence encoding these fragments were isolated from a genomic DNA library and the regions flanking the amplified fragments were sequenced. Analysis of this sequence demonstrated that one class of the clones represented the chicken homologue of Ikaros, while a second class represented the corresponding exon from a highly homologous gene, designated Aiolos (FIG. 2). Aiolos cDNA was isolated from a mouse spleen cDNA library using a probe spanning residues 796–1156 of SEQ ID NO:1. Clones isolated from this library fall into three classes representing alternative RNAs derived from Aiolos gene (FIG. 4). The corresponding genomic region was isolated by hybridization to probes spanning residues 1–650 and 796–1156 of SEQ ID NO:1. The mouse Aiolos cDNA nucleotide and corresponding amino acid sequence is given in FIG. 1.

Isolation of Human Aiolos

Partial human Aiolos cDNAs were isolated by PCR amplification using mouse Aiolos primers AioC (SEQ ID NO:5) and AioA (SEQ ID NO:6), which are in mouse Aiolos exons 2 and 7, respectively. The nucleotide sequence of the longest of these cDNAs and the deduced amino acid sequence are presented in FIG. 5 and correspond to SEQ ID NO:7 and SEQ ID NO:8, respectively. The sequence does not include the primers used for the amplification.

Isolation of Aiolos cDNA from Other Species

One of ordinary skill in the art can apply routine methods to obtain Aiolos cDNA from yet other species. The experiments described above outline isolation of Aiolos cDNA from mouse, chicken, and human. The Aiolos cDNA can be isolated from other species, e.g., from bovine, by methods analogous to those described above. For example, the bovine Aiolos cDNA can be isolated by probing a bovine spleen or thymus cDNA or genomic library with a probe homologous to mouse or human Aiolos cDNA described above.

Alternative Splice Forms of Aiolos

PCR was used to determine whether alternative splice forms of Aiolos exist. Primer combinations AioC/AioA, Aio4F/AioA, and Aio5F/AioA were used to examine the possibility of alternate splicing of the Aiolos mRNA. AioC anneals within exon 3, Aio4F within exon 4, Aio5F within exon 5, and AioA within exon 7. The primer sequences are the following:

AioC GTG TGC GGG TTA TCC TGC ATT AGC (SEQ ID NO:5)

AioF GTA ACC TCC TCC GTC ATA TTA AAC (SEQ ID NO:9)

Aio5F CGA GCT TTT CTT CAG AAC CCT GAC (SEQ ID NO:10)

AioA ATC GAA GCA GTG CCG CTT CTC ACC (SEQ ID NO:6)

Isoforms lacking exon 6 have been identified to date at a low abundance.

Functional Domains are Conserved Between Aiolos and Ikaros Proteins

Aiolos cDNA contains an open reading frame of 1521 nucleotides encoding a 58 KD protein with 70% similarity to Ikaros (FIG. 6).

The general structure of Aiolos and Ikaros proteins is very similar, and four blocks of sequence are particularly well conserved. The first block of conservation encodes the zinc finger modules contained in the Ik-1 isoform which mediate DNA binding of the Ikaros protein (Molnar et al. (1994) *Mol. Cell. Biol.* 14 8292–8303). The second block of conservation has not been characterized functionally. The third block of conservation is a domain required for transcriptional activation by Ikaros (this domain is boxed in FIG. 6). The fourth block of conservation corresponds to the zinc fingers which mediate dimerization.

Antibodies generated against two Aiolos peptides (amino acids 1–124 and amino acids 275–448) indicate that Aiolos polypeptide is approximately the same size as Ik-1 protein, i.e., approximately 57 kDa in size.

The structure and function of the Aiolos zinc finger domains are homologous with the zinc finger domains of Ikaros. Aiolos has four C terminal domains which mediate the binding of Aiolos to DNA and two C terminal regions which mediate the formation of Aiolos dimers.

Two Highly Conserved C-terminal Zn Finger Motifs Mediate Interactions Between Aiolos and Ikaros Proteins The ability of the Aiolos zinc finger domain to engage in protein interactions was tested in a yeast two hybrid assay (Zervos et al. (1993) *Cell* 72, 223; and Gyuris et al. (1993) *Cell* 75, 1).

Segments of 500 nucleotides of the Aiolos or Ikaros cDNAs encoding the C-terminal 149 and 154 amino acids of these proteins, respectively, were inserted in the bait vector pLex202 to created in frame fusions with the LexA DNA binding domain (Ik-500 and Aio-500, respectively). The B42 transcriptional activation domain in the pGJ prey vector was fused in frame to the full length Ikaros and Aiolos proteins as well as the following fragments of the cDNAs: the first five coding exons of Ik-1(Ik-N); the 500 nucleotides segments-used to construct the bait constructs (Aio-500 and Ik-500); the entire coding sequence of the C-terminal exon of Aiolos (Aio-800) encoding a 232 amino acid long sequence; the full length Ikaros protein with point mutations in either the penultimate (M1) or ultimate (M2) zinc fingers, or both (M1+M2). Combinations of Aiolos and Ikaros bait and prey vectors were transformed into the EGY48 yeast strain. EGY48 (MATa trp1 ura3 his3 LEU2. pLexAop6-LEU2) has a Leu2 gene as well as the pJK103 plasmid harboring the lacZ gene under the control of two high affinity ColE1 LexA operators maintained under Ura3 selection. Growth of yeast cells on Ura⁻ His⁻ Trp⁻ Leu⁻-galactose plates and color development on Ura⁻ His⁻ Trp⁻-X-gal-galactose plates were used to score Aiolos and Ikaros protein interactions. Interactions between Aiolos and Ikaros baits and preys in the yeast two hybrid system result in the transcription of β-galactosidase and the production of blue colonies on X-gal indicator plates. Strong interactions between prey and bait recombinant proteins result in expression of both the Leu-2 and β-glactosidase genes.

The results are presented in Table I. The rate at which transformed yeast colonies turn blue on indicator plates suggests that the affinities of Aiolos for itself and for Ikaros protein are similar (+++). White colonies indicate a lack of interaction (−). A domain in the Aiolos protein that contains the last two Krülppel-like zinc fingers (Aio-500) interacts with itself either as an isolated domain (Aio-500, Aio-800) or in the context of the full length protein (Aiolos). Similar interactions were observed with the analogous Ikaros domain (Ik-500), either alone or in the context of the full length protein (Ikaros). Mutations in the Ikaros zinc finger motifs (M1, M2 and M1+M2) which abrogate Ikaros dimerization also abrogated Aiolos-Ikaros protein interactions. In contrast to the C-terminal fingers, the N-terminal finger motifs (Ik-N) were not capable of mediating such protein interactions. PJG is the prey vector used as a negative control. In a similar fashion, the equivalent Ikaros bait (154 aminoacids in size), Ik-500, interacted with recombinant prey proteins that contained either the C-terminal domain of Aiolos or Ikaros or the full length proteins. Ik-500 was, similarly to Aio-500, unable to interact with the interaction incompetent Ikaros mutants. In this assay, the affinities of Aiolos for itself or Ikaros were similar and indistinguishable to that of Ikaros for itself.

TABLE I

| | BAIT | |
|---|---|---|
| | Aiolos-500 | Ikaros-500 |
| PREY | | |
| Aiolos | +++ | +++ |
| Aio-500 | +++ | +++ |
| Aio-800 | +++ | +++ |
| Ikaros | +++ | +++ |
| Ik-500 | +++ | +++ |
| Ik-N | − | − |
| Ikaros M1 | − | − |
| Ikaros M2 | − | − |
| Ikaros M1 + M2 | − | − |
| pJG | − | − |

Thus, this example shows that the C-terminal zinc fingers of Aiolos and Ikaros mediate protein dimerizations and that Aiolos and Ikaros can homodimerize and heterodimerize.

Aiolos and Ikaros Heterodimerize In Vivo

Heterodimers of Aiolos and Ikaros proteins were observed in transfected mammalian cells. Heterodimerization was shown by coimmunoprecipitations of the two proteins and by showing that both proteins localize to the same region in a cell.

Interactions between Aiolos and Ikaros proteins were confirmed by coimmunoprecipitations. Aiolos-(Flag) protein (10) and Ikaros protein (Ik-1), or a mutant Ikaros protein having point mutations in the zinc finger domain which prevents Ikaros homodimerization (IkM) were expressed in the epithelial cell line 293T and immunoprecipitated using an antibody to the Flag epitope (6, Eastman Kodak). Immunoprecipitates were run on a 10% SDS gel and analyzed by Western blotting with an Ikaros antibody. No Ikaros was observed in immunoprecipitates from untransfected controls. To confirm the levels of Ikaros and Aiolos protein produced in the transfected cells, Westerns on total protein were performed with the Ikaros and Flag antibodies. Similar amounts of Ik-1 or IkM and Aiolos proteins were produced in the transfected cell populations.

The results indicate that Ikaros protein coprecipitates with Aiolos upon immunoprecipitation of Aiolos-(FLAG) with an antibody to the tagged Aiolos protein. However, the dimerization mutant IkM was not coprecipitated with Aiolos-(FLAG). Thus, these results indicate that Aiolos and Ikaros heterodimerize in vivo.

Aiolos and Ikaros also co-localize in the nucleus of cells. Subcellular localization of Aiolos protein was determined upon its expression in NIH-3T3 fibroblasts. NIH-3T3 fibroblasts were transfected with one or more of expression vectors encoding Aiolos-(FLAG), Ikaros Ik-1 or Ik-6. The Ik-6 isoform of Ikaros lacks a DNA binding domain and is normally found in the cytoplasm. The FLAG epitope was detected with a the same anti-FLAG monoclonal antibody described above and a secondary goat anti-mouse IgG antibody conjugated to rhodamine (Boehringer Mannheim). NIH-3T3 fibroblasts transfected with Aiolos and Ikaros expression vectors were stained with anti-FLAG and rhodamine conjugated goat anti-mouse and with anti-Ikaros and goat anti-rabbit IgG FITC sequentially. No crossreactivity between preadsorbed secondary antibodies was detected. Cells were counterstained with hoechst 33258 for one hour in PBS at 1 µg/mi.

The results show that the Aiolos protein, tagged with the FLAG epitope (Hopp et al. (1988) *Biotech* 6, 1204–1210) is found in the nucleus when expressed in fibroblast cells. Immunofluorescence staining for either Aiolos or Ikaros proteins revealed a punctuate pattern of staining similar to that observed with polycomb proteins, some splicing factors, and the GATA proteins (Messmer et al. (1992) *Genes & Dev* 6, 1241–1254; Colwill et al (1996) *EMBO J* 15, 65–275; and Elefanty et al. (1996) *EMBO J* 15, 319–333). When Aiolos is coexpressed with an Ikaros isoform that is localized in the nucleus, e.g., Ik-1, both proteins are detected within the same region of the nucleus. In fact, the red and green signals of the labels generate a yellow signal, confirming the co-localization of these proteins. Interestingly, when Aiolos is coexpressed with an Ikaros isoform that is localized in the cytoplasm, e.g., Ik-6, both proteins co-localize to the nucleus.

Conserved Function of the N-terminal Zinc Finger DNA Binding Domain in Aiolos and Ikaros Proteins Contacts between DNA and the alpha helical region in the C-terminal half of Kruppel-like zinc fingers are important in determining the sequence specificity of these interactions (Lee et al. (1989) *Science* 245, 635 and Pavletich et al. (1993) *Science* 261: 1701). The regions that bind DNA are perfectly conserved between Aiolos and Ikaros (FIG. 6). This example demonstrates that both proteins are capable of binding the same DNA sequences.

DNA binding assays (EMSA) were performed essentially as described in Molnar et al. (1994) *Mol. Cell. Biol.* 14, 8292–8303. GST-Aiolos and Ikaros fusion proteins and their GST fusion partner (0.5 µg) were tested for binding to the IKBD1-TCAGCTTTTGGGAATACCCTGTCA (SEQ ID NO:11) oligonucleotide which contains a high affinity Ikaros binding site (100,000 cpm/reaction which equals 1 to 2 ngs of DNA). Competition assays were performed with Ik-BS1 and with Ik-BS8 TCAGCTTTTGGGggTACCCTGTCA (SEQ ID NO:12) oligonucleotides used at 5–100×molar excess.

The results of these binding assays show that high affinity complexes are formed between an Aiolos-GST fusion protein and an oligonucleotide containing a binding site for the Ik-1 protein. Hence Aiolos and Ikaros can, in principle, compete for similar binding sites in the genome.

Aiolos is a More Potent Transcriptional Activator than Ikaros

Ikaros and Aiolos share a highly conserved 81 amino acid sequence which has been shown to mediate transcriptional activity of the Ikaros proteins. This activation domain of Ikaros is composed of a stretch of acidic amino acids followed by a stretch of hydrophobic residues, both of which are required for its full activation potential. This domain from Ikaros alone or the full length Ikaros protein confers transcriptional activity of a fusion protein with the LexA DNA binding domain. This example shows that the homologous domain in Aiolos is also a transcriptional activation domain in yeast and mammalian cells and that the Aiolos transcriptional activation domain provides stronger transcriptional activity than the homologous domain from Ikaros in mammalian cells.

The C-terminal domains of Aiolos and Ikaros were tested for their ability to activate transcription in yeast. For this example, expression constructs encoding the 232 and 149 C-terminal amino acids of Aiolos and fused to the LexA DNA binding domain were prepared, and termed Aio-800 and Aio-500, respectively. Expression constructs encoding the 232 and 154 most C-terminal residues of Ikaros fused to the LexA DNA binding domain were also prepared, and termed Ik-800 and Ik-500, respectively. These expression constructs were transformed into the EGY48 yeast strain. EGY48 (MATa trp1 ura3 his3 LEU2: pLexAop6-LEU2) has a Leu2 gene as well as the pJK103 plasmid harboring the lacZ gene under the control of two high affinity ColE1 LexA operators maintained under Ura3 selection. The recombinant proteins were tested for their ability to activate the Leu 2 gene and the lacZ genes using Ura$^-$ His$^-$ Leu$^-$-glucose and Ura$^-$ His$^-$ Leu$^-$-X-gal-glucose selections, respectively.

The results show that the 232 C-terminal amino acids of Aiolos fused to the LexA DNA binding domain activated strong expression of both the Leu-2 and β-galactosidase genes in the yeast one hybrid system. No activity was detected with the 149 most C-terminal amino acids of Aiolos, which do not contain the conserved domain, in either assay. Thus, the protein domain in Aiolos, which is closely related in amino acid sequence to the transcriptional activation domain of Ikaros, is also capable of conferring transcriptional activation in yeast cells.

Although Aiolos and Ikaros display similar activities in yeast, Aiolos is a stronger activator in mammalian cells. In this example, Aiolos and the Ikaros isoforms Ik-1 and Ik-6 were co-transfected at different ratios together with the Ikaros-tkCAT reporter gene in NIH-3T3 cells as follows.

The ability of Aiolos homo- and Aiolos-Ikaros heterodimers to stimulate CAT activity from the Ikaros reporter plasmid 4xIK-BS1-tkCAT was determined in transient expression assays in NIH-3T3 fibroblast cells. NIH-3T3 cells in 100 mm dish were co-transfected with the reporter plasmid 4xIk-BS1-tkCAT, containing 4 copies of a single high affinity Ikaros binding site or tkCAT (4 µgs), with Aiolos and or Ikaros recombinant CDM8 expression vectors (5–15 µgs) and with the pxGH5 (4 µgs), a plasmid encoding the growth hormone which is used as an internal control of transfection. CDM8 was used to supplement amounts of expression vector DNA to 20 µgs. Each transfection point was performed in triplicate or quadriplicate. 48 hours after-transfection CAT and growth hormone (GH) assays were performed on cell lysates and supernatants respectively. Transfection efficiencies were normalized by growth hormone levels. Part of the cell pellet was lysed in protein sample buffer and used for Western analysis to determine Aiolos and Ikaros protein expression in transfected fibroblasts. The amount of protein was determined using Ikaros and Flag antibodies. The activities of Aiolos with or without the Flag epitope were indistinguishable in this assay. Co-transfections of the reporter plasmids with CDM8 vector alone were performed to establish the base level for CAT activity. Up to 5% variability was detected between transfections performed in triplicate.

The results are presented in FIG. 7. Aiolos and Ikaros proteins were expressed at similar levels, but the levels of CAT activity elicited by Aiolos were higher than those observed with Ik-1, the most pot activator of the Ikaros isoforms. In fact, Aiolos stimulated CAT activity by 25–50 fold, whereas Ik-1 elic a 12–25 fold increase in expression in this assay. Co-expression of Ikaros and Aiolos proteins stimulated expression of the reporter gene to levels intermediate between those seen with Aiolos or Ikaros homodim (e.g., compare Aiolos [10] versus Aiolos[5]+Ik-1 [5] versus Ik-1 [10]).

Ikaros isoforms which lack a DNA binding domain interfere with the transcriptional activity of Aiolos proteins when both are expressed in the same cell (FIG. 7, Aio+Ik-6). Similar results were obtained when Ikaros isoforms with and without a DNA binding domain were co-expressed. Heterodimers of the interfering Ikaros isoforms with other Ikaros proteins do not bind DNA. The dramatic decrease in Aiolos activity is most probably due to the formation of Aiolos-Ikaros heterodimers that do not bind DNA and therefore cannot activate transcription. Transfection with equimolar amounts of Aiolos and the Ik-6 isoform leads to the 65% reduction in CAT activity expected if Aiolos/Ik-6 heterodimers are transcriptionally inert. Addition of higher levels of Ik-6 further reduces transcription of the reporter gene. This effect is specific for the interfering isoform since addition of similar amounts of activating isoforms leads to a linear increase in transcriptional activity (FIG. 7, Aio(5)+ Ik-1 (5)–(15)).

Therefore, Aiolos homodimers can compete with Ikaros homodimers for binding sites and can stimulate transcription to higher levels. The difference in activity of the two proteins can be accounted for by additional protein interactions that take place with a domain of the Ikaros proteins which is not conserved in Aiolos. Such protein interactions may specifically modulate the activity of Ikaros in mammalian cells during development without affecting Aiolos directly.

Aiolos Expression is Restricted to the Lymphoid System

This example shows that in the adult mouse, Aiolos transcripts are detected exclusively in lymphoid tissues.

Total RNAs (10–20 $\mu$gs) from thymus, spleen, bone marrow, brain, heart, kidney and liver of wild type mice and from bone marrow of mice homozygous for a mutation in the Ikaros DNA binding domain were used for Northern analysis. RNA purification and Northern analysis were performed as previously described (Georgopoulos et al. (1992) Science 258, 808–812). A 330 bp fragment derived from the last translated exon of Aiolos which does not cross-react with Ikaros sequences was used as a probe to detect Aiolos transcripts of 4.5 and 9 kb.

The results of the Northern blot hybridizations indicate that Aiolos expression levels are highest in the spleen, progressively lower in the thymus and bone marrow, and are undetectable in non-lymphoid tissues such as brain, heart, kidney or liver of a wild type mouse. The spleen is largely populated by mature B and T lymphocytes, while the majority of cells in the thymus are immature CD4+/CD8+ thymocytes which are in the process of rearranging their T antigen receptors. In the bone marrow, approximately 25% of the cells are pre-B cells at a stage of differentiation comparable to that of double positive thymocytes while the rest are predominantly erythroid and myeloid precursors (Hardy et al. (1991) J. Exp. Med. 173, 1213–1225). Aiolos mRNAs were not detected in the bone marrow of Ikaros mutant mice which is largely comprised of erythroid and myeloid cells and lacks detectable numbers of committed lymphoid precursors. These observations indicate that Aiolos is expressed in committed precursors of the B and T lineage and is upregulated upon their terminal differentiation.

Further information on Aiolos expression was obtained through in situ hybridization. Sections were prepared from E-12 to E-16 embryos as previously described (Georgopoulos et al. (1992) Science 258, 808–812). These were incubated with Ikaros or Aiolos specific $^{32}$P-UTP RNA sense and antisense probes at 51° C. for 12–16 hours. The Ikaros probe was 300 bp in size generated from the 3' untranslated region of its last exon. The Aiolos probe was generated from the first 330 bp of its last translated exon which show little homology to Ikaros sequences. Slides were washed with 0.5×SSC/0.1% SDS at 55° C. and at 65° C., dehydrated and dipped in diluted photographic emulsion (NBT2). Dipped slides were exposed for 4 weeks, developed, stained with hematoxylin and cosin and analyzed by bright and dark field illumination on an Olympus microscope.

In situ hybridization to embryo sections indicated that Ikaros is expressed at the earliest stages of hemopoiesis, prior to the development of committed lymphoid precursors (Georgopoulos et al. (1992) Science 258, 808). It is found in the hemopoietic fetal liver at day 9.5 of gestation and in the thymus from the onset of its development. In contrast, Aiolos is not detected in the nervous system, hemopoietic liver and appears in the thymus only during the later stages of its development. This indicates that Aiolos is not expressed in hemopoietic stem cells, erythroid precursors, or in the lymphoid progenitors of epidermal γδ T cells which predominate in the early thymus (Harvan et al. (1988) Nature 335, 443; Havran et al. (1990) Nature 344, 344; and Raulet et al. (1991) Immunol Rev. 120, 185). Expression in the late gestation thymus implies that Aiolos is found in double positive cells which are committed to the αβ T cell lineage and are in the process of rearranging their T antigen receptor genes.

To further characterize the relative expression of Ikaros and Aiolos during lymphocyte ontogeny, RNA from sorted lymphoid populations of wild type and mutant mice were analyzed by RT-PCR. cDNAs were prepared from FACS sorted populations isolated from the thymus, spleen, and bone marrow of wild type and mutant mice. cDNA yields were normalized to GAPDH concentrations using GAPDH primers. Aiolos and Ikaros cDNAs were amplified with gene specific primers derived from exons 3 and 7 and from exons 2 and 7, respectively, for 28 cycles. The Aiolos primers generate a single band and the Ikaros primers generate multiple bands corresponding to the alternatively spliced products of the Ikaros transcript (Georgopoulos et al. (1994) Cell 79, 143; and Molnar et al. (1994) Mol. Cell Biol. 4, 8292). Purification of the cells and RT PCR were performed essentially as set forth below.

Separation of purified cell populations were performed as follows. B220$^+$ (pro-B, preB/B and B) and B220$^-$ (T)

populations were obtained from bone marrow and spleen of wild type C57BL/6 or RAG-1-/- mice by magnetic cells sorting (Hardy et al. (1991) *J. Exp. Med.* 173, 1213–1225). First, lymphocytes were enriched by centifugation of total bone marrow or spleen cells through a layer of Lymphocyte®-M (Cedarlane Laboratories, Hornby, Canada). The enriched lymphocytes were washed twice with cold PBS/BSA (PBS supplemented with 1% BSA, 5 mM EDTA and 0.01% sodium azide.), resuspended at a concentration of $10^7$ cells/ml in PBS/BSA, and incubated at 6°–12° C. for 15 minutes with anti-B220 MicroBeads (MACS). To monitor the purity of the the positively-selected cells and the flowthrough, fluorescein isothiocyanate (FITC) conjugated rat anti-B220 antibody was added and incubated for a further five minutes. B220+ cells were separated using a MACS magnetic separation column (Miltenyi Biotec GmbH). FACS analysis of the resulting B220+ and B220– populations determined that these were 85–95% pure. Double positive and single positive thymic-cell populations were obtained by flow cytometry of cells from thymuses of wild type C57BL/6 mice. Thymic cells were incubated 30 minutes on ice with phycoerythrin (PE)-conjugated anti-CD4 and FITC-conjugated anti-CD8 antibodies (Pharmingen), after which they were washed and separated, using a Coulter sorter, into a single positive population, which included both CD4+CD8– and CD4–CD8+ cells, and CD4+CD8+ double positive population. The single positive population was then further sorted into CD4+CD8– and CD4–CD8+ populations.

Bone marrow cell suspensions were prepared from 8 to 12 week old C57BL/6J mice by gentle crushing of whole femurs and tibias in a ceramic mortar using PBS containing 2% heat inactivated fetal bovine serum (PBS/2% FBS); Cells were layered over Nycodenz with a density of 1.077 g/ml (Nycomed, Oslo, Norway) and centrifuged 30 minutes at 1000×g. The band of low density cells at the interface was removed, washed once in PBS/2% PBS, and resuspended in a cocktail of purified rat antibodies recgnizing the lineage-specific antigens CD11b/MAC-1, CD45R/B220, Ly6G/Gr-1, CD4, CD8, and Ter119 (Pharmingen, San Diego, Calif.). After a 30 minute incubation on ice, the antibody-coated cells were removed by two rounds of immunomagnetic bead depletion on a Vario MACS BS column (Miltenyi Biotec, Sunnyvale, Calif.) using a 23 G needle to restrict flow. The lineage-negative cells were then stained with FITC-conjugated D7 (anti-Sca-1) and PE-conjugated anti-c-kit (Pharmingen) for 30 minutes on ice, followed by one wash in PBS/2% FBS containing 2 $\mu$g/ml propidium iodide (PI). Viable (PI-negative) cells were sorted on a FACStarPlus (Becton-Dickinson, San Jose, Calif.). Total RNA was prepared by homogenizing the samples (350 $\mu$maximum) using QIAshredder columns and RNeasy spin columns (Qiagen). Samples of $5\times10^4$ cells were processed and the RNA was eluted in DEPC-treated water in a final volume of 30 $\mu$l. Two-color analysis of Sca-1 and c-kit revealed staining profiles identical to that reported by Okada et al., 1992. Based on these studies, Sca-1+c-kit (primitive repopulating stem cells) and Sca-1-c-kit+ (myeloid-committed progenitors) were sorted. Lineage negative cells were also stained with anti-Sca-1-FITC, anti-c-kit-PE and anti Sca-2-Red 613 and sorted into Sca-1$^+$/Sca2$^{-/lo}$, Sca-1$^+$/Sca-2$^{dull}$ and Sca-1$^+$/Sca-2$^{bright}$.

RT-PCR was performed as follows. Up to 5 $\mu$g of RNA were reverse transcribed in a total volume of 25 $\mu$l, which included 1×first strand buffer (Gibeo-BRL), 4 mM DTT, 150 ng random hexamer primers, 0.4 mM of each deoxynucleotide triphosphate, 1U Prime RNase inhibitor (5'->3', Inc.) and 200 U Superscript II reverse transcriptase (Gibco-BRL). RNA and primers, in a total volume of 12 $\mu$l, were heated to 65° C. for 10 mins before adding buffer, deoxynucleotides, DTT, RNase inhibitor, and reverse transcriptase. The reactions were incubated at 37° C. for 45 minutes, followed by an incubation at 42° C. for 45 minutes. Finally, 1 U RNase H (Gibco-BRL) was added, followed by an incubation at 37° C. for 30 minutes. cDNAs were prepared from CD4+/CD8+ and CD4+, CD8+ sorted thymocytes, Rag-1-/- thymocytes, B220+ cells from wild type bone marrow, B220+ cells from Rag-1-/- bone marrow, B220+ and B220– cells isolated from wild type spleen, Rag-1-/- spleen, Ikaros -/- bone marrow and spleen and from Sca1-/ckit+ and Sca1+/ckit+ stem cells populations. cDNA from each reaction was used directly for radiolabeled PCR. Reactions included up to 4 $\mu$l of cDNA, 1×PCR reaction buffer (Boehringer-Mannheim), 0.1 $\mu$g BSA, 100 ng each of 5' and 3' primers, 0.2 mM of deach deoxynucleotide triphosphate, and 5 $\mu$Ci each of [$\alpha$-$^{32}$P]dATP and dCTP (3000 Ci/mmol) in a total volume of 50 $\mu$l. Primers specific for Ikaros, Ex2F and Ex7R have been previously described (Georgopoulos et al. (1994) *Cell* 79, 143–156). Primers specific for Aiolos were:

AioA: ATCGAAGCAGTGCCGCTTCTCACC (SEQ ID NO:6); and

AioC: GTGTGCGGGTTATCCTGCATTAGC (SEQ ID NO:5).

Primers specific for GAPDH were:

GAPDHF: ATGGTGAAGGTCGGTGTGAACG-GATTTGGC (SEQ ID NO:13); and

GAPDHR: GCATCGAAGGTGGAAGAGTGGGAGT-TGCTG (SEQ ID NO:14).

Amplification parameters consisted of 95° C. for 5 minutes, 60° C. for 5 minutes, at which point Taq polymerase (Boehringer-Mannheim) was added to each sample, followed by 27 cycles of 95° C. for 15 seconds, 60° C. for 20 seconds, and 72° C. for 30 seconds. PCR products were visualized by electrophoresis through an 8% polyacrylamide-1×TBE gel, followed by autoradiography of the dried gels.

The results indicate that Ikaros transcripts are readily detectable in the pluripotent stem cell population that can give rise to both lymphoid and myeloid/erythroid lineages (Sca-1$^+$/c-kit$^+$ (Van de Rijn et al. (1989) *Proc. Natl. Acad Sci. USA* 86, 4634; and Okada et al. (1992) *Blood* 80, 3044). Ikaros transcripts were also found to be expressed at high levels in the more committed hemopoietic precursors (Sca-1$^-$/c-kit$^+$, mainly myeloid and erythroid precursors (Van de Rijn et al. (1989) *Proc. Natl. Acad. Sci. USA* 86, 4634; and Okada et al. (1992) *Blood* 80, 3044). In contrast, Aiolos expression was not readily detected in either of these heterogeneous populations. Low amounts of Aiolos were detected by prolonged exposure of the RT-PCR reactions in the multipotent progenitor population which is enriched for cells whose potential is restricted to the lymphoid lineages (Sca-1$^+$/c-kit$^+$/Sca-2$^+$/lin$^{-/lo}$(15)). Similar exposures failed to detect Aiolos in the pluripotent stem cell population. Low levels of Aiolos were also detected in the bone marrow of Ikaros mutant mice. These mice lack definitive lymphocyte precursors as well as more mature lymphoid cells, but the bone marrow may contain the most primitive lymphoid progenitors arrested in their differentiation. No expression of Aiolos was detected in the spleen of these mice upon prolonged exposure. Thus, in contrast to Ikaros, which is present in significant amounts from the early pluripotent stem cell stage, Aiolos is expressed only in cells which are committed to the lymphoid lineage.

Committed T cell progenitors progress from a double negative precursor through a double positive stage to the single positive thymocytes (Pearse et al. (1989) *Proc. Natl. Acad. Sci. USA* 86, 1614; and Godfrey et al. (1993) *Immunol Today* 14, 547). The double negative precursor thymocytes are rare in wild type mice. In Rag-1 deficient mice, which lack a component of the recombinase complex required for lymphocyte maturation, early B and T cell precursors are arrested in development and accumulate in the bone marrow and thymus respectively (Mobaerts, et al. (1992) *Cell* 68, 869; and Shinkai et al. (1992) *Cell* 68 855). Aiolos was barely detected in double negative pre-thymocytes isolated from the Rag-1 mutant thymus but moderate levels of Ikaros were expressed. However, Aiolos mRNA was readily detectable in immature double positive thymocytes and in the CD4 and CD8 single positive thymocytes derived from them.

In the B lineage, a similar pattern of Aiolos expression was observed. The pro-B cells isolated from Rag-1 deficient mice expressed Ikaros but very low amounts of Aiolos. Pre-B and B cells from wild type bone marrow expressed high levels of both Ikaros and Aiolos. Among cells sorted from the spleen, Aiolos was expressed at higher levels in B cells than in T cells, while Ikaros displayed the opposite pattern. Therefore, although Ikaros predominates during the early stages of T and B cell maturation, expression of Aiolos increases significantly during the intermediate stages of the T and B lineage and and comes to exceed that of Ikaros in mature B cells.

It is believed that natural killer (NK) cells are of lymphoid origin and share a common precursor with T lymphocytes (Hackett et al. (1986) *J. Immunol.* 136, 3124; and Rodenwald et al. (1992) *Cell* 69, 139). Expression of Ikaros and Aiolos was examined in the spleen of Rag-1 deficient mice which is enriched for NK cells (Mobaerts, et al. (1992) *Cell* 68, 869; Shinkai et al. (1992) *Cell* 68 855; Hackett et al. (1986) *J. Immunol.* 136, 3124; and Rodenwald et al. (1992) *Cell* 69, 139). Although Ikaros was abundantly expressed in Rag mutant splenocytes, significantly lower amounts of Aiolos were detected. In Ikaros mutant mice the spleen is populated by the non-lymphoid branch of the hemopoietic lineage (Georgepoulos et al. (1994) *Cell* 7,143). Aiolos expression was not detected among these myeloid and erythroid cells.

Figure 8:
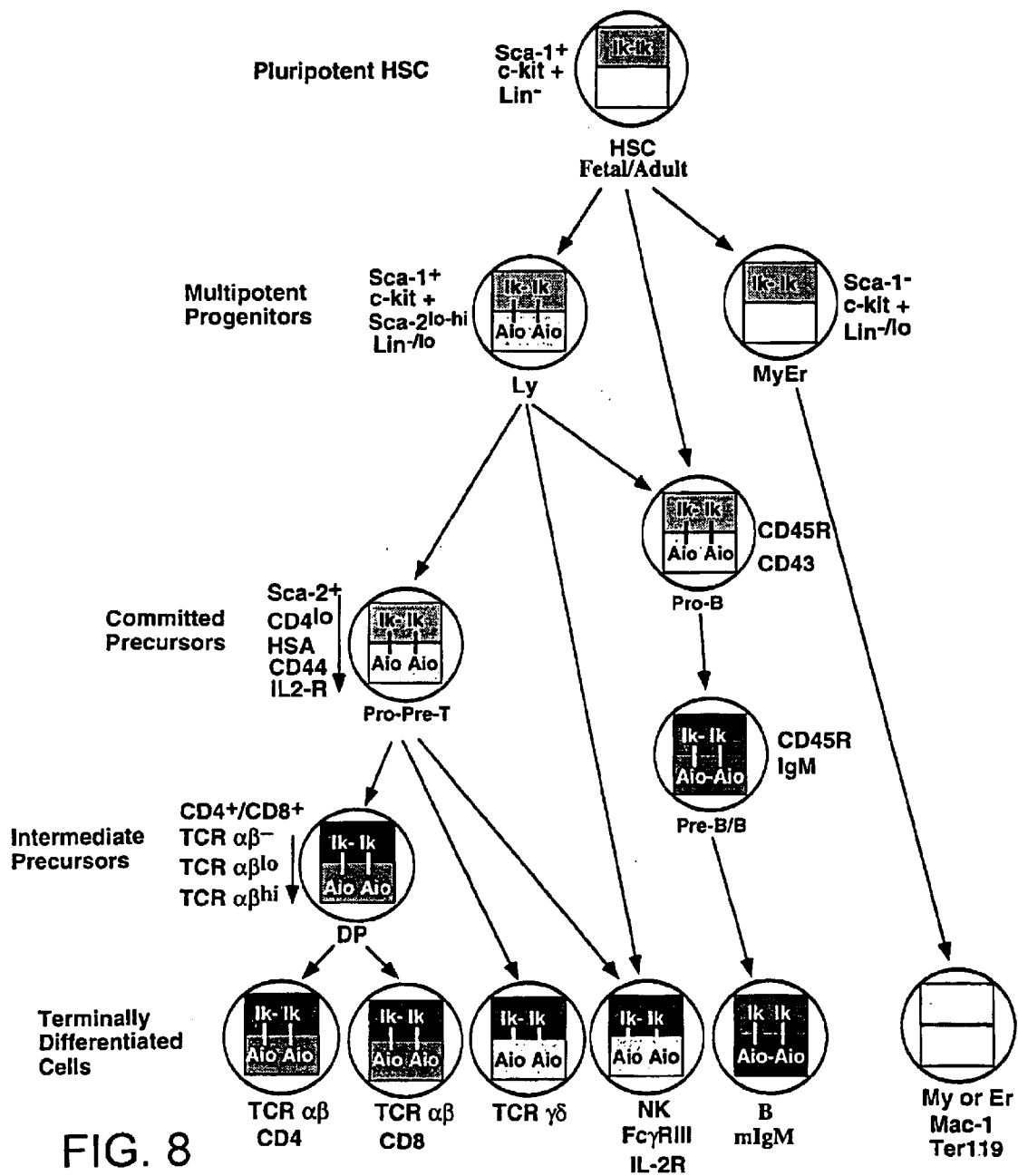
FIG. 8 is a schematic diagram depicting a model for the role of Aiolos and Ikaros in the progression of the lymphoyed lineage.

Role of Aiolos and Ikaros Homo- and Hetero-dimers in Lineage Commitment and Differentiation in the Lymphoid Lineages The expression patterns of Ikaros and Aiolos indicates that variations in the relative levels of these proteins are important for the progression of a cell through the lymphoid lineage. A model of the role of these proteins in development of the lymphoid lineages is represented in FIG. 8. Early in hemopoiesis, only Ikaros is expressed and Ikaros dimeric complexes are required and perhaps are sufficient to regulate the expression of genes that set the lymphoid fate in the differentiation of a pluripotent hemopoietic stem cell. Alternatively, interactions of Ikaros with yet undescribed and distinct factors may be required for commitment to the lymphoid lineages. As a consequence of these Ikaros mediated commitment events, Aiolos becomes expressed in primitive lymphoid progenitors and can form heterodimers with the Ikaros proteins. These Ikaros-Aiolos heterodimers are transcriptionally more active than Ikaros homodimers and may regulate the expression of genes that control the transition to definitive T and B lymphocyte precursors. As Aiolos is upregulated in pre-T (CD4$^+$/CD8$^+$) and pre-B (B220/Ig$\mu$) cell precursors, the levels of Ikaros-Aiolos heterodimers increase and may allow for the later events in lymphocyte differentiation such as V to D-J and V-J rearrangement of immunoglobulin and TCR genes to take place (Hardy et al. (1993) *J. Exp. Med.* 178, 1213 and Li et al. *J. exp. Med.* 178, 951). Finally, in mature B cells where Aiolos expression predominates, transcriptionally potent Aiolos homodimers may control functions that are unique to these mature lymphocytes. Aiolos homodimers in mature T and B cells may be essential in regulating functions of these cells including gene expression events during their activation.

Therefore, normal progression through the T and B lineages may require the sequential expression of Ikaros-Ikaros, Ikaros-Aiolos and Aiolos-Aiolos dimeric complexes. Interference with Aiolos activity may affect lymphocyte maturation and function. In mice heterozygous for the DNA binding (dominant interfering) Ikaros mutation, defects in lymphocyte development are first observed in double positive thymocytes when Aiolos expression is normally upregulated. Since at this stage in differentiation Ikaros is expressed at higher levels than Aiolos, mutant Ikaros isoforms may readily sequester Aiolos proteins in inactive heterodimers which are unable to exert their function in T cell maturation. Although these dominant negative Ikaros isoforms are also expressed in B cells, defects in this mouse are limited to the T lineage. The different ratio of Aiolos to Ikaros mRNAs in B lymphocytes may result in insufficient mutant Ikaros proteins to titrate Aiolos and block its function in the B lineage.

Formation of transcriptionally potent Aiolos homodimers in developing thymocytes may also have adverse effects on their maturation. Although mice homozygous for a deletion of the Ikaros dimerization domain generate some $\alpha\beta$ T cells, these cells differentiate abnormally. The Ikaros isoforms generated by this mutation cannot dimerize and do not prevent Aiolos from forming homodimers. The defects observed in the T lineage are consistent with the activation of transcriptional programs normally found in later stages, perhaps as a consequence of premature accumulation of Aiolos homodimers.

These studies on Aiolos and Ikaros expression and function indicate that both members of this gene family act in concert to regulate lymphocyte differentiation. At the earliest stage of lymphoid lineage determination, Ikaros is the predominant regulator of target gene activity while Aiolos is expressed at very low levels. As a cell progresses through the lymphoid lineage, Aiolos is upregulated and its heterodimers with Ikaros proteins become important regulators of the transcriptional changes required for lymphocyte maturation. Finally in mature B cells, Aiolos homodimers predominate, while in cells of the T lineage Ikaros remains expressed at relatively higher levels. Aiolos and Ikaros dimeric complexes may also regulate the function of mature B and T lymphocytes during an immune response.

Transgenic Animals

Aiolos knockouts with C terminal lesions (a deletions invoving exons 3–5) were made. Aiolos knockouts with N terminal lesions (a deletions involving the 5' end of exon 7, which contains the dimerization domain) were also made. The former knockout is a dominant negative and is thought to interfer with DNA binding. It resulted in hyperproliferation of B cells and shows increased serum levels of IgE but are otherwise normal at 2–3 weeks of age. Fifty percent of B cells were IgE secretors, thus Aiolos appears to be invovled in the Type I hyper acute response and in B cell regulation. The N terminal knockout homozygote produced no Aiolos protein, as determined by Western blotting.

Aiolos-deficient Mice

The hyperproliferative phenotype of B cells manifested in Aiolos-deficient mice indicates an important role for Aiolos in regulating the outcome of the signaling cascades that mediate B cell proliferation and differentiation to an effector cell state. Participation of Aiolos in a higher order macromolecular complex that undergoes dynamic changes during the cell cycle also indicate Aiolos' role as a critical nuclear effector for these pathways.

Lack of Aiolos has no obvious effects on differentiating thymocytes but regulates the production of B cell precursors. Late stage pro-B cells undergo a regulated proliferative expansion as they mature to the pre-B cell stage. During the pro-B to pre-B cell transition, Aiolos expression is drastically upregulated. In the absence of Aiolos, a significant increase in both the pre-B and immature B cells is detected in the bone marrow indicating an Aiolos-imposed restriction in the output from the pro-B cell compartment. Proliferation and differentiation of late-stage pro-B cells is mediated by a pre-B cell receptor complex expressed at this stage of B cell differentiation. Consistent with a role in setting the threshold for B cell receptor signaling in mature B cells, described below, Aiolos can also control the threshold for pre-B cell receptor signaling in the late stage pro-B. In the absence of Aiolos, this threshold may be set low and a greater expansion of B cell precursors or their accelerated maturation to the pre-B cell stage is manifested. Nontheless, allelic exclusion a molecular event mediated by pre-BCR signaling, remains intact. Possibly, the presence of Ikaros expressed at high levels at this stage of B cell development may rescue such potential deregulation In young (2–8 week old) Aiolos deficient mice, splenic B cells display an activated cell surface phenotype. They express high levels of MHC-Class II and CD23 and intermediate to low levels of surface IgM. This surface phenotype is similar to that of anergic B cells that have been chronically exposed to self antigens. In normal mice after their immunization, B cell entry into a germinal center (GC) reaction relies on the intimate interaction between the CD40 and B7-2 molecules with their co-receptors on T cells. Genetic defects or administration of antibodies to these co-receptors abrogate or diminish GC production and antibody responses. Interference with B, T and APC communications mediated by these surface antigens may abort an immune response at its inception. In the absence of immunization, numerous germinal centers (GC) are detected in the spleen of Aiolos mutant mice but not in their wild type littermates. Underlying infections are excluded as the cause, as they would triger similar immunological reactions in the spleen of wild type littermates. Aiolos null B cells are hyperesponsive to engagement of their IgM receptor, however, this does not warant their entry into a GC reaction. Their hyperresponsiveness to CD40 signaling in combination to IgM signaling, described below, may promote their facile entry into a GC reaction. Aiolos deficient B cells can be actively engaged in T cell-dependent immune responses by self-antigens and levels of environmental antigen which are incapable of eliciting a response in wild type lymphocytes. In support of this, a significant increase in the levels of serum IgG and IgE but not of IgM is detected in these mutant mice and autoantibodies are frequently detected in the serum of adult homozygotes. Of all the Ig isotypes, peripheral B cells in Aiolos deficient mice frequently express significant levels of the IgE receptor at the protein and at the mRNA level. An increase in IgE levels is also detected in the serum of these mice. Thus in the germinal center reactions manifested in the Aiolos mutant mice there is preferential switching to the Cε constant region. Normally, Ig switching to the γ1 and ε locus is promoted by BCR engagement in the presence of IL-4. Studies with Aiolos deficient T cells did not reveal aberrant production of IL4. Therefore, the preferential switching to the Cε locus is most likely a cell autonomous event mediated by the lack of Aiolos.

In spite of the increased production and proliferation of conventional B cells (B-2) peritoneal B1a-B cells, splenic marginal zone B cells and bone marrow recirculating B cells are severely reduced in the Aiolos deficient mice. The lower levels of serum IgM present in the Aiolos mutants may underscore the decrease in peritoneal B1a-B cells. These differential effects of the Aiolos mutation on conventional and non-conventional B lineages reveals distinct molecular requirements for their production or for their antigen driven expansion and maintenance.

In contrast to the proliferative and differentiation effects that the Aiolos mutation brings to the B cell lineage, more minor effects are apparent in T cells. Thymocyte differentiation and the number of peripheral T cells are normal. A modest increase (24 fold) in the proliferative capacity of thymocytes and mature T cells is, in effect. In contrast, a decrease in the levels of Ikaros in immature thymocytes causes a dramatic increase in their TCR mediated proliferative capacity (50–100 fold), indicating that these two closely-related nuclear effectors may be specifically tailored towards the regulation of T and B cell proliferative responses. Nontheless, a certain degree of overlap in their function in T and B lymphocytes is revealed by these studies.

In spite of the activated surface phenotype displayed by Aiolos deficient B cells, they proliferate readily upon in vitro engagement of membrane IgM, indicating that they are not anergic. In fact, Aiolos deficient B cells proliferate better than wild type controls over a range of stimulating conditions. The greater proliferative response of Aiolos deficient B cells relative to wild type is detected over a range of cell and stimulant concentration, with minimal levels of stimulant giving the maximum proliferative differential. These activation studies indicate that in the absence of Aiolos, fewer BCR engagement events are required to send a resting naive B cell into the cell cycle. In normal B cells, co-engagement of the complement receptor CD19/CD21 and membrane Ig, by complement (C3d) bearing antigen lowers the threshold for B cell activation. On the other hand, the B cell co-receptor CD22 which recruits the tyrosine phophatase SHP-1 to the BCR complex raises the threshold for BCR mediated activation possibly by intercepting CD19 signaling. Therefore, in the absence of Aiolos, the constitutive down-regulation of BCR signaling is removed.

A second type of negative regulation on BCk signaling is exerted by the low affinity for IgG FCγRIIB1 receptor through again interference with CD19 signaling. Co-ligation of membrane Ig and FCγRIIB1 receptor occurs in vivo when B cells encounter immune complexes that contain immunoglobulin and exposed antigenic determinants recognized by the BCR, and serves to attenuate onging antibody responses. In sharp contrast to wild type, B cells deficient in Aiolos, proliferated readily after in vitro treatment with the intact anti-IgM molecule indicating that negative signaling events elicited upon FCγRIIB1 receptor engagement are not in effect. In vitro engagement of the CD40 receptor also elicited a better proliferation in Aiolos null relative to wild type B cells. However, the difference in proliferation was not as great as that detected after BCR engagement. Nevertheless, engagement of both types of receptor on Aiolos deficient naive B cells may tranduce signals via their diverse signaling pathways that cause their proliferative expansion and facile differentiation into germinal center B cells.

Lack of Aiolos expression in peripheral B cells removes negative signals that intercept or interfere with BCR mediated proliferation that can now occur under minimal events of BCR engagement. There are some common features between the B cell hyperpoliferative phenotype manifested in Aiolos deficient mice and mice which lack expression of known negative signaling molecules such as the CD22, FCγRIIB1 receptors, and their signaling effectors the tyrosine phosphatase SHP-1, SHP-2, SHIP and the tyrosine kinase lyn. Since expression of these genes is normal in the Aiolos deficient B cells, the Aiolos protein may serve as a nuclear effector for B cell receptor signaling whose activity needs to be modulated in order for a resting B cell to gain entry into cell cycle. Thus Aiolos and its partner Ikaros may be the actual molecular threshold that controls entry of a resting lymphocyte into the cell cycle.

Signaling via the BCR and possibly through the diverse cascade of MAP kinases may modulate Aiolos activity and allow a B cell to enter the activated state. Aiolos and possibly its partner Ikaros may be targets for BCR and co-receptor-signaling pathways that cause their modification and allow for cell cycle progression. It is therefore significant that Aiolos and Ikaros proteins form a nuclear complex which undergoes dramatic changes upon lymphocyte activation. In resting B cells, a significant amount of the Aiolos and Ikaros proteins form discrete foci which change into toroidal structures upon activation. These Aiolos/Ikaros toroids are maintained through the S-phase during which they colocalize with mid-late DNA replication clusters. In mature T cells, formation of similar macromolecular structures containing Ikaros and possibly Aiolos proteins underly their regulated proliferation, chromosome replication and homeostasis. In accordance to Ikaros, which is a critical regulator of T cell activation and homeostasis, Aiolos which is also part of a dynamic higher order complex in B cells functions in a similar fashion. Lowering or eliminating Aiolos appears to reduce the number of nuclear effectors which serve as part of a molecular threshold for B cell activation. Less signaling events transduced from membrane receptors are required to achieve entry into the cell cycle. The lower threshold for B cell activation that still exists in the absence of Aiolos may be provided by Ikaros which is also expressed in peripheral B cells albeit at lower levels compared to Aiolos. The presence of Ikaros in the mature Aiolos deficient B cells may provide protection against spontaneous proliferation in the absence of any receptor engagement.

Signals initiated at the antigen receptor are required for B cell differentiation in the bone marrow as well as for B cell effector function and maintenance in the periphery. The Aiolos mutation affects all three phases in the life of a B cell by altering the threshold for BCR mediated entry into cell cycle. Biological consequences of the Aiolos mutation is the aforementioned increase in bone marrow B cell precursors, lack of peripheral tolerance and development of B cell lymphomas. Aiolos and Ikaros proteins clearly play an anti-proliferative role during B and T cell differentiation and function. These nuclear factors may regulate as other tumor suppressors do, the expression of cell cycle inhibitors that prevent entry into S phase. A novel and more direct role for this family of nuclear factors in the regulation of the cell cycle in lymphocytes is suggested from the present studies. Clearly Aiolos and Ikaros provide a molecular roadblock that has to be removed for the transition from G0 into G1 to take place. Their sequestration into toroidal structures during G0–G1 may do just that, but may also may mark a switch in their function from seting the threshold for lymphocyte activation to the regulation of chromosome replication and homeostasis. Aiolos/Ikaros protein incorporation into a G1/S matrix-associated three dimensional structure may serve as part of a pre-replicative complex in heterochromatin regions that licences their replication to later stages of S-phase and restricts it to once per cell cycle. Lack of or reduction in the Aiolos/Ikaros protein complex in resting B lymphocytes facilitates their entry into G1/S and causes genomic instability that leads to the generation of lymphoid malignancies. Such transformation events that occur in vivo can be recapitulated in vitro among proliferating Ikaros deficient primary T cells indicating a direct participation of these proteins in regulating the stable propagation of the genome. Since the cell cycle has evolved around the ultimate control of DNA replication, factors that belong to the Ikaros gene family may have evolved in lymphocytes to coordinate the complex series of DNA metabolic events like recombination, switching and somatic hypermutation with the DNA replication process.

Preparation of Aiolos Targeting Constructs

The Aiolos nucleic acid sequence to be used in producing the targeting construct is digested with a particular restriction enzyme selected to digest at a location(s) such that a new DNA sequence encoding a marker gene can be inserted in the proper position within this Aiolos nucleic acid sequence. The marker gene should be inserted such that it can serve to prevent expression of the native gene. As Aiolos forms a heterodimer with other nuclear receptors, e.g., with Ikaros, lesions which result in dominant negative mutations should be avoided. The position will depend on various factors such as the restriction sites in the sequence to be cut, and whether an exon sequence or a promoter sequence, or both is (are) to be interrupted (i.e., the precise location of insertion necessary to inhibit Aiolos gene expression). In some cases, it will be desirable to actually remove a portion or even all of one or more exons of the gene to be suppressed so as to keep the length of the targeting construct comparable to the original genomic sequence when the marker gene is inserted in the targeting construct. In these cases, the genomic DNA is cut with appropriate restriction endonucleases such that a fragment of the proper size can be removed.

The marker sequence can be any nucleic acid sequence that is detectable and/or assayable. For example, the marker gene can be an antibiotic resistance gene or other gene whose expression in the genome can easily be detected. The marker gene can be linked to its own promoter or to another strong promoter from any source that will be active in the cell into which it is inserted; or it can be transcribed using the promoter of the Aiolos gene. The marker gene can also have a polyA sequence attached to the 3' end of the gene; this sequence serves to terminate transcription of the gene. For example, the marker sequence can be a protein that (a) confers resistance to antibiotics or other toxins; e.g., ampicillin, tetracycline, or kanamycin for prokaryotic host cells, and neomycin, hygromycin, or methotrexate for mammalian cells; (b) complements auxotrophic deficiencies of the cell; or (c) supplies critical nutrients not available from complex media.

After the Aiolos DNA sequence has been digested with the appropriate restriction enzymes, the marker gene sequence is ligated into the Aiolos DNA sequence using methods known to the skilled artisan and described in Sambrook et al., *Molecular Cloning A Laboratory Manual*, 2nd Ed., ed., Cold Spring Harbor Laboratory Press: 1989, the contents of which are incorporated herein by reference.

Preferably, the ends of the DNA fragments to be ligated are compatible; this is accomplished by either restricting all fragments with enzymes that generate compatible ends, or by blunting the ends prior to ligation. Blunting is performed using methods known in the art, such as for example by the use of Klenow fragment (DNA polymerase I) to fill in sticky ends.

The ligated targeting construct can be inserted directly into embryonic stem cells, or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

Uses of Aiolos Deregulated Animals

Aiolos deregulated animals, for example, Aiolos misexpressing animals, e.g., mice, or cells can be used to obtain antibodies, e.g., monoclonal or polyclonal antibodies. Monoclonal and polyclonal antibodies can be produced by immunizing an Aiolos deregulated animal with an antigen. The immunization can be accomplished by administering the antigen to an animal in an immunologically effective amount, i.e., an amount sufficient to produce an immune response. The Aiolos deregulated animal is then maintained for a time period sufficient for the animal to produce cells secreting antibody molecules that immunoreact with the antigen. Such immunoreaction can be detected by screening the antibody molecules, so produced, for immunoreactivity with a preparation of the immunogen protein. Optionally, it may be desired to screen the antibody molecules with a preparation of the antigen in the form in which it is to be detected by the antibody molecules in an assay. These screening methods are well known to those of skill in the art, e.g., ELISA or flow cytometry.

Gene Therapy

The gene constructs of the invention can also be used as a part of a gene therapy protocol to deliver nucleic acids encoding either an agonistic or antagonistic form of an Aiolos polypeptide. The invention features expression vectors for in vivo transfection and expression of an Aiolos polypeptide in particular cell types (e.g., dermal cells) so as to reconstitute the function of, enhance the function of, or alternatively, antagonize the function of an Aiolos polypeptide in a cell in which the polypeptide is expressed or misexpressed.

Expression constructs of Aiolos polypeptide, may be administered in any biologically effective carrier, e.g. any formulation or composition capable of effectively delivering the Aiolos gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors-transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA encoding an Aiolos polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76, 271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:41044115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject Aiolos gene is the adeno-associated virus (AAV).

Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81 :6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an Aiolos polypeptide in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Aiolos gene by the targeted cell. Exemplary gene delivery systems of this type include liposomal derived systems, poly-lysine conjugates, and artificial viral envelopes.

In a representative embodiment, a gene encoding an Aiolos polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A43075).

In clinical settings, the gene delivery systems for the therapeutic Aiolos gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). In a preferred embodiment of the invention, the Aiolos gene is targeted to hematopoietic cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridize (e.g. bind) under cellular conditions, with the cellular mRNA and/or genomic DNA encoding an Aiolos polypeptide, or mutant thereof, so as to inhibit expression of the encoded protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

In one embodiment, the antisense construct binds to a naturally-occurring sequence of an Aiolos gene which, for example, is involved in expression of the gene. These sequences include, for example, start codons, stop codons, and RNA primer binding sites.

In another embodiment, the antisense construct binds to a nucleotide sequence which is not present in the wild type gene. For example, the antisense construct can bind to a region of an Aiolos gene which contains an insertion of an exogenous, non-wild type sequence. Alternatively, the antisense construct can bind to a region of an Aiolos gene which has undergone a deletion, thereby bringing two regions of the gene together which are not normally positioned together and which, together, create a non-wild type sequence.

When administered in vivo to a subject, antisense constructs which bind to non-wild type sequences provide the advantage of inhibiting the expression of mutant Aiolos gene, without inhibiting expression of any wild type Aiolos gene.

An antisense construct of the present invention can be delivered, for example, as an expression plasmid which, when transcribed in the cell, produces RNA which is complementary to at least a unique portion of the cellular mRNA which encodes a Aiolos polypeptide. Alternatively, the antisense construct is an oligonucleotide probe which is generated ex vivo and which, when introduced into the cell causes inhibition of expression by hybridizing with the mRNA and/or genomic sequences of an Aiolos gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

The antisense constructs of the present invention, by antagonizing the expression of an Aiolos gene, can be used in the manipulation of tissue, both in vivo and in ex vivo tissue cultures.

Transgenic Animals

The invention includes transgenic animals which include cells (of that animal) which contain an Aiolos transgene and which preferably (though optionally) express (or misexpress) an endogenous or exogenous Aiolos gene in one or more cells in the animal.

The Aiolos transgene can encode a mutant Aiolos polypeptide. Such animals can be used as disease models or can be used to screen for agents effective at correcting the misexpression of Aiolos. Alternatively, the Aiolos transgene can encode the wild-type forms of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" Aiolos gene, i.e., a deletion of all or a part of the Aiolos gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Aiolos gene. For example, excision of a target sequence which interferes with the expression of a recombinant Aiolos gene, such as one which encodes an agonistic homolog, can be designed to activate expression of that gene. This interference with expression of the protein can result from a variety of mechanisms, such as spatial separation of the Aiolos gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant Aiolos gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the Aiolos transgene could remain silent into adulthood until "turned on" by the introduction of the trans-activator.

Production of Fragments and Analogs

The inventor has provided the primary amino acid structure of an Aiolos polypeptide. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of an Aiolos polypeptide having at least one biological activity e.g., which react with an antibody (e.g., a monoclonal antibody) specific for an Aiolos polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:1 1 -1 5). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid .sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene*, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a Aiolos polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp.387–392), PhoE (Agterberg, et al. (1990) Gene 88, 3745), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of Aiolos polypeptide as disclosed herein, it is routine to perform for one skilled in the art to obtain analogs and fragments.

Peptide Analogs of Aiolos

Peptide analogs of an Aiolos polypeptide are preferably less than 400, 300, 200, 150, 130, 110, 90, 70 amino acids in length, preferably less than 50 amino acids in length, most preferably less than 30, 20 or 10 amino acids in length. In preferred embodiments, the peptide analogs of an Aiolos polypeptide are at least about 10, 20, 30, 50, 100 or 130 amino acids in length.

Peptide analogs of an Aiolos polypeptide have preferably at least about 60%, 70%, 80%, 85%, 90%, 95% or 99% homology or sequence similarity with the naturally occurring Aiolos polypeptide.

Peptide analogs of an Aiolos polypeptide differ from the naturally occurring Aiolos polypeptide by at least 1, 2, 5, 10 or 20 amino acid residues; preferably, however, they differ in less than 15, 10 or 5 amino acid residues from the naturally occurring Aiolos polypeptide.

Useful analogs of an Aiolos polypeptide can be agonists or antagonists. Antagonists of an Aiolos polypeptide can be molecules which form the Aiolos-Ikaros dimers but which lack some additional biological activity such as transcriptional activation of genes that control lymphocyte development. Aiolos antagonists and agonists are derivatives which can modulate, e.g., inhibit or promote, lymphocyte maturation and function.

A number of important functional Aiolos domains have been identified by the inventors. This body of knowledge provides guidance for one skilled in the art to make Aiolos analogs. One would expect nonconservative amino-acid changes made in a domain to disrupt activities in which that domain is involved. Conservative amino acid changes, especially those outside the important functional domains, are less likely to modulate a change in activity. A discussion of conservative amino acid substitutions is provided herein.

The general structure of Aiolos and Ikaros proteins is very similar, and four blocks of sequence are particularly well conserved. The first block of conservation encodes the zinc finger modules contained in the Ik-1 isoform which mediate DNA binding of the Ikaros protein (Molnar et al. (1994) *Mol. Cell. Biol.* 14 8292–8303). The second block of conservation has not been characterized functionally.

The third block of conservation a highly conserved 81 amino acid sequence which has been shown to mediate transcriptional activity of the Ikaros proteins (this domain is boxed in FIG. 6). This activation domain of Ikaros is composed of a stretch of acidic amino acids followed by a stretch of hydrophobic residues, both of which are required for its full activation potential. This domain from Ikaros alone or the full length Ikaros protein confers transcriptional activity of a fusion protein with the LexA DNA binding domain. This example shows that the homologous domain in Aiolos is also a transcriptional activation domain in yeast and mammalian cells and that the Aiolos transcriptional activation domain provides stronger transcriptional activity than the homologous domain from Ikaros in mammalian cells. The results show that the 232 C-terminal amino acids of Aiolos is capable of conferring transcriptional activation in yeast cells. No activity was detected with the 149 most C-terminal amino acids of Aiolos, which do not contain the conserved domain.

The fourth block of conservation corresponds to the zinc fingers which mediate dimerization. A C-terminal 149 amino acids of Aiolos which contain the two terminal zinc finger domains mediate protein dimerization.

Antibodies

The invention also includes antibodies specifically reactive with a subject Aiolos polypeptide or Aiolos-Ikaros dimers. Anti-protein/anti-peptide antisera or monoclonal antibodies can be made by standard protocols (See, for example, *Antibodies: A Laboratory Manual* ed. by Harlow and Lane (Cold Spring Harbor Press:1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject Aiolos polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Aiolos-Ikaros dimers or Aiolos polypeptide of the invention, e.g. antigenic determinants of a polypeptide of SEQ ID NO:2 or SEQ ID NO:8.

The term "antibody", as used herein, intended to include fragments thereof which are also specifically reactive with an Aiolos polypeptide or Aiolos-Ikaros dimers. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against Aiolos-Ikaros dimers or Aiolos polypeptides, or fragments or analogs thereof, and antibody fragments such as Fab' and F(ab')$_2$, can be used to block the action of an Aiolos and/or Ikaros polypeptide and allow the study of the role of an Aiolos polypeptide of the present invention.

Antibodies which specifically bind Aiolos-Ikaros dimers or Aiolos polypeptide epitopes can also be used in immunohistochemical staining of tissue samples in order to evaluate the abundance and pattern of expression of Aiolos-Ikaros dimer or Aiolos polypeptide. Anti-Aiolos polypeptide antibodies can be used diagnostically in immuno-precipitation and immuno-blotting to detect and evaluate wild type or mutant Aiolos polypeptide levels in tissue or bodily fluid as part of a clinical testing procedure. Likewise, the ability to monitor Aiolos-Ikaros dimer or Aiolos polypeptide levels in an individual can allow determination of the efficacy of a given treatment regimen for an individual afflicted with disorders associated with modulation of lymphocyte differentiation and/or proliferation. The level of an Aiolos-Ikaros dimer or Aiolos polypeptide can be measured in tissue, such as produced by biopsy.

Another application of anti-Aiolos antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject Aiolos polypeptide can then be detected with antibodies, as, for example, reacting nitrocellulose filters lifted from infected plates with anti-Aiolos polypeptide antibodies. Phage, scored by this assay, can then be isolated from the infected plate. Thus, the presence of Aiolos homologs can be detected and cloned from other animals, and alternate isoforms (including splicing variants) can be detected and cloned from human sources.

Drug Screening Assays

By making available purified and recombinant-Aiolos polypeptides, the present invention provides assays which can be used to screen for drugs which are either agonists or antagonists of the normal cellular function, in this case, of the subject Aiolos polypeptide. In one embodiment, the assay evaluates the ability of a compound to modulate binding between an Aiolos polypeptide and a naturally occurring ligand, e.g., an antibody specific for a Aiolos polypeptide or an Ikaros polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Other Embodiments

Included in the invention are: allelic variations; natural mutants; induced mutants; proteins encoded by DNA that hybridizes under high or low stringency conditions to a nucleic acids which encode polypeptides of SEQ ID NO:2 or SEQ ID NO:8 (for definitions of high and low stringency see Current Protocols in Molecular Biology, John Wiley & Sons, New York, 1989, 6.3.1–6.3.6, hereby incorporated by reference); and, polypeptides specifically bound by antisera to an Aiolos polypeptide.

Nucleic acids and polypeptides of the invention includes those that differ from the sequences discolosed herein by virtue of sequencing errors in the disclosed sequences.

Also included in the invention is a composition which includes an Aiolos polypeptide, e.g., an Aiolos/Aiolos dimer or an Aiolos/Ikaros peptide, and one or more additional components, e.g., a carrier, diluent, or solvent. The additional component can be one which renders the composition useful for in vitro, in vivo, pharmaceutical, or veterinary use. Examples of in vitro use are binding studies. Examples of in vivo use are the induction of antibodies.

The invention also includes fragments, preferably biologically active fragments, or analogs of an Aiolos polypeptide. A biologically active fragment or analog is one having any in vivo or in vitro activity which is characteristic of the Aiolos polypeptide shown in SEQ ID NO:2 or SEQ ID NO:8, or of other naturally occurring Aiolos polypeptides, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Because peptides, such as an Aiolos polypeptide, often exhibit a range of physiological properties and because such properties may be attributable to different portions of the molecule, a useful Aiolos polypeptide fragment or Aiolos polypeptide analog is one which exhibits a biological activity in any biological assay for Aiolos polypeptide activity. Most preferably the fragment or analog possesses 10%, preferably 40%, or at least 90% of the activity of an Aiolos polypeptide (SEQ ID NO:2 or SEQ ID NO:8), in any in vivo or in vitro Aiolos polypeptide activity assay.

Analogs can differ from a naturally occurring Aiolos polypeptide in amino acid sequence or in ways that do not involve sequence, or both. Non-sequence modifications include in vivo or in vitro chemical derivatization of an Aiolos polypeptide. Non-sequence modifications include changes in acetylation, methylation, phosphorylation, carboxylation, or glycosylation.

Preferred analogs include an Aiolos polypeptide (or biologically active fragments thereof) whose sequences differ from the wild-type sequence by one or more conservative amino acid substitutions or by one or more non-conservative amino acid substitutions, deletions, or insertions which do not abolish the Aiolos polypeptide biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |

TABLE 1-continued

CONSERVATIVE AMINO ACID REPLACEMENTS

| For Amino Acid | Code | Replace with any of |
|---|---|---|
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an Aiolos polypeptide analog, will ordinarily be at least about 20 residues, more typically at least about 40 residues, preferably at least about 60 residues in length. Fragments of an Aiolos polypeptide can be generated by methods known to those skilled in the art. The ability of a candidate fragment to exhibit a biological activity of an Aiolos polypeptide can be assessed by methods known to those skilled in the art, as described herein. Also included are Aiolos polypeptides containing residues that are not required for biological activity of the peptide or that result from alternative mRNA splicing or alternative protein processing events.

In order to obtain an Aiolos polypeptide, an Aiolos polypeptide-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-Aiolos polypeptide antibodies by prior art methods.

EXAMPLES

Experimental Procedures

Cloning of the Aiolos Gene, Recombination Constructs and Targeting of ES Cells

Figure 9:
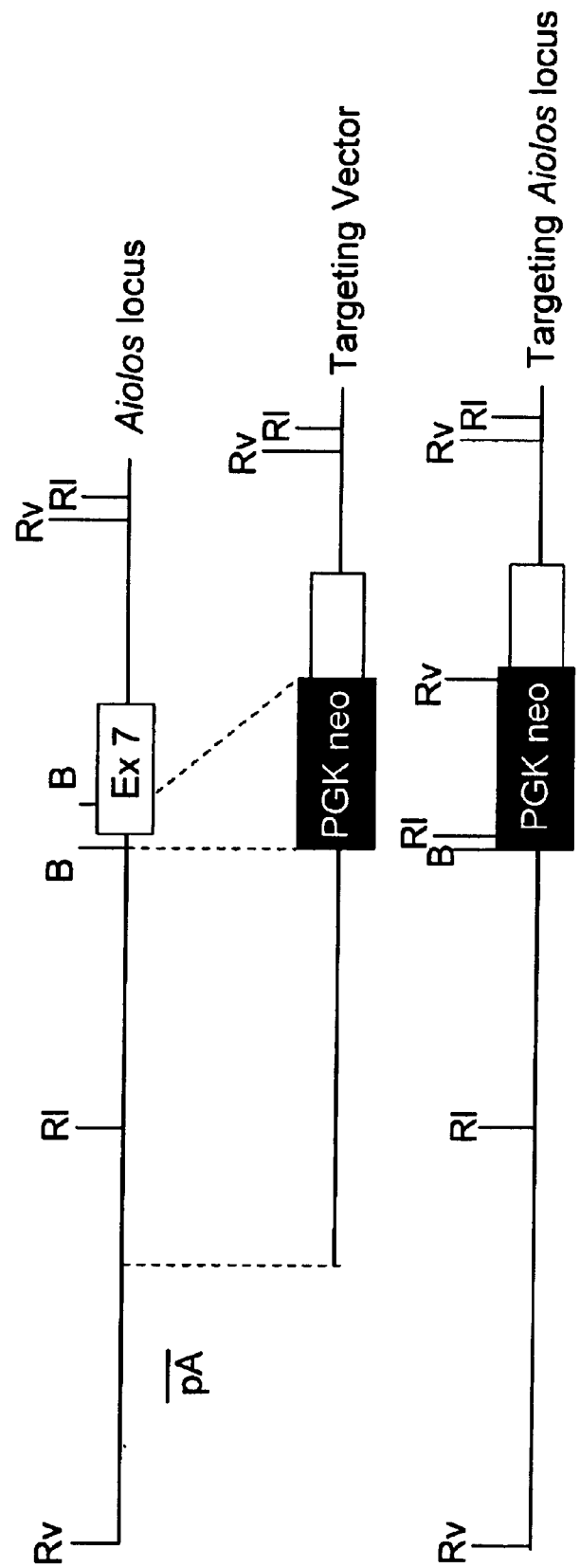
FIG. 9 is a depiction of the recombination strategy for targeting a replacement of a 0.35 kB genomic fragment encompassing the 5' coding region of exon-7 with the pgk-neo gene.

A liver genomic library made from SV129 mouse liver DNA into the phage vector 1 DASH II was screened with probes derived from the mouse Aiolos cDNA. Overlapping genomic clones were isolated that cover a region of 100 kb containing 7 translated exons. The recombination vector described in FIG. 9 was constructed with Aiolos genomic fragments from this region and the pgk-neomycin expression cassete and was transfected into J1 embryonic stem cells which were selected as previously described (Wang et at., 1996). Neomycin resistant ES cell colonies were picked and expanded. DNA was prepared and analyzed by Southern blotting using DNA probes from outside the homologous recombination area (FIG. 9). Two distinct ES cell lines heterozygous for this mutation were used in separate blastocyst injections. Female and male F1 mice with germ line transmission of the Aiolos mutation were bred to homozygocity. The genotype of F1 and F2 mice was determined by Southern and by PCR analysis of tail DNA using either probe A described in FIG. 9, or appropriate primers designed-from the neomycin (Neol) and the Aiolos gene (Int6-F and Ex7R):

Northern Hybridizations

RNA was prepared from bone marrow, spleen and thymus of wild-type and Aio −/− mice by standard acid guanidinium thiocyanate-phenol-chloroform extraction. Probes used to probe for Northern blots were as follows: The N-terminal Aiolos probe consisted of a 1.46 kb EcoRI-BamHI fragment derived from a cDNA clone of Aiolos. This fragment spans 380 bp of 5' untranslated sequence, all of exons 1–6 and 140 bp of exon 7. The C-terminal probe corresponded to a 330 bp fragment derived from exon 7 of Aiolos. Probes used to identify sterile transcripts from the C$\epsilon$, C$\gamma$1 and C$\gamma$2b sterile transcripts were derived from the vectors pE, p$\gamma$1BX and SKA, respectively, as described by Kim et al. (1996) *Nature* 383: 542–547.

Immunohistochemistry

Tissues harvested from euthanized wild type and Aiolos mutant mice were snap-frozen in OCT (Tissue Tek, Calif.), sectioned at 5–8 micron thickness, air dried for 15 minutes and stored at −80° C. until use. Anti-Ikaros and anti-Aiolos antibodies (0.2 $\mu$g/ml) were applied on sections and incubated overnight at 4° C. Sections were then treated with goat-anti-rabbit secondary antibody conjugated to HRP (VECTOR laboratories INC, Calif.). For the chromogenic reaction diaminobenzidine tetrahydrochloride (DAB) was used as a substrate and sections were counterstained with Mayer's hematoxylin. To visualize B and T cell areas in the spleen, sections were first blocked with 1:100 normal goat serum +0.3% $H_2O_2$+1 mM levamisole for 30 minutes at room temperature (RT), then incubated with anti-mouse IgM-HRP (1:200) for 60 minutes at RT and developed with DAB. Sections were then stained with biotinylated anti-mouse CD3 or PNA (1:200) for 60 minutes at RT and then developed with streptavidin-AP (1:200) and developed with AP substrate (VECTOR laboratories, kit IV). Light microscopy was performed at 10×magnification on an Olympus BMax-50 microscope.

Immunofluorescence

Whole splenocytes were prepared from wild-type mice and cultured for 48 hours in RPMI, 10% fetal calf serum, 50 $\mu$M, $\beta$-mercaptoethanol, 50 $\mu$g/ml gentamicin and 25 $\mu$g/ml lipopolysaccharide (*E. coli* serotype 0111:B4, Sigma). For immunofluorescence studies, both resting and LPS-activated cells were used. Unless specified otherwise, all manipulations were performed on ice using pre-chilled solutions. Cells were cytospun onto slides at room temperature and fixed for 20 minutes in cold phosphate buffered saline (PBS)/4% paraformaldehyde/0.1% Tween-20. After washing in cold PBS, the slides were incubated for 1 hour at room temperature with 100 $\mu$l blocking buffer (PBS, 3% BSA/1% normal donkey serum/1% normal goat serum). Aiolos and Ikaros proteins were detected by an overnight incubation at 4° C. using an affinity-purified rabbit antibody specific for the N-terminal portion of Ikaros and Aiolos, followed by cold PBS washes and incubation for 1 hour at room temperature with either Cy5- or FITC-conjugated donkey anti-rabbit secondary antibodies (Jackson ImmunoResearch Laboratories, Inc.). To visualize replication foci, BrdU was added to the cell culture at a final concentration of 10 $\mu$M 10 minutes prior to harvesting the cells. After fixing and staining for Aiolos, the slides were fixed and stained for BrdU (Leonhardt et al., 1992) using a monoclonal antibody (Becton-Dickinson) and FITC-conjugated goat anti-mouse secondary antibody (Jackson ImmunoResearch Laboratories, Inc.). Slides were mounted in Vectashield (Vector Laboratories, Inc.) and viewed by scanning confocal microscopy using a Leica microscope. Images were processed using Adobe Photoshop software.

Cytofluorimetric Analysis of Lymphoid Populations

Aiolos mutant mice were analyzed in parallel to age matched wild type controls. At least 10 groups of mutants and wild type animals between 2–16 week of age were analyzed. In each experimental group individual animals were analysed for their lymphoid populations in the bone marrow, spleen, thymus and lymph nodes. Single cell suspensions of thymus, spleen and bone marrow cells were incubated with PE and FITC conjugated mAb for 30 minutes on ice. Cells were then washed 3 times with PBS and one- and two-color flow cytometric analyses were performed on a FACScan (BectonDickinson, San Jose, Calif.). Gating for viable cells was performed using propidium iodide. Isotype matched control antibodies were used as negative controls. Ten-thousand cells were analyzed for each sample. The following antibodies to lineage specific differentiation antigens were used: TER-119 (Pharmingen), M1/70.15 (Caltag), Gr-1 (RB6-8C5-Pharmingen), CD45R (RA3-6B2-Pharmingen), CD43 (S7-Pharmingen), IgM (R6-60.2 and Pharmingen), IgD, CD8 (53-6.7, 53-5.8-Pharmingen), CD4 (RM4-4-Pharmingen), CD25 (7D4), TCR$\alpha\beta$ (H57-597-Pharmingen), IgE etc.

Cell cycle analysis of pro-B and pre-B cell populations Red blood cells depleted BM Ad cells were harvested and labeled with FITC conjugated antiCD45R monoclonal antibody, washed once in PBS and fixed with ice cold 90% ethanol overnight. Fixed cells were centrifuged, washed once in PBS/1% fetal calf serum and incubated for 30 minutes at 37° C. in PBS/1% fetal calf serum/50 $\mu$g/ml propidium iodide and 0.25 mg/ml of RNAseA. Before flow cytometric analysis cells were filtered through a 70 $\mu$m cell strainer to disrupt doublets. Remaining doublets, apoptotic cells and cell debris were excluded in the analysis on a FACScan flow cytometer (Becton Dickinson).

Lymphocyte Activation Assays

Single cell suspensions were made from one to two month old thymi and spleens. For B cell enrichment (90%), splenocytes were treated with biotinated anti-mouse CD3, anti-mouse Mac-1 and anti-mouse TER119 monoclonal antibodies, straptavidin conjugated magnetic beads and passed through a MAC column (BS, Miltenyi, Biotech). B cells were plated in triplicates at 5–40×$10^4$ cells/well in flat-bottomed 96 well plates and cultured with media alone or with media+IgM (10 $\mu$gs/ml) or +IgM (Fab)$^2$ (10 $\mu$gs/ml) for 48 hours and then pulsed with 1 $\mu$Ci of [$^3$H] thymidine for an additional 12 hours. Cells were harvested using a betaplate reader. For TCR stimulation, thymocytes or T cells were plated in triplicates at 25–200×$10^3$ cells/well in a 96 well plate precoated with anti-TCR monoclonal antibody (10 $\mu$g/ml).

ELISA

Mouse immunoglobulin isotype-specific enzyme-linked immunosorbent assays (ELISA) were carried out using isotype specific rabbit anti-mouse immunoglobulins (Sigma) as the capture agent to which serum samples were added. Captured immunoglobulin isotypes were developed with goat anti-mouse IgG+A+M directly conjugated to alkaline phosphatase (Sigma). Purified myeloma proteins (Sigma) were used to generate a standard curve. The immunoglobulin isotype concentrations of individual serum samples were calculated by comparing the mean O.D. obtained from tiplicate wells to the standard curve. For anti-TNP and anti-Ikaros antibody determination sample sera were added to wells coated with TNP-BSA or murine recombinant Ikaros protein. Wells were blocked with 2% BSA, incubated with serum samples, washed extensively and developed with goat anti-mouse IgG+A+M conjugated to alkaline phosphatase.

T-dependent B Cell Response

TNP-OVA (100 µg) and mouse recombinant IKAROS protein (6–60 µg) in CFA (Sigma) were administered by intraperitoneal injection. Serum titers of antigen-specific antibodies were determined 10 days after immunization by ELISA.

Example 1

Generation of an Aiolos-null Genomic Locus

A recombination vector ($\Delta 7$) that replaces a 0.35 kB BamHI genomic fragment containing the 5' splice acceptor site of Aiolos exon-7, with the pgk-neomycin expression cassete was targeted by homologous recombination into the Aiolos locus (FIG. 9). This deletion was designed to disable utilization of exon-7 in the Aiolos transcript. The targeting vector (shown in FIG. 9) was homologously recombined in the mouse germ line at a 1:10 frequency. Two independent embryonic stem cell lines with legitimate homologous recombination events were used to generate mice with germ line transmission for the $\Delta 7$ deletion. Homozygous $\Delta 7$ mutant mice were born with the expected Mendelian frequency and were indistinguishable from their wild-type littermates. Lymphoid populations produced in the Aio-$\Delta 7-/-$ mice do not express any form of Aiolos mRNA. Probes made from Aiolos exons-1–5 and exon-7 failed to detect any Aiolos transcript in the Aio-$\Delta 7-/-$ mice, but Ikaros mRNA was readily seen. In addition, the B cell areas of peripheral lymphoid follicles in wild type mice stained brightly with an Aiolos polyclonal antibody (raised to epitopes outside the deleted region), whereas lymphoid follicles from the Aio-$\Delta 7-/-$ mice did not. Nevertheless, both stained positively with an antibody specific for the Ikaros protein. In conclusion, replacement of the 5' end of Aiolos exon-7 with the pgk-neo gene generated an Aiolos-null allele.

Example 2

Increase in Pre-B and Immature B Cells and Decrease in Recirculating B Cells in the Bone Marrow of Aiolos Null Mice.

Studies on B cell populations in Aio-$\Delta 7-/-$ mice indicated that Aiolos plays a non-redundant function during B cell differentiation. In the absence of Aiolos, a significant increase in the number of B cell precursors was detected in the bone marrow. A 0.5–3-fold increase was detected in the pre-B cell (CD45R$^+$/IgM$^-$) compartment. The increase in pre-B cells was not due to a maturation block towards the B cell stage, as newly produced bone marrow B cells (CD45R$^+$/IgM$^+$) were also expanded to a similar degree. Given the increase in the Aiolos pre-B cell compartment, whether more of these cells were in cycle relative to their wild type counterparts was tested. No significant difference in the number of cycling cells was detected between wild type and Aio-$\Delta 7-/-$, CD4SR$^+$ populations. These data indicate that the increase in bone marrow pre-B/B cells detected in Aiolos-deficient mice may be due to an increase in the input from the pro-B cell compartment rather than a change in their cycling status. Late-stage, pro-B cells undergo a pre-B cell receptor (BCR) mediated proliferative expansion as they differentiate into pre-B cells. Aiolos, which in normal mice is drastically upregulated during the pro-B to pre-B cell transition may be responsible for negatively regulating their pre-BCR mediated proliferative expansion at this early stage of B cell differentiation.

In immature B cells, ligation of the pre-B cell receptor leads to a shut down of the , unrearranged immunoglobulin heavy chain locus in a process known as allelic exclusion. Given a potential deregulation in negative signaling in pre-B cells in the Aio-$\Delta 7-/-$ mice which may result in their proliferative expansion, whether they underwent allelic exclusion was examined. Mutually exclusive expression of the IgM$^a$ and IgM$^b$ alleles on Aio-$\Delta 7-/-$ B cells produced by a mixed genetic background (SV129×C57) indicated that allelic exclusion is in order.

In contrast to the increase in Aio-$\Delta 7-/-$ pre-B and B cells, the recirculating and long-lived CD45R$^{++}$/IgM$^+$ bone marrow B cells were significantly reduced. Interestingly, although recirculating B cells were fewer in number relative to their wild type counterparts, a greater proportion of these cells was in cycle. Given the increase in bone marrow pre-B/B cell compartment and the decrease in the recirculating compartment, the B cell composition of the blood was tested. A small increase in CD45R$^+$/IgM$^{+++}$/IgD$^\pm$ and a decrease in the CD45R$^{++}$/IgM$^+$/IgD$^{+++}$ populations was detected which correlates directly with the increase in the production of bone marrow B cells and a decrease in recirculating B cells coming from the peripheral lymphatic centers (see Table 1).

TABLE 1

B CELL POPULATIONS IN THE BLOOD

| | +/+ | | | | | | -/- | | | | | |
|---|---|---|---|---|---|---|---|---|---|---|---|---|
| CD45R$^+$/IgM$^{+++}$ | 4.21 | 6.52 | 3.00 | 3.96 | 3.19 | | 4.53 | 4.65 | 6.12 | 4.51 | 10.19 | |
| CD45R$^+$/IgM$^+$ | 8.66 | 12.21 | 8.84 | 10.52 | 8.85 | | 8.37 | 6.50 | 7.39 | 5.55 | 10.66 | |
| R-IgM$^{+++/+}$ | 0.49 | 0.53 | 0.34 | 0.38 | 0.36 | 0.42 ± .08 | 0.54 | 0.72 | 0.83 | 0.81 | 0.96 | 0.77 ± .15 |

TABLE 1-continued

B CELL POPULATIONS IN THE BLOOD

| | +/+ | | | | | | -/- | | | | |
|---|---|---|---|---|---|---|---|---|---|---|---|
| IgM+/IgD± | 3.19 | 5.87 | 2.14 | 5.64 | 3.32 | | 3.66 | 5.97 | 5.38 | 5.07 | |
| IgM+/IgD+ | 10.20 | 21.00 | 10.93 | 15.37 | 11.69 | | 7.82 | 8.99 | 6.30 | 8.89 | |
| R-IgD±/+ | 0.31 | 0.28 | 0.20 | 0.37 | 0.28 | 0.29 ± .06 | 0.47 | 0.66 | 0.85 | 0.57 | 0.64 + .16 |

Example 3
Aiolos-deficient Peripheral B Cells Display an Activated Cell Surface Phenotype In this example, cells obtained from the spleen and the peritoneum of four week old wild type and Aiolos A-7-/- littermates were analyzed with the following combinations of mAbs: (A) anti-CD45RPE/anti-IgMFITC, (B) anti-IgDPE/anti-IgM};llC, (C) anti-(:D45RPE/anti-Class IIFITC, (D) anti-CD45RPE/anti-CD5$^{FITC}$. No significant difference in the relative and absolute number of splenic B cells was observed between Aio-Δ7-/- and wild type littermates analyzed between one to two months after birth. However, the cell surface phenotype of Aio-Δ7-/- splenic B cells was different to that of wild type controls. Among the Aio-Δ7-/- splenocytes, the percentage of newly exported naive B cells (CD45R+/IgM+++ and IgM++/IgD±) was notably decreased, whereas the number of germinal center B cells (CD45R++/IgM±) was increased. The number of CD45R+/IgM+/IgD+ that constitutes the majority of splenic B cells was similar to wild type. However, there was a dramatic increase in the number of mutant splenic B cells that expressed high levels of Class II-MHC, which is normally upregulated during B cell activation. In sharp contrast, only a small percentage of the wild type B cell population expressed high levels of this activation antigen. The number of cells expressing the CD23 activation marker was also increased among the Aiolos null relative to wild type peripheral B cells. On the other hand, expression of the FcγRIIB1 and CD22 receptors, which play negative roles in BCR signaling was comparable between mutant and wild type B cells.

The increase in the number of CD45R++/IgM± and Class II++ expressing B cells indicate that a significant amount of Aio-Δ7-/- splenic B cells are in an activated state. Consistent with this activated B cell surface phenotype, immuno-histochemical analysis of splenic sections from one- to two-month-old unimmunized Aio-Δ7-/- mice revealed numerous germinal centers which were not detected in the wild type. Formation of germinal centers is the hallmark of a T-dependent antigen-specific B cell response. B cells within the germinal center are mainly of IgM+/PNA+ surface phenotype and are in the process of undergoing clonal expansion combined with somatic hypermutation, affinity maturation and isotype switching. The presence of germinal centers in the spleen of Aiolos deficient mice but not in their wild type littermates suggests that mutant B cell populations are actively engaged in a Tdependent antigen-specific maturation process, perhaps by antigens which are unable to elicit an immune reaction in wild type B cells. Self-antigens or low levels of environmental antigens that drive B cells to a state of immunological tolerance may not do so in the absence of Aiolos.

Example 4
Lack of a Marginal Zone and Peritoneal B Cells in Aiolos Deficient Mice In this example, sections obtained from the spleen of 6 week old wild type and Aiolos A-7-/- mice were treated with anti-IgM, -anti-CD3 and PNA. This immunohistochemical analysis of splenic sections from Aiolos-deficient mice revealed an extensive network of germinal centers which formed in the absence of immunization. However, the marginal zone, which separates the white from the red pulp and contains B cells that stain brightly with IgM, was either absent or drastically reduced. Phenotypic analysis of splenic lymphocytes also showed a reduction in the CD45R+/IgM+++/IgD± B cells, consistent with the immunohistochemical data. Marginal zone CD45R+/IgM++/IgD− cells and the phenotypically similar peritoneal B1-a B cells, both of which recognize carbohydate antigens, are proposed to derive from a distinct progenitor from of that of conventional B cells. Significantly, peritoneal B1-a cells were also absent or severely reduced in Aio-Δ7-/- mice, suggesting that the two non-conventional B lineages require Aiolos for their production or maintenance.

Example 5
Autoantibodies and Elevated Levels of Serum Immunoglobulins in Aiolos-deficient Mice To determine whether Aiolos-deficient mice respond to self-antigens and thus produce auto-antibodies, their serum was tested against kidney sections from wild-type controls. The majority of sera from 5–10 week old mutants was reactive against nuclear auto-antigens present on kidney sections. Sera from age matched controls did not demonstrate any significant levels of auto-antibodies.

In addition to the germinal centers detected in the spleen of Aiolos deficient mice and to the presence of circulating auto-antibodies these mutants exhibit an increase in the level of serum immunoglobulins. On average, the majority of animals tested had elevated levels of IgG1, IgG2a and IgE but not of IgM, IgG2b and IgG3, relative to wild type. The increase in the levels of IgG and IgE isotypes, which is usually detectable in the serum of animals after a secondary immune response, suggests that B cell populations in the germinal centers of the Aiolos mutant mice are switching to the γ and ε loci and differentiating into IgG and IgE producing plasma and memory B cells.

Among the Aiolos mutant mice analysed, in some cases a significant proportion of peripheral B cells were positive for the IgE receptor. Furthermore, mRNA analysis of spleens of unimmunized Aiolos mutants revealed significant levels of IgE transcripts in 50% of the mutant population whereas other constant region transcripts were not present at any significant amount. IgE transcripts were not expressed in the spleen of unimmunized wild type controls analysed in parallel.

Example 6
Lack of Negative Signaling and Augmentation of BCR Mediated Proliferative Responses in Aiolos-null B Cells Given the activated B cell phenotypes detected in unimmunized Aiolos-deficient animals, the ability of Aio-Δ7-/- peripheral B cells to proliferate upon immunoglobulin receptor engagement was tested in vitro. Coligation of the low affinity receptor for IgG, FcγRIIB1, and BCR by an intact anti-mouse μ antibody interferes with $Ca^{2+}$ mobilization and B cell proliferation normally mediated by signaling via the IgM receptor. Aiolos deficient B cells, exhibited a 3.5–20 fold increase in proliferation after treatment with an intact anti-IgM antibody over a range of cell concentrations whereas wild type B cells were unresponsive. This indicates that negative signaling via the Fcγ RIIB1 receptor is less effective in the absence of Aiolos.

Importantly, Aiolos deficient B cells proliferated better than wild type even after engagement of their IgM receptor via an anti-IgM F(ab)$_2$ fragment and in the absence of negative signals transduced by the FcγRIIB1 receptor. The proliferation index of Aio-Δ7-/- relative to wild type B cells was 2–3 fold greater over a range of cell concentrations. In addition, anti-IgM F(ab)$_2$ was able to stimulate better proliferative responses from Aio-Δ7-/- B cells relative to wildtype over a range of antibody concentration (0–10 μg IgM-F(ab)$_2$). The difference in proliferation between mutant and wild type B cells was greater at low concentrations of stimulating antibody, indicating that the signaling threshold for BCR mediated proliferation was lower in Aiolos mutant compared to wild type B cells.

These studies reveal a deregulation in a negative BCR signaling pathway that sets the threshold for B cell proliferation and is distinct from the one that lies downstream of the FcγRIIB1 receptor.

Given the extensive germinal center network present in the spleens of Aiolos deficient unimmunized animals, we tested the ability of Aio-Δ7-/- B cells to proliferate after CD40 engagement. A 50–70% increase in the proliferative capacity of Aio-,&7-/- B relative to wild type was detected. The CD40 mediated gain in proliferative capacity of Aio-Δ7-/- versus wild type B cells is rather mediocre when compared to that caused by engagement of the IgM receptor in the same mutant population, nontheless, lower signal transduction thresholds in both of these pathways may account for the facile differentiation of an Aiolos deficient B cell into a germinal center lymphocyte.

Example 7

Proliferative Responses in Aio-Δ7-/- T Cells

In this example, cells obtained from the thymus and spleen of a four-week old wild type and Aiolos A-7-/- littermates were analyzed with the following combinations of mAbs: anti -CD4PE/anti-CD8FITC, anti-CD4PE/anti-TCRFITC, anti-CD8PE/anti-TCRFITC. Thymocytes and splenocytes (4–20×10$^4$) were activated with plate-bound antiTCR antibody or hamster IgG control (20 μg/ml) for 48 hours and $^3$H-thymidine incorporation was used to estimate their progression into S-phase. Thymocyte differentiation was indistinguishable from that of wild type controls and peripheral T cells were present in normal numbers in Aiolos deficient animals. Signaling via the TCR had a quantitatively less dramatic but qualitatively a similar proliferative effect to the one exerted upon BCR signaling in Aiolos deficient B cells. A rather modest, 2–3 fold increase, in TCR mediated proliferative responses of Aio-Δ7-/- thymocytes was detected. Peripheral Aio-Δ7-/- T cells exhibited from a 30% to a 4 fold increase in TCR mediated proliferation relative to wild type mature T cells over a range of cell concentration. Intermediate to high cell concentrations exhibited the greatest proliferative response to the stimulating plate bound α-TCR antibody.

Example 8

T-dependent Humoral Immune Responses in Aiolos Deficient Mice

In this example, four wild type and eight Aiolos deficient mice were immunized with OVA-TNP (100 μg) and mouse Ikaros protein (6–60 μg). The TNP response was estimated by ELISA. Immunization of animals with T-dependent antigens caused the initial secretion of low affinity IgM antibodies followed by somatic mutation, affinity maturation and switch to Ig isotypes, events that take place predominantly in the germinal center. Since Aiolos deficient mice have numerous and well developed splenic germinal centers with B cells that exhibit an activated cell surface phenotype (Class II$^{++}$) whether they could mount an immune response or whether they were anergic to subsequent stimulation with T-dependent immunogens, were tested. Given the decrease in the recirculating B cell compartment in the bone marrow (CD45R$^+$/IgM$^+$) that contains memory B cells, the ability of Aiolos deficient mice to elicit but also maintain an immune response was estimated. Aiolos Δ7-/- and wild type littermates were immunized and then boosted with 100 μg of TNP-OVA. Wild type and Aiolos mutant mice gave similar anti-TNP antibody responses over a period of three weeks. The ability of Aiolos deficient and wild type mice to mount an immune response against self antigens was also determined. Murine Ikaros protein was injected into a group of wild type and Aiolos deficient mice and their ability to respond was tested two weeks after the first boost. The average antibody response to mouse Ikaros was greater in the Aiolos mutant animals compared to wild type.

Example 9

Development of Lymphomas in Aging Aiolos-null Mice

Among the aging Aiolos null mouse population a significant incidence of lymphomas was noted. Within a small group of twenty Aiolos deficient mice which range in age between eight to ten months, five animals developed lymphoproliferative disease in the periphery. Of the four sick mice analyzed three had B cell lymphoproliferations whereas one had T cell lymphoproliferation. B but not the T cell clones from these animals were successfully propagated in vitro supporting a transformed phenotype. In addition to mice that develop lymphomas, sick mice with no obvious signs of lymphoproliferative disease have also been noted but they died prior to analysis.

Example 10

Aiolos is Part of a Macromolecular Protein Complex that Undergoes Dramatic Changes upon B Cell Activation and Colocalizes with DNA Replication Foci in S Phase In this example, resting and LPS activated splenocytes from a wild type mouse were fixed and stained for Aiolos or Ikaros proteins. In the absence of Aiolos the activation threshold of a resting B cell is drastically reduced. It is thus possible that for activation of a normal B cell, Aiolos activity must be modulated and BCR and other signaling pathways may be mediating such an effect. In accordance with such a hypothesis, in resting B cells Aiolos but also Ikcaros proteins display a punctate pattern of staining with discrete foci discerned over a more diffuse (fine speckles) area. However, upon B cell activation Aiolos foci are sequestered into toroidal structures that occupy a significant part of the nuclear volume. Ikaros protein which is also part of this macromolecular complex in B cells behaves in a similar fashion. Importantly, during S phase, Aiolos and Ikaros toroids colocalize with nuclear matrix associated BrdU labelled DNA replication clusters suggesting a novel role for these proteins during S phase which may relate to chromosome eplication-and homeostasis.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method of obtaining an antibody, comprising:
providing a mammal that (a) has a pro-B cell which is Aiolos (SEQ ID NO:2 or 30) deregulated and (b) is immunized with an antigen recognized by the pro-B cell; and
isolating an antibody against the antigen from the mammal or from a B cell derived from the mammal, to thereby obtain an antibody.

2. The method of claim 1, wherein the mammal is a mouse.

3. The method of claim 1, wherein the mammal is an Aiolos transgenic mouse.

4. The method of claim 1, wherein the antigen is an autoantigen.

5. The method of claim 1, wherein the mammal is immunized with an alloantigen or xenoantigen.

6. The method of claim 5, wherein the antigen is poorly antigenic in wild type animals.

7. The method of claim 5, wherein the antigen has at least 90% homology between the first and second species as determined using the ALIGN program with a PAM120 weight residue table, a gap length penalty of 12, and a gap penalty of 4 or using XBLAST with default parameters, wherein the first species is the animal which provides the antibody and the second species is the species which provides the antigen.

8. The method of claim 1, wherein the antibody is an IgG antibody.

9. The method of claim 1, wherein the mammal carries homozygous null mutations at the Aiolos gene.

10. The method of claim 1, further comprising isolating one or more B cells from the mammal and isolating the antibody from the isolated B-cells.

11. The method of claim 1, wherein the B cell from the animal is fused with a second cell to provide a hybridoma and the antibody is isolated from the hybridoma.

12. A method of obtaining an antibody comprising:
providing a mouse that (a) has a pro-B cell which is homozygous for null or underexpressing mutations at the Aiolos (SEQ ID NO:2) locus and (b) is immunized with an antigen recognized by the pro-B cell; and
isolating an antibody against the antigen from the mouse, to thereby obtain an antibody.

13. The method of claim 12, wherein the mouse is an Aiolos transgenic mouse.

14. The method of claim 12, wherein the antigen is an autoantigen.

15. The method of claim 12, wherein the mouse is immunized with an alloantigen or xenoantigen.

16. The method of claim 15, wherein the antigen is poorly antigenic in wild type animals.

17. The method of claim 15, wherein the antigen has at least 90% homology between the first and second species as determined using the ALIGN program with a PAM120 weight residue table, a gap length penalty of 12, and a gap penalty of 4 or using XBLAST with default parameters, wherein the first species is the animal which provides the antibody and the second species is the species which provides the antigen.

18. A method of obtaining a monoclonal antibody, comprising:
providing a mouse that (a) has a pro-B cell which is homozygous for null or underexpressing mutations at the Aiolos (SEQ ID NO:2) locus and (b) is immunized with an antigen recognized by the pro-B cell;
isolating a B cell from the mouse; and
isolating an antibody against the antigen from the B cell or a derivative of the cell, to thereby obtain an antibody.

19. The method of claim 18, wherein the derivative is a hybridoma.

20. The method of claim 18, wherein the mouse is an Aiolos transgenic mouse.

21. The method of claim 18, wherein the antigen is an autoantigen.

22. The method of claim 18, wherein the mouse is immunized with an alloantigen or xenoantigen.

23. The method of claim 18, wherein the antigen is poorly antigenic in wild type animals.

24. The method of claim 1, wherein the mammal is homozygous for a deletion of exon 7 of the Aiolos gene or a portion thereof.

25. The method of claim 12, wherein the mouse is homozygous for a deletion of exon 7 of the Aiolos gene or a portion thereof.

26. The method of claim 18, wherein the mouse is homozygous for a deletion of exon 7 of the Aiolos gene or a portion thereof.

* * * * *

UNITED STATES PATENT AND TRADEMARK OFFICE
CERTIFICATE OF CORRECTION

PATENT NO. : 6,890,534 B1
DATED : May 10, 2005
INVENTOR(S) : Bruce A. Morgan and Katia Georgopoulos It is certified that error appears in the above-identified patent and that said Letters Patent is hereby corrected as shown below:

Title page,
Item [56], References Cited, OTHER PUBLICATIONS,
"Singh" reference, before "Molecular" insert -- " --; and after "DNA" insert -- " --.
"Rudnicki" reference, replace "Muscule" with -- Muscle --.
"Travis" reference, before "enhancer" replace "$\beta$" with -- $\alpha$ --.
"Karasuyama" reference, replace "$V_{pre-B}\lambda 5$" with -- $V_{pre-B}/\lambda 5$ --.
"Leiden" reference, after "The" and before "TCR" replace "$\beta$" with -- $\alpha$ --.
"Franzoso" reference, replace "select$\kappa$B" with -- select $\kappa$B --.
"Boise" reference, after "bcl-x," and before "bcl-2" insert -- a --.
"Wang" reference, replace "Ailos" with -- Aiolos --.

Signed and Sealed this

Fourteenth Day of March, 2006

JON W. DUDAS
*Director of the United States Patent and Trademark Office*